US008343967B2

(12) United States Patent
Ding et al.

(10) Patent No.: US 8,343,967 B2
(45) Date of Patent: Jan. 1, 2013

(54) APOPTOSIS-INDUCING AGENTS FOR THE TREATMENT OF CANCER AND IMMUNE AND AUTOIMMUNE DISEASES

(75) Inventors: Hong Ding, Lincolnshire, IL (US); Steven W. Elmore, Northbrook, IL (US); Laura A. Hexamer, Grayslake, IL (US); Aaron R. Kunzer, Arlington Heights, IL (US); Cheol-Min Park, Singapore (SG); Andrew J. Souers, Evanston, IL (US); Gerard M. Sullivan, Lake Villa, IL (US); Michael D. Wendt, Vernon Hills, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 13/458,968

(22) Filed: Apr. 27, 2012

(65) Prior Publication Data

US 2012/0214796 A1    Aug. 23, 2012

Related U.S. Application Data

(62) Division of application No. 13/049,569, filed on Mar. 16, 2011, now Pat. No. 8,188,077.

(60) Provisional application No. 61/317,575, filed on Mar. 25, 2010.

(51) Int. Cl.
| *A61K 31/5377* | (2006.01) |
| *A61K 31/5375* | (2006.01) |
| *A61K 31/435* | (2006.01) |
| *A61K 31/437* | (2006.01) |
| *C07D 413/02* | (2006.01) |
| *C07D 241/02* | (2006.01) |
| *C07D 295/00* | (2006.01) |
| *C07D 211/00* | (2006.01) |

(52) U.S. Cl. ............... 514/231.2; 514/247; 514/277; 514/317; 544/129; 544/224; 544/392; 546/192; 546/206

(58) Field of Classification Search ............... 514/231.2, 514/247, 277, 317; 544/129, 224, 392; 546/192, 546/206
See application file for complete search history.

(56) References Cited

U.S. PATENT DOCUMENTS

| 6,720,338 | B2 | 4/2004 | Augeri et al. |
| 7,390,799 | B2 | 6/2008 | Bruncko et al. |
| 7,511,013 | B2 | 3/2009 | Molino et al. |
| 7,514,068 | B2 | 4/2009 | Tung |
| 7,521,421 | B2 | 4/2009 | Naicker et al. |
| 7,528,131 | B2 | 5/2009 | Persichetti et al. |
| 7,531,685 | B2 | 5/2009 | Czarnik |
| 7,534,814 | B2 | 5/2009 | Ascher et al. |
| 7,767,684 | B2 | 8/2010 | Bruncko et al. |
| 7,973,161 | B2 | 7/2011 | Bruncko et al. |
| 2005/0049594 | A1 | 3/2005 | Wack et al. |
| 2007/0015787 | A1 | 1/2007 | Bruncko et al. |
| 2008/0182845 | A1 | 7/2008 | Bardwell et al. |
| 2009/0082471 | A1 | 3/2009 | Czarnik |
| 2009/0088416 | A1 | 4/2009 | Czarnik |
| 2009/0093422 | A1 | 4/2009 | Tung et al. |
| 2009/0105147 | A1 | 4/2009 | Masse |
| 2009/0105307 | A1 | 4/2009 | Galley et al. |
| 2009/0105338 | A1 | 4/2009 | Czarnik |
| 2009/0111840 | A1 | 4/2009 | Herold et al. |
| 2009/0118238 | A1 | 5/2009 | Czarnik |
| 2009/0131363 | A1 | 5/2009 | Harbeson |
| 2009/0131485 | A1 | 5/2009 | Liu et al. |
| 2009/0137457 | A1 | 5/2009 | Harbeson |
| 2009/0176785 | A1 | 7/2009 | Bardwell et al. |
| 2010/0152183 | A1 | 6/2010 | Bruncko et al. |
| 2010/0160322 | A1 | 6/2010 | Bruncko et al. |
| 2010/0184750 | A1 | 7/2010 | Hexamer et al. |
| 2010/0184766 | A1 | 7/2010 | Kunzer et al. |
| 2010/0240715 | A1 | 9/2010 | Bruncko et al. |

FOREIGN PATENT DOCUMENTS

| WO | WO 9507271 A1 | 3/1995 |
| WO | WO 971 0223 A1 | 3/1997 |
| WO | WO 02/24636 A2 | 3/2002 |
| WO | WO 2005024636 A1 | 3/2005 |
| WO | WO 2005049593 A2 | 6/2005 |
| WO | WO 2005099353 A2 | 10/2005 |
| WO | WO 2006008754 A1 | 1/2006 |
| WO | WO 2007/040650 A2 | 4/2007 |
| WO | WO 2009/036035 A1 | 3/2009 |

OTHER PUBLICATIONS

Beylot, M. et al., "In Vivo Studies of Intrahepatic Metabolic Pathways," Diabetes Metabolism, 1997, vol. 23 (3), pp. 251-257.
Blagojevic, N. et al., "Role of heavy water in Boron Neutron Capture Therapy," Topics in Dosimetry & Treatment Planninq for Neutron Capture Therapy, 1994, pp. 125-134.
Blake, M. I. et al., "Studies With Deuterated Drugs," Journal of Pharmaceutical Sciences, 1975, vol. 64 (3), pp. 367-391.
Brickner, S.J. et al., Journal of Medicinal Chemistry, 1996, vol. 39 (3), pp. 673-679.
Bruncko M., et al., "Studies Leading to Potent, Dual Inhibitors of Bcl-2 and Bcl-XL," Journal of Medicinal Chemistry, 2007, vol. 50 (4), pp. 641-662.
Cross, L.C. et al., "IUPAC Commission on Nomenclature of Organic Chemistry, Section E: Stereochemistry," Pure and Applied Chemistry, 1976, vol. 45, pp. 13-30.
Czajka, D. M. et al., "Effect of Deuterium Oxide on the Reproductive Potential of Mice," Annals of the New York Academy of Sciences, 1960, vol. 84, pp. 770-779.
Czajka, D. M. et al., "Physiological Effects of Deuterium on Dogs," American Journal of Physiology, 1961, vol. 201 (2), pp. 357-362.
Foster, A. B. et al., "Deuterium Isotope Effects in the Metabolism of Drugs and Xenobiotics: Implications for Drug Design," Advances in Drug Research, 1985, vol. 14, pp. 2-36.
Greene T.W., et al., Protective Groups in Organic Synthesis, 4th Edition, John Wiley and Sons, Inc., 2006, Table of Contents.

(Continued)

*Primary Examiner* — Rebecca Anderson
*Assistant Examiner* — Samantha Shterengarts
(74) *Attorney, Agent, or Firm* — Jones Day

(57) ABSTRACT

Disclosed are compounds which inhibit the activity of anti-apoptotic Bcl-2 proteins, compositions containing the compounds and methods of treating diseases during which is expressed anti-apoptotic Bcl-2 protein.

2 Claims, No Drawings

OTHER PUBLICATIONS

Holzelova, E. et al., "Autoimmune Lymphoproliferative Syndrome with Somatic Fas Mutations," New England Journal of Medicine, 2004, vol. 351 (14), pp. 1409-1418.

Kato, S. et al., "Synthesis of Deuterated Mosapride Citrate," Journal of Labelled Compounds and Radiopharmaceuticals, 1995, vol. 36 (10), pp. 927-932.

Korolkovas A., "Development of Drugs" in: Essentials of Medicinal Chemistry, Second Edition, John Wiley and Sons, 1988, pp. 97-118.

Kushner et al., "Pharmacological uses and perspectives of heavy water and deuterated compounds," Canadian Journal of Physiology and Pharmacology, 1999, vol. 77 (2), pp. 79-88.

Lizondo, J. et al., "Linezolid: Oxazolidinone antibacterial," Drugs of the Future, 1996, vol. 21 (11), pp. 1116-1123.

Mallesham, B. et al., Organic Letters, 2003, vol. 5 (7), pp. 963-965.

Park C.M., et al., Journal of Medicinal Chemistry, 2008, vol. 51(21), pp. 6902-6915.

Puck J.M., et al., "Immune Disorders Caused by Defects in the Caspase Cascade," Current Allergy and Asthma Reports, 2003, vol. 3, pp. 378-384.

Rengan R., et al., "Actin Cytoskeletal Function is Spared, but Apoptosis is Increased, in WAS Patient Hematopoietic Cells," Blood, 2000, vol. 95 (4), pp. 1283-1292.

Sattler M., et al., "Structure of Bcl-xL-Bak Peptide Complex: Recognition Between Regulators of Apoptosis," Science, 1997, vol. 275 (5302), pp. 983-986.

Shimazaki K., et al., "Evaluation of Apoptosis as a Prognostic Factor in Myelodysplastic Syndromes," British J Haematology, 2000, vol. 110 (3), pp. 584-590.

Soloway, Journal of Organic Chemistry, 1961, vol. 26, pp. 1091-1094.

Sutton, V.R. et al., Journal of Immunology, 1997, vol. 158 (12), pp. 5783-5790.

Thomson, J.F., "Physiological Effects of D20 in Mammals," Annals of the New York Academy of Sciences, 1960, vol. 84, pp. 736-744.

Tse, C. et al., "ABT-263: A Potent and Orally Bioavailable Bcl-2 Family Inhibitor," Cancer Research, 2008, vol. 68 (9), pp. 3421-3428—Including Supplementary Data.

Wendt et al., Journal of Medicial Chemistry, 2006, vol. 49, pp. 1165-1181.

ISA/EP, International Search Report dated Mar. 11, 2011 for PCT/US2011/027895.

Oltersdorf et al., "An inhibitor of Bcl-2 family proteins induces regression of solid tumors," Nature, 2005, vol. 435, pp. 677-681.

US 8,343,967 B2

APOPTOSIS-INDUCING AGENTS FOR THE TREATMENT OF CANCER AND IMMUNE AND AUTOIMMUNE DISEASES

This application is a divisional application of U.S. application Ser. No. 13/049,569, filed on Mar. 16, 2011, now U.S. Pat. No. 8,188,077 which claims benefit of U.S. Provisional Patent Application Ser. No. 61/317,575, filed on Mar. 25, 2010, both of which are incorporated herein by reference in their entireties.

FIELD OF THE INVENTION

This invention pertains to compounds which inhibit the activity of Bcl-2 anti-apoptotic proteins, compositions containing the compounds, and methods of treating diseases during which anti-apoptotic Bcl-2 proteins are expressed.

BACKGROUND OF THE INVENTION

Anti-apoptotic Bcl-2 proteins are associated with a number of diseases. There is therefore an existing need in the therapeutic arts for compounds which inhibit the activity of anti-apoptotic Bcl-2 proteins.

Overexpression of Bcl-2 proteins correlates with resistance to chemotherapy, clinical outcome, disease progression, overall prognosis or a combination thereof in various cancers and disorders of the immune system.

Involvement of Bcl-2 proteins in bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, spleen cancer, and the like is described in commonly-owned PCT US 2004/36770, published as WO 2005/049593, and PCT US 2004/37911, published as WO 2005/024636.

Involvement of Bcl-2 proteins in immune and autoimmune diseases is described in *Current Allergy and Asthma Reports* 2003, 3, 378-384; *British Journal of Haematology* 2000, 110(3), 584-90; *Blood* 2000, 95(4), 1283-92; and *New England Journal of Medicine* 2004, 351(14), 1409-1418. Involvement of Bcl-2 proteins in arthritis is disclosed in commonly-owned U.S. Provisional Patent Application Ser. No. 60/988,479. Involvement of Bcl-2 proteins in bone marrow transplant rejection is disclosed in commonly-owned U.S. patent application Ser. No. 11/941,196.

SUMMARY OF THE INVENTION

One embodiment of this invention pertains to compounds or therapeutically acceptable salts, prodrugs, metabolites, or salts of prodrugs thereof, which are useful as inhibitors of anti-apoptotic Bcl-2 proteins, the compounds chosen from
4-{4-[(4'-chlorobiphenyl-2-yl)methyl]piperazin-1-yl}-N-[(3-nitro-4-{[(1R,2R,3R,5S)-2,6,6-trimethylbicyclo[3.1.1]hept-3-yl]amino}phenyl)sulfonyl]benzamide;
4-(4-{acetyl[(1S,2S,3S,5R)-2,6,6-trimethylbicyclo[3.1.1]hept-3-yl]amino}piperidin-1-yl)-N-({4-[(cyclohexylmethyl)amino]-3-nitrophenyl}sulfonyl)benzamide;
4-(4-{benzoyl[(1S,2S,3S,5R)-2,6,6-trimethylbicyclo[3.1.1]hept-3-yl]amino}piperidin-1-yl)-N-({4-[(cyclohexylmethyl)amino]-3-nitrophenyl}sulfonyl)benzamide;

N-({4-[(cyclohexylmethyl)amino]-3-nitrophenyl}sulfonyl)-3'-{[(1S,2S,3S,5R)-2,6,6-trimethylbicyclo[3.1.1]hept-3-yl]amino}biphenyl-4-carboxamide;
N-({4-[(cyclohexylmethyl)amino]-3-nitrophenyl}sulfonyl)-4-(4-{(phenylacetyl)[(1S,2S,3S,5R)-2,6,6-trimethylbicyclo[3.1.1]hept-3-yl]amino}piperidin-1-yl)benzamide;
N-({4-[(cyclohexylmethyl)amino]-3-nitrophenyl}sulfonyl)-4'-[(1S,2S,3S,5R)-2,6,6-trimethylbicyclo[3.1.1]hept-3-yl]amino biphenyl-4-carboxamide;
N-({4-[(cyclohexylmethyl)amino]-3-nitrophenyl}sulfonyl)-4'-{(3-phenylpropyl)[(1S,2S,3S,5R)-2,6,6-trimethylbicyclo[3.1.1]hept-3-yl]amino}biphenyl-4-carboxamide;
4-{6-[adamantan-1-ylmethyl]-2,6-diazabicyclo[3.2.1]oct-2-yl}-N-({4-[(cyclohexylmethyl)amino]-3-nitrophenyl}sulfonyl)benzamide;
N-[(4-{[(2R)-4-(morpholin-4-yl)-1-(phenylthio)butan-2-yl]amino}-3-[(trifluoromethyl)sulfonyl]phenyl)sulfonyl]-4-(4-{(3-phenylpropanoyl)[(1S,2S,3S,5R)-2,6,6-trimethylbicyclo[3.1.1]hept-3-yl]amino}piperidin-1-yl)benzamide;
4-{4-[adamantan-1-ylmethyl]piperazin-1-yl}-N-[(4-{[(2R)-4-(morpholin-4-yl)-1-(phenylthio)butan-2-yl]amino}-3-nitrophenyl)sulfonyl]benzamide;
4-{(1S,4S)-5-[adamantan-1-ylmethyl]-2,5-diazabicyclo[2.2.1]hept-2-yl}-N-({4-[(cyclohexylmethyl)amino]-3-nitrophenyl}sulfonyl)benzamide;
4-(4-{[3-bromo-5-methyladamantan-1-yl]methyl}piperazin-1-yl)-N-({4-[(cyclohexylmethyl)amino]-3-nitrophenyl}sulfonyl)benzamide;
N-({4-[(cyclohexylmethyl)amino]-3-nitrophenyl}sulfonyl)-4-(4-{[3,5-dimethyladamantan-1-yl]methyl}piperazin-1-yl)benzamide;
4-{4-[(4'-chlorobiphenyl-2-yl)methyl]piperazin-1-yl}-N-{[4-(1-methyl-2-oxo-3-azabicyclo[3.1.1]hept-3-yl)phenyl]sulfonyl}benzamide;
N-({3-nitro-4-[(tetrahydro-2H-pyran-4-ylmethyl)amino]phenyl}sulfonyl)-4-(4-{2-[(1R,4R)-1,7,7-trimethylbicyclo[2.2.1]hept-2-en-2-yl]benzyl}piperazin-1-yl)benzamide;
N-({3-nitro-4-[(tetrahydro-2H-pyran-4-ylmethyl)amino]phenyl}sulfonyl)-4-(4-{2-octahydro-1H-4,7-methanoinden-5-ylamino]benzyl}piperazin-1-yl)benzamide;
N-({3-nitro-4-[(tetrahydro-2H-pyran-4-ylmethyl)amino]phenyl}sulfonyl)-4-[4-(2-{[(1R,4R,6S)-5,5,6-trimethylbicyclo[2.2.1]hept-2-yl]amino}benzyl)piperazin-1-yl]benzamide;
4-[4-(2-{[(1R,5S)-6,6-dimethylbicyclo[3.1.1]hept-2-yl]amino}benzyl)piperazin-1-yl]-N-({3-nitro-4-[(tetrahydro-2H-pyran-4-ylmethyl)amino]phenyl}sulfonyl)benzamide;
4-(4-{[(1R,5R)-2-(4-chlorophenyl)-6,6-dimethylbicyclo[3.1.1]hept-2-en-3-yl]methyl}piperazin-1-yl)-N-({-4-[(cyclohexylmethyl)amino]-3-nitrophenyl}sulfonyl)benzamide;
4-{4-[(2-{[adamantan-2-ylmethyl]amino}-5,5-dimethylcyclohexyl)methyl]piperazin-1-yl}-N-({3-nitro-4-[(tetrahydro-2H-pyran-4-ylmethyl)amino]phenyl}sulfonyl)benzamide;
4-{4-[(5,5-dimethyl-2-{[(1R,2S,3S,5S)-2,6,6-trimethylbicyclo[3.1.1]hept-3-yl]amino}cyclohexyl)methyl]piperazin-1-yl}-N-({3-nitro-4-[(tetrahydro-2H-pyran-4-ylmethyl)amino]phenyl}sulfonyl)benzamide;
4-{4-[2-(3-azabicyclo[3.2.2]non-3-yl)-5-nitrobenzyl]piperazin-1-yl}-N-({3-nitro-4-[(tetrahydro-2H-pyran-4-ylmethyl)amino]phenyl}sulfonyl)benzamide;

4-(4-{2-[2,3,3a,4,7,7a-hexahydro-1H-4,7-methanoinden-5-yl]benzyl}piperazin-1-yl)-N-({3-nitro-4-[(tetrahydro-2H-pyran-4-ylmethyl)amino]phenyl}sulfonyl)benzamide;

1-[adamantan-1-yl]-4-{2-[(4-{-4-[({3-nitro-4-[(tetrahydro-2H-pyran-4-ylmethyl)amino]phenyl}sulfonyl)carbamoyl]phenyl}piperazin-1-yl)methyl]phenyl}-N,N-diphenyl-1H-pyrazole-3-carboxamide;

4-(4-{2-[2-(adamantan-1-yl)-6-methylimidazo[1,2-a]pyridin-8-yl]benzyl}piperazin-1-yl)-N-({3-nitro-4-[(tetrahydro-2H-pyran-4-ylmethyl)amino]phenyl}sulfonyl)benzamide;

N-(adamantan-2-yl)-6-methyl-8-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}imidazo[1,2-a]pyridine-2-carboxamide;

4-(4-{2-[(1R,5S)-6,6-dimethylbicyclo[3.1.1]hept-2-en-2-yl]benzyl}piperazin-1-yl)-N-({3-nitro-4-[(tetrahydro-2H-pyran-4-ylmethyl)amino]phenyl}sulfonyl)benzamide;

N-({3-nitro-4-[(tetrahydro-2H-pyran-4-ylmethyl)amino]phenyl}sulfonyl)-4-(4-{2-[5,5,6-trimethylbicyclo[2.2.1]hept-2-en-2-yl]benzyl}piperazin-1-yl)benzamide;

N-cyclooctyl-5-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}-2-furamide;

N-benzyl-7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}bicyclo[2.2.1]hept-2-ene-1-carboxamide;

4-[4-(2-{[(1R,5S)-8-methyl-8-azabicyclo[3.2.1]oct-3-yl]amino}benzyl)piperazin-1-yl]-N-({3-nitro-4-[(tetrahydro-2H-pyran-4-ylmethyl)amino]phenyl}sulfonyl)benzamide;

N-({3-nitro-4-[(tetrahydro-2H-pyran-4-ylmethyl)amino]phenyl}sulfonyl)-4-[4-(2-{[(1R,2S,3S,5S)-2,6,6-trimethylbicyclo[3.1.1]hept-3-yl]amino}benzyl)piperazin-1-yl]benzamide;

4-(4-{2-[3-azabicyclo[3.2.2]non-3-yl]benzyl}piperazin-1-yl)-N-({3-nitro-4-[(tetrahydro-2H-pyran-4-ylmethyl)amino]phenyl}sulfonyl)benzamide;

N-({3-nitro-4-[(tetrahydro-2H-pyran-4-ylmethyl)amino]phenyl}sulfonyl)-4-(4-{2-[tricyclo[4.3.1.1$^{3,8}$]undec-4-en-4-yl]benzyl}piperazin-1-yl)benzamide;

7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}-N-phenylbicyclo[2.2.1]hept-2-ene-1-carboxamide;

7,7-dimethyl-2-{2-[(4-{-4-[({3-nitro-4-[(tetrahydro-2H-pyran-4-ylmethyl)amino]phenyl}sulfonyl)carbamoyl]phenyl}piperazin-1-yl)methyl]phenyl}-N-[(1S,2S,3S,5R)-2,6,6-trimethylbicyclo[3.1.1]hept-3-yl]bicyclo[2.2.1]hept-2-ene-1-carboxamide;

N-(adamantan-1-ylmethyl)-7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}bicyclo[2.2.1]hept-2-ene-1-carboxamide;

N-cyclopropyl-7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}bicyclo[2.2.1]hept-2-ene-1-carboxamide;

7,7-dimethyl-2-{2-[(4-{-4-[({3-nitro-4-[(tetrahydro-2H-pyran-4-ylmethyl)amino]phenyl}sulfonyl)carbamoyl]phenyl}piperazin-1-yl)methyl]phenyl}bicyclo[2.2.1]hept-2-ene-1-carboxylic;

4-[4-(2-{5-[8-azabicyclo[3.2.1]oct-8-ylmethyl]-2-thienyl}benzyl)piperazin-1-yl]-N-({3-nitro-4-[(tetrahydro-2H-pyran-4-ylmethyl)amino]phenyl}sulfonyl)benzamide;

4-{4-[adamantan-1-ylcarbonyl]piperazin-1-yl}-N-{[3-nitro-4-(tetrahydro-2H-pyran-4-ylamino)phenyl]sulfonyl}benzamide;

4-{4-[adamantan-2-ylcarbonyl]piperazin-1-yl}-N-{[3-nitro-4-(tetrahydro-2H-pyran-4-ylamino)phenyl]sulfonyl}benzamide;

4-{5-[adamantan-1-ylcarbonyl]-2,5-diazabicyclo[2.2.1]hept-2-yl}-N-{[3-nitro-4-(tetrahydro-2H-pyran-4-ylamino)phenyl]sulfonyl}benzamide;

4-{1S,5S}-3-[adamantan-1-ylcarbonyl]-3,6-diazabicyclo[3.2.0]hept-6-yl}-N-{[3-nitro-4-(tetrahydro-2H-pyran-4-ylamino)phenyl]sulfonyl}benzamide;

N-{[3-nitro-4-(tetrahydro-2H-pyran-4-ylamino)phenyl]sulfonyl}-4-(4-{(3-phenylpropyl)[(1S,2S,3S,5R)-2,6,6-trimethylbicyclo[3.1.1]hept-3-yl]amino}piperidin-1-yl)benzamide;

N-({4-[(cyclohexylmethyl)amino]-3-nitrophenyl}sulfonyl)-4-(4-{(3-phenylpropanoyl)[(1S,2S,3S,5R)-2,6,6-trimethylbicyclo[3.1.1]hept-3-yl]amino}piperidin-1-yl)benzamide;

4-{4-[adamantan-1-ylmethyl]piperazin-1-yl}-N-({4-[(cyclohexylmethyl)amino]-3-nitrophenyl}sulfonyl)benzamide;

6-{3-[adamantan-1-yl]-4-hydroxyphenyl}-N-({4-[(cyclohexylmethyl)amino]-3-nitrophenyl}sulfonyl)-2-naphthamide;

4-(4-{2-[adamantan-1-yl]-2-oxoethyl}piperazin-1-yl)-N-({4-[(cyclohexylmethyl)amino]-3-nitrophenyl}sulfonyl)benzamide;

4-{[adamantan-2-ylmethyl]amino}-N-{[3-nitro-4-(tetrahydro-2H-pyran-4-ylamino)phenyl]sulfonyl}benzamide;

4-{2-[adamantan-1-yl]ethoxy}-N-{[3-nitro-4-(tetrahydro-2H-pyran-4-ylamino)phenyl]sulfonyl}benzamide;

N$^3$-[adamantan-1-ylacetyl]-N$^3$-benzyl-N-({4-[(cyclohexylmethyl)amino]-3-nitrophenyl}sulfonyl)-beta-alaninamide;

N-({4-[(cyclohexylmethyl)amino]-3-nitrophenyl}sulfonyl)-4-{4-[(1S,2S,3S,5R)-2,6,6-trimethylbicyclo[3.1.1]hept-3-yl]piperazin-1-yl}benzamide;

4-{4-[adamantan-1-yl]piperazin-1-yl}-N-({4-[(cyclohexylmethyl)amino]-3-nitrophenyl}sulfonyl)benzamide;

N-({4-[(cyclohexylmethyl)amino]-3-nitrophenyl}sulfonyl)-4-{4-[3,5-dimethyladamantan-1-yl]piperazin-1-yl}benzamide;

[(3aS,5aR,8aR,8bS)-2,2,7,7-tetramethyltetrahydro-3aH-bis[1,3]dioxolo[4,5-b4',5'-d]pyran-3a-yl]methyl;

4-{4-[(4'-chlorobiphenyl-2-yl)methyl]piperazin-1-yl}-N-({[(1R,4S)-7,7-dimethyl-2-oxobicyclo[2.2.1]hept-1-yl]methyl}sulfonyl)benzamide;

4-(4-{2-[adamantan-1-yl]ethyl}piperazin-1-yl)-N-({4-[(cyclohexylmethyl)amino]-3-nitrophenyl}sulfonyl)benzamide;

4-{4-[(4'-chlorobiphenyl-2-yl)methyl]piperazin-1-yl}-N-({[(1S,4R)-7,7-dimethyl-2-oxobicyclo[2.2.1]hept-1-yl]methyl}sulfonyl)benzamide;

N-({-4-[(cyclohexylmethyl)amino]-3-nitrophenyl}sulfonyl)-4'-({(3-phenylpropanoyl)[(1S,2S,3S,5R)-2,6,6-trimethylbicyclo[3.1.1]hept-3-yl]amino}methyl)biphenyl-4-carboxamide;

N-({3-nitro-4-[(tetrahydro-2H-pyran-4-ylmethyl)amino]phenyl}sulfonyl)-4-(4-{2-[(1R,4R)-1,7,7-trimethylbicyclo[2.2.1]hept-2-en-2-yl]benzylidene}piperidin-1-yl)benzamide;

N-({3-nitro-4-[(tetrahydro-2H-pyran-4-ylmethyl)amino]phenyl}sulfonyl)-4-(4-{2-[5-(4-phenyl-1,3-thiazol-2-yl)-2-thienyl]benzyl}piperazin-1-yl)benzamide;

4-[4-(2-{5-[4-(adamantan-1-yl)-1,3-thiazol-2-yl]-2-thienyl}benzyl)piperazin-1-yl]-N-({3-nitro-4-[(tetrahydro-2H-pyran-4-ylmethyl)amino]phenyl}sulfonyl)benzamide;

5-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}-N-(2-phenyl-1,3-benzoxazol-5-yl)-2-furamide;

N-({3-nitro-4-[(tetrahydro-2H-pyran-4-ylmethyl)amino]phenyl}sulfonyl)-4-{4-[2-(triphenylvinyl)benzyl]piperazin-1-yl}benzamide;

4-{4-[2-(5-methyl-5,6-dihydrophenanthridin-6-yl)benzyl]piperazin-1-yl}-N-({3-nitro-4-[(tetrahydro-2H-pyran-4-ylmethyl)amino]phenyl}sulfonyl)benzamide;

N-({3-nitro-4-[(tetrahydro-2H-pyran-4-ylmethyl)amino]phenyl}sulfonyl)-4-{4-[2-(4,4,5,5-tetramethyl-1,3,2-dioxaborolan-2-yl)benzyl]piperazin-1-yl}benzamide;

4-(4-{2-[2-(2,6-dimethoxybenzoyl)-3-thienyl]benzylidene}piperidin-1-yl)-N-({3-nitro-4-[(tetrahydro-2H-pyran-4-ylmethyl)amino]phenyl}sulfonyl)benzamide;

1-[adamantan-1-yl]-4-{2-[(1-{-4-[({3-nitro-4-[(tetrahydro-2H-pyran-4-ylmethyl)amino]phenyl}sulfonyl)carbamoyl]phenyl}piperidin-4-ylidene)methyl]phenyl}-N,N-diphenyl-1H-pyrazole-3-carboxamide;

N-({3-nitro-4-[(tetrahydro-2H-pyran-4-ylmethyl)amino]phenyl}sulfonyl)-4-(4-{2-[octahydro-1H-4,7-methanoinden-5-yl(3-phenylpropanoyl)amino]benzyl}piperazin-1-yl)benzamide;

4-[4-(2-{5-[8-azabicyclo[3.2.1]oct-8-ylmethyl]-2-thienyl}benzylidene)piperidin-1-yl]-N-({3-nitro-4-[(tetrahydro-2H-pyran-4-ylmethyl)amino]phenyl}sulfonyl)benzamide;

N-({3-nitro-4-[(tetrahydro-2H-pyran-4-ylmethyl)amino]phenyl}sulfonyl)-4-[4-(4-{[(1S,2S,3S,5R)-2,6,6-trimethylbicyclo[3.1.1]hept-3-yl]amino}benzylidene)piperidin-1-yl]benzamide;

N-({3-nitro-4-[(tetrahydro-2H-pyran-4-ylmethyl)amino]phenyl}sulfonyl)-4-[4-(3-{[(1S,2S,3S,5R)-2,6,6-trimethylbicyclo[3.1.1]hept-3-yl]amino}benzylidene)piperidin-1-yl]benzamide;

4-[4-(2-{5-[4-(adamantan-1-yl)-1,3-thiazol-2-yl]-2-thienyl}benzylidene)piperidin-1-yl]-N-({3-nitro-4-[(tetrahydro-2H-pyran-4-ylmethyl)amino]phenyl}sulfonyl)benzamide;

N-({3-nitro-4-[(tetrahydro-2H-pyran-4-ylmethyl)amino]phenyl}sulfonyl)-4-(4-{2-[5-(4-phenyl-1,3-thiazol-2-yl)-2-thienyl]benzylidene}piperidin-1-yl)benzamide;

N-[(4-{[adamantan-1-ylmethyl]amino}-3-nitrophenyl)sulfonyl]-4-(4-oxo-4H-chromen-6-yl)benzamide;

N-[(4-{[adamantan-1-ylmethyl]amino}-3-nitrophenyl)sulfonyl]-4-(1-octyl-1H-pyrazol-4-yl)benzamide;

4-[5-(4-{[(4-{[adamantan-1-ylmethyl]amino}-3-nitrophenyl)sulfonyl]carbamoyl}phenyl)-1,3-benzothiazol-2-yl]butanoic;

N-{[3-nitro-4-(tetrahydro-2H-pyran-4-ylamino)phenyl]sulfonyl}-4-[(1R,5S)-1,8,8-trimethyl-3-azabicyclo[3.2.1]oct-3-yl]benzamide;

6-{3-[adamantan-1-yl]-4-methoxyphenyl}-N-({4-[(cyclohexylmethyl)amino]-3-nitrophenyl}sulfonyl)-2-naphthamide;

4-{4-[adamantan-1-ylacetyl]piperazin-1-yl}-N-{[3-nitro-4-(tetrahydro-2H-pyran-4-ylamino)phenyl]sulfonyl}benzamide;

4-{[adamantan-1-ylmethyl]amino}-N-{[3-nitro-4-(tetrahydro-2H-pyran-4-ylamino)phenyl]sulfonyl}benzamide;

N-{1-[4-({[3-nitro-4-(tetrahydro-2H-pyran-4-ylamino)phenyl]sulfonyl}carbamoyl)phenyl]piperidin-4-yl}adamantane-1-carboxamide;

4-[adamantan-2-ylamino]-N-{[3-nitro-4-(tetrahydro-2H-pyran-4-ylamino)phenyl]sulfonyl}benzamide; and N-{[3-nitro-4-(tetrahydro-2H-pyran-4-ylamino)phenyl]sulfonyl}-4-{[(1R,2R,3R,5S)-2,6,6-trimethylbicyclo[3.1.1]hept-3-yl]oxy}benzamide.

Another embodiment pertains to a composition for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer, said composition comprising an excipient and a therapeutically effective amount of a compound of this invention.

Another embodiment pertains to a method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said method comprising administering to the patient a therapeutically effective amount of a compound of this invention.

Another embodiment pertains to a method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said method comprising administering to the patient therapeutically effective amount of a compound of this invention and a therapeutically effective amount of one additional therapeutic agent or more than one additional therapeutic agent.

DETAILED DESCRIPTION OF THE INVENTION

Variable moieties herein are represented by identifiers (capital letters with numerical and/or alphabetical superscripts) and may be specifically embodied.

It is meant to be understood that proper valences are maintained for all moieties and combinations thereof, that monovalent moieties having more than one atom are drawn from left to right and are attached through their left ends, and that divalent moieties are also drawn from left to right.

It is also meant to be understood that a specific embodiment of a variable moiety herein may be the same or different as another specific embodiment having the same identifier.

The term "alkenyl" as used herein, means a straight or branched hydrocarbon chain containing from 2 to 10 carbons and containing at least one carbon-carbon double bond. The term "$C_x$-$C_y$ alkyl" means a straight or branched hydrocarbon chain containing at least one carbon-carbon double bond containing x to y carbon atoms. The term "$C_2$-$C_4$ alkenyl" means an alkenyl group containing 2-4 carbon atoms. Representative examples of alkenyl include, but are not limited to buta-2,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double bond. The term "$C_x$-$C_y$ alkylene" means a a divalent group derived from a straight or branched hydrocarbon chain containing at least one carbon-carbon double bond and containing x to y carbon atoms. Representative examples of alkenylene include, but are not limited to, —CH═CH— and —CH$_2$CH═CH—.

The term "alkyl" as used herein, means a straight or branched, saturated hydrocarbon chain containing from 1 to 10 carbon atoms. The term "$C_x$—$C_y$ alkyl" means a straight or branched chain, saturated hydrocarbon containing x to y carbon atoms. For example "$C_2$-$C_{10}$ alkyl" means a straight or branched chain, saturated hydrocarbon containing 2 to 10 carbon atoms. Examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched, saturated hydrocarbon chain of 1 to 10 carbon atoms, for example, of 1 to 4 carbon atoms. The term "$C_x$—$C_y$ alkylene" means a divalent group derived from a straight or branched chain, saturated hydrocarbon containing x to y carbon atoms. For example "$C_2$-$C_6$ alkylene" means a straight or branched chain, saturated hydrocarbon containing 2 to 6 carbon atoms. Examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. The term "$C_x$-$C_y$ alkynyl" means a straight or branched chain hydrocarbon group containing from x to y carbon atoms. Representative examples of alkynyl include, but are not limited, to acetylenyl, 1-propynyl, 2-propynyl, 3-butynyl, 2-pentynyl, and 1-butynyl.

The term "alkynylene," as used herein, means a divalent radical derived from a straight or branched chain hydrocarbon group containing from 2 to 10 carbon atoms and containing at least one carbon-carbon triple bond.

The term "aryl" as used herein, means phenyl.

The term "cyclic moiety," as used herein, means benzene, phenyl, phenylene, cycloalkane, cycloalkyl, cycloalkylene, cycloalkene, cycloalkenyl, cycloalkenylene, cycloalkyne, cycloalkynyl, cycloalkynylene, heteroarene, heteroaryl, heterocycloalkane, heterocycloalkyl, heterocycloalkene, heterocycloalkenyl and spiroalkyl.

The term "cycloalkylene" or cycloalkyl" or "cycloalkane" as used herein, means a monocyclic or bridged hydrocarbon ring system. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The monocyclic ring may contain one or two alkylene bridges, each consisting of one, two, or three carbon atoms, each linking two non-adjacent carbon atoms of the ring system. Non-limiting examples of such bridged cycloalkyl ring systems include bicyclo[3.1.1] heptane, bicyclo[2.2.1]heptane, bicyclo[2.2.2]octane, bicyclo[3.2.2]nonane, bicyclo[3.3.1]nonane, bicyclo[4.2.1] nonane, tricyclo[3.3.1.0$^{3,7}$]nonane (octahydro-2,5-methanopentalene or noradamantane), and tricyclo[3.3.1.1$^{3,7}$]decane (adamantane). The monocyclic and bridged cycloalkyl can be attached to the parent molecular moiety through any substitutable atom contained within the ring system.

The term "cycloalkenylene," or "cycloalkenyl" or "cycloalkene" as used herein, means a monocyclic or a bridged hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The monocyclic cycloalkenyl ring may contain one or two alkylene bridges, each consisting of one, two, or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyl can be attached to the parent molecular moiety through any substitutable atom contained within the ring systems.

The term "cycloalkyne," or "cycloalkynyl," or "cycloalkynylene," as used herein, means a monocyclic or a bridged hydrocarbon ring system. The monocyclic cycloalkynyl has eight or more carbon atoms, zero heteroatoms, and one or more triple bonds. The monocyclic cycloalkynyl ring may contain one or two alkylene bridges, each consisting of one, two, or three carbon atoms, each linking two non-adjacent carbon atoms of the ring system. The monocyclic and bridged cycloalkynyl can be attached to the parent molecular moiety through any substitutable atom contained within the ring systems.

The term "heteroarene," or "heteroaryl," or "heteroarylene," as used herein, means a five-membered or six-membered aromatic ring having at least one carbon atom and one or more than one independently selected nitrogen, oxygen or sulfur atom. The heteroarenes of this invention are connected through any adjacent atoms in the ring, provided that proper valences are maintained. Representative examples of heteroaryl include, but are not limited to, furanyl (including, but not limited thereto, furan-2-yl), imidazolyl (including, but not limited thereto, 1H-imidazol-1-yl), isoxazolyl, isothiazolyl, oxadiazolyl, oxazolyl, pyridinyl (e.g. pyridin-4-yl, pyridin-2-yl, pyridin-3-yl), pyridazinyl, pyrimidinyl, pyrazinyl, pyrazolyl, pyrrolyl, tetrazolyl, thiadiazolyl, thiazolyl, thienyl (including, but not limited thereto, thien-2-yl, thien-3-yl), triazolyl, and triazinyl.

The term "heterocycloalkane," or "heterocycloalkyl," or "heterocycloalkylene," as used herein, means monocyclic or bridged three-, four-, five-, six-, seven-, or eight-membered ring containing at least one heteroatom independently selected from the group consisting of O, N, and S and zero double bonds. The monocyclic and bridged heterocycloalkane are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quarternized. Representative examples of heterocycloalkane groups include, but are not limited to, Representative examples of heterocycloalkane groups include, but are not limited to, morpholinyl, tetrahydropyranyl, pyrrolidinyl, piperidinyl, dioxolanyl, tetrahydrofuranyl, thiomorpholinyl, dioxanyl, tetrahydrothienyl, tetrahydrothiopyranyl, oxetanyl, piperazinyl, imidazolidinyl, azetidine, azepanyl, aziridinyl, diazepanyl, dithiolanyl, dithianyl, isoxazolidinyl, isothiazolidinyl, oxadiazolidinyl, oxazolidinyl, pyrazolidinyl, tetrahydrothienyl, thiadiazolidinyl, thiazolidinyl, thiomorpholinyl, trithianyl, and trithianyl.

The term "heterocycloalkene," or "heterocycloalkenyl," or "heterocycloalkenylene," as used herein, means monocyclic or bridged three-, four-, five-, six-, seven-, or eight-membered ring containing at least one heteroatom independently selected from the group consisting of O, N, and S and one or more double bonds. The monocyclic and bridged heterocycloalkene are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quarternized. Representative examples of heterocycloalkene groups include, but are not limited to, tetrahydrooxocinyl, 1,4,5,6-tetrahydropyridazinyl, 1,2,3,6-tetrahydropyridinyl, dihydropyranyl, imidazolinyl, isothiazolinyl, oxadiazolinyl, isoxazolinyl, oxazolinyl, pyranyl, pyrazolinyl, pyrrolinyl, thiadiazolinyl, thiazolinyl, and thiopyranyl.

The term "phenylene," as used herein, means a divalent radical formed by removal of a hydrogen atom from phenyl.

The term "spiroalkyl," as used herein, means alkylene, both ends of which are attached to the same carbon atom and is exemplified by $C_2$-spiroalkyl, $C_3$-spiroalkyl, $C_4$-spiroalkyl, $C_5$-spiroalkyl, $C_6$-spiroalkyl, $C_7$-spiroalkyl, $C_8$-spiroalkyl, $C_9$-spiroalkyl and the like.

The term "spiroheteroalkyl," as used herein, means spiroalkyl having one or two $CH_2$ moieties replaced with independently selected O, C(O), CNOH, $CNOCH_3$, S, S(O), $SO_2$ or NH and one or two CH moieties unreplaced or replaced with N.

The term "spiroheteroalkenyl," as used herein, means spiroalkenyl having one or two $CR_2$ moieties replaced with independently selected O, C(O), CNOH, $CNOCH_3$, S, S(O), $SO_2$ or NH and one or two CH moieties unreplaced or replaced with N and also means spiroalkenyl having one or two $CH_2$ moieties unreplaced or replaced with independently selected O, C(O), CNOH, $CNOCH_3$, S, S(O), $SO_2$ or NH and one or two CH moieties replaced with N.

The term, "spirocyclo," as used herein, means two substituents on the same carbon atom, that, together with the carbon atom to which they are attached, form a cycloalkane, heterocycloalkane, cycloalkene, or heterocycloalkene ring.

The term "$C_2$-$C_5$-spiroalkyl," as used herein, means $C_2$-spiroalkyl, $C_3$-spiroalkyl, $C_4$-spiroalkyl, and $C_5$-spiroalkyl.

The term "$C_2$-spiroalkyl," as used herein, means eth-1,2-ylene, both ends of which replace hydrogen atoms of the same $CH_2$ moiety.

The term "$C_3$-spiroalkyl," as used herein, means prop-1,3-ylene, both ends of which replace hydrogen atoms of the same $CH_2$ moiety.

The term "$C_4$-spiroalkyl," as used herein, means but-1,4-ylene, both ends of which replace hydrogen atoms of the same $CH_2$ moiety.

The term "$C_5$-spiroalkyl," as used herein, means pent-1,5-ylene, both ends of which replace hydrogen atoms of the same $CH_2$ moiety.

The term "$C_6$-spiroalkyl," as used herein, means hex-1,6-ylene, both ends of which replace hydrogen atoms of the same $CH_2$ moiety.

The term "NH protecting group," as used herein, means a substituent that protects NH groups against undesirable reactions during synthetic procedures. Examples of NH protecting groups include, but are not limited to, trichloroethoxycarbonyl, tribromoethoxycarbonyl, benzyloxycarbonyl, para-nitrobenzylcarbonyl, ortho-bromobenzyloxycarbonyl, chloroacetyl, dichloroacetyl, trichloroacetyl, trifluoroacetyl, phenylacetyl, formyl, acetyl, benzoyl, tert-amyloxycarbonyl, tert-butoxycarbonyl, para-methoxybenzyloxycarbonyl, 3,4-dimethoxybenzyl-oxycarbonyl, 4-(phenylazo)benzyloxycarbonyl, 2-furfuryl-oxycarbonyl, diphenylmethoxycarbonyl, 1,1-dimethylpropoxy-carbonyl, isopropoxycarbonyl, phthaloyl, succinyl, alanyl, leucyl, 1-adamantyloxycarbonyl, 8-quinolyloxycarbonyl, benzyl, diphenylmethyl, triphenylmethyl, 2-nitrophenylthio, methanesulfonyl, para-toluencsulfonyl, N,N-dimethylaminomethylene, benzylidene, 2-hydroxybenzylidene, 2-hydroxy-5-chlorobenzylidene, 2-hydroxy-1-naphthyl-methylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclo-hexylidene, diphenylphosphoryl, dibenzylphosphoryl, 5-methyl-2-oxo-2H-1,3-dioxol-4-yl-methyl, trimethylsilyl, triethylsilyl, and triphenylsilyl.

The term "C(O)OH protecting group," as used herein, means a substituent that protects C(O)OH groups against undesirable reactions during synthetic procedures. Examples of C(O)OH protecting groups include, but are not limited to, methyl, ethyl, n-propyl, isopropyl, 1,1-dimethylpropyl, n-butyl, tert-butyl, phenyl, naphthyl, benzyl, diphenylmethyl, triphenylmethyl, para-nitrobenzyl, para-methoxybenzyl, bis(para-methoxyphenyl)methyl, acetylmethyl, benzoylmethyl, para-nitrobenzoylmethyl, para-bromobenzoylmethyl, para-methanesulfonylbenzoylmethyl, 2-tetrahydropyranyl 2-tetrahydrofuranyl, 2,2,2-tri chloro-ethyl, 2-(trimethylsilyl)ethyl, acetoxymethyl, propionyloxymethyl, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl)ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

The term "OH or SH protecting group," as used herein, means a substituent that protects OH or SH groups against undesirable reactions during synthetic procedures. Examples of OH or SH protecting groups include, but are not limited to, benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethylsilylethyl, 1,1-dimethyl-2-propenyl, 3-methyl-3-butenyl, allyl, benzyl (phenylmethyl), para-methoxybenzyl, 3,4-dimethoxybenzyl, diphenylmethyl, triphenylmethyl, tetrahydrofuryl, tetrahydropyranyl, tetrahydrothiopyranyl, methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, methanesulfonyl, para-toluenesulfonyl, trimethylsilyl, triethylsilyl, triisopropylsilyl, diethylisopropylsilyl, tert-butyldimethylsilyl, tort-butyldiphenylsilyl, diphenylmethylsilyl, and tort-butylmethoxyphenylsilyl.

For a review of protecting groups in organic synthesis, see Greene, T. W.; Wuts, P. G. M. *Protective Groups in Organic Synthesis,* 4th ed., Wiley-Interscience: New York, 2006.

Compounds

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are designated as being of cis or trans configuration.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Compounds of this invention containing NH, C(O)OH, OH or SH moieties may have attached thereto prodrug-forming moieties. The prodrug-forming moieties are removed by metabolic processes and release the compounds having the freed hydroxyl, amino or carboxylic acid in vivo. Prodrugs are useful for adjusting such pharmacokinetic properties of the compounds as solubility and/or hydrophobicity, absorption in the gastrointestinal tract, bioavailability, tissue penetration, and rate of clearance.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to $^2H$, $^3H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^2H$), tritium ($^3H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. In addition to the above, relevant procedures and intermediates are disclosed, for instance, in Lizondo, J et al., *Drugs Fut,* 21(11), 1116 (1996); Brickner, S J et al., *J Med Chem,* 39(3), 673 (1996); Mallesham, B et al., *Org Lett,* 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of Bcl-2 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.,* 36(10):927-932 (1995); Kushner et al., *Can. J. Physiol. Pharmacol.,* 77, 79-88 (1999)).

In addition, non-radio active isotope containing drugs, such as deuterated drugs called "heavy drugs," can be used for the treatment of diseases and conditions related to Bcl-2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 25-134; Diabetes Metab. 23: 251 (1997)).

Stable isotope labeling of a drug can alter its physico-chemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmcokinetic profile or efficacy relative to the non-istopic compound.

Amides, Esters and Prodrugs

Prodrugs are derivatives of an active drug designed to ameliorate some identified, undesirable physical or biological property. The physical properties are usually solubility (too much or not enough lipid or aqueous solubility) or stability related, while problematic biological properties include too rapid metabolism or poor bioavailability which itself may be related to a physicochemical property.

Prodrugs are usually prepared by: a) formation of ester, hemi esters, carbonate esters, nitrate esters, amides, hydroxamic acids, carbamates, imines, Mannich bases, phosphates, phosphate esters, and enamines of the active drug, b) functionalizing the drug with azo, glycoside, peptide, and ether functional groups, c) use of aminals, hemi-aminals, polymers, salts, complexes, phosphoramides, acetals, hemiacetals, and ketal forms of the drug. For example, see Andrejus Korolkovas's, "Essentials of Medicinal Chemistry", John Wiley-Interscience Publications, John Wiley and Sons, New York (1988), pp. 97-118, which is incorporated in its entirety by reference herein.

Esters can be prepared from substrates of formula (I) containing either a hydroxyl group or a carboxy group by general methods known to persons skilled in the art. The typical reactions of these compounds are substitutions replacing one of the heteroatoms by another atom, for example:

Scheme 1

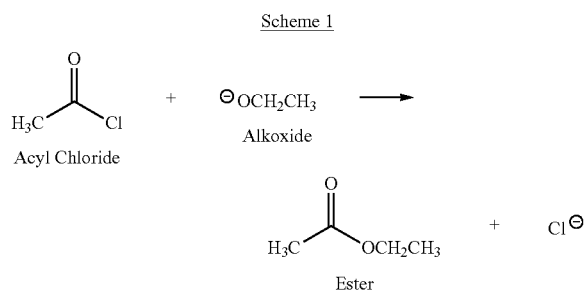

Amides can be prepared from substrates of formula (I) containing either an amino group or a carboxy group in similar fashion. Esters can also react with amines or ammonia to form amides.

Scheme 2

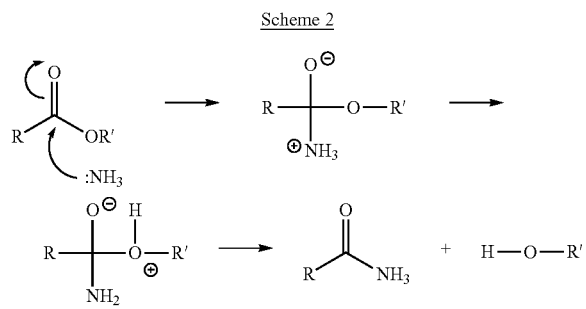

Another way to make amides from compounds of formula (I) is to heat carboxylic acids and amines together.

Scheme 3

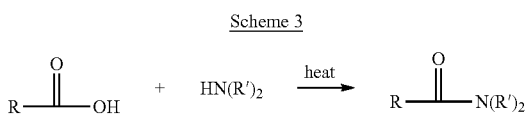

In Schemes 2 and 3 above, R and R' are independently substrates of formula (I), alkyl or hydrogen.

One embodiment of this invention pertains to compounds or therapeutically acceptable salts, prodrugs, metabolites, or salts of prodrugs thereof, which are useful as inhibitors of anti-apoptotic Bcl-2 proteins, the compounds chosen from 4-{4-[(4'-chlorobiphenyl-2-yl)methyl]piperazin-1-yl}-N-[(3-nitro-4-{[(1R,2R,3R,5S)-2,6,6-trimethylbicyclo[3.1.1]hept-3-yl]amino}phenyl)sulfonyl]benzamide;

4-(4-{acetyl[(1S,2S,3S,5R)-2,6,6-trimethylbicyclo[3.1.1]hept-3-yl]amino}piperidin-1-yl)-N-({4-[(cyclohexylmethyl)amino]-3-nitrophenyl}sulfonyl)benzamide;

4-(4-{benzoyl[(1S,2S,3S,5R)-2,6,6-trimethylbicyclo[3.1.1]hept-3-yl]amino}piperidin-1-yl)-N-({4-[(cyclohexylmethyl)amino]-3-nitrophenyl}sulfonyl)benzamide;

N-({4-[(cyclohexylmethyl)amino]-3-nitrophenyl}sulfonyl)-3'-{[(1S,2S,3S,5R)-2,6,6-trimethylbicyclo[3.1.1]hept-3-yl]amino}biphenyl-4-carboxamide;

N-({4-[(cyclohexylmethyl)amino]-3-nitrophenyl}sulfonyl)-4-(4-{(phenylacetyl)[(1S,2S,3S,5R)-2,6,6-trimethylbicyclo[3.1.1]hept-3-yl]amino}piperidin-1-yl)benzamide;

N-({4-[(cyclohexylmethyl)amino]-3-nitrophenyl}sulfonyl)-4'-{[(1S,2S,3S,5R)-2,6,6-trimethylbicyclo[3.1.1]hept-3-yl]amino}biphenyl-4-carboxamide;

N-({4-[(cyclohexylmethyl)amino]-3-nitrophenyl}sulfonyl)-4'-{(3-phenylpropyl)[(1S,2S,3S,5R)-2,6,6-trimethylbicyclo[3.1.1]hept-3-yl]amino}biphenyl-4-carboxamide;

4-{6-[adamantan-1-ylmethyl]-2,6-diazabicyclo[3.2.1]oct-2-yl}-N-({4-[(cyclohexylmethyl)amino]-3-nitrophenyl}sulfonyl)benzamide;

N-[(4-{[(2R)-4-(morpholin-4-yl)-1-(phenylthio)butan-2-yl]amino}-3-[(trifluoromethyl)sulfonyl]phenyl)sulfonyl]-4-(4-{(3-phenylpropanoyl)[(1S,2S,3S,5R)-2,6,6-trimethylbicyclo[3.1.1]hept-3-yl]amino}piperidin-1-yl)benzamide;

4-{4-[adamantan-1-ylmethyl]piperazin-1-yl}-N-[(4-{[(2R)-4-(morpholin-4-yl)-1-(phenylthio)butan-2-yl]amino}-3-nitrophenyl)sulfonyl]benzamide;

4-{(1S,4S)-5-[adamantan-1-ylmethyl]-2,5-diazabicyclo[2.2.1]hept-2-yl}-N-({4-[(cyclohexylmethyl)amino]-3-nitrophenyl}sulfonyl)benzamide;

4-(4-{[3-bromo-5-methyladamantan-1-yl]methyl}piperazin-1-yl)-N-({4-[(cyclohexylmethyl)amino]-3-nitrophenyl}sulfonyl)benzamide;

N-({4-[(cyclohexylmethyl)amino]-3-nitrophenyl}sulfonyl)-4-(4-{[3,5-dimethyladamantan-1-yl]methyl}piperazin-1-yl)benzamide;

4-{4-[(4'-chlorobiphenyl-2-yl)methyl]piperazin-1-yl}-N-{[4-(1-methyl-2-oxo-3-azabicyclo[3.1.1]hept-3-yl)phenyl]sulfonyl}benzamide;

N-({3-nitro-4-[(tetrahydro-2H-pyran-4-ylmethyl)amino]phenyl}sulfonyl)-4-(4-{2-[(1R,4R)-1,7,7-trimethylbicyclo[2.2.1]hept-2-en-2-yl]benzyl}piperazin-1-yl)benzamide;

N-({3-nitro-4-[(tetrahydro-2H-pyran-4-ylmethyl)amino]phenyl}sulfonyl)-4-(4-{2-octahydro-1H-4,7-methanoinden-5-ylamino]benzyl}piperazin-1-yl)benzamide;

N-({3-nitro-4-[(tetrahydro-2H-pyran-4-ylmethyl)amino]phenyl}sulfonyl)-4-[4-(2-{[(1R,4R,6S)-5,5,6-trimethylbicyclo[2.2.1]hept-2-yl]amino}benzyl)piperazin-1-yl]benzamide;

4-[4-(2-{[(1R,5S)-6,6-dimethylbicyclo[3.1.1]hept-2-yl]amino}benzyl)piperazin-1-yl]-N-({3-nitro-4-[(tetrahydro-2H-pyran-4-ylmethyl)amino]phenyl}sulfonyl)benzamide;

4-(4-{[(1R,5R)-2-(4-chlorophenyl)-6,6-dimethylbicyclo[3.1.1]hept-2-en-3-yl]methyl}piperazin-1-yl)-N-({-4-[(cyclohexylmethyl)amino]-3-nitrophenyl}sulfonyl)benzamide;

4-{4-[(2-{[adamantan-2-ylmethyl]amino}-5,5-dimethylcyclohexyl)methyl]piperazin-1-yl}-N-({3-nitro-4-[(tetrahydro-2H-pyran-4-ylmethyl)amino]phenyl}sulfonyl)benzamide;

4-{4-[(5,5-dimethyl-2-{[(1R,2S,3S,5S)-2,6,6-trimethylbicyclo[3.1.1]hept-3-yl]amino}cyclohexyl)methyl]piperazin-1-yl}-N-({3-nitro-4-[(tetrahydro-2H-pyran-4-ylmethyl)amino]phenyl}sulfonyl)benzamide;

4-{4-[2-(3-azabicyclo[3.2.2]non-3-yl)-5-nitrobenzyl]piperazin-1-yl}-N-({3-nitro-4-[(tetrahydro-2H-pyran-4-ylmethyl)amino]phenyl}sulfonyl)benzamide;

4-(4-{2-[2,3,3a,4,7,7a-hexahydro-1H-4,7-methanoinden-5-yl]benzyl}piperazin-1-yl)-N-({3-nitro-4-[(tetrahydro-2H-pyran-4-ylmethyl)amino]phenyl}sulfonyl)benzamide;

1-[adamantan-1-yl]-4-{2-[(4-{-4-[({3-nitro-4-[(tetrahydro-2H-pyran-4-ylmethyl)amino]phenyl}sulfonyl)carbamoyl]phenyl}piperazin-1-yl)methyl]phenyl}-N,N-diphenyl-1H-pyrazole-3-carboxamide;

4-(4-{2-[2-(adamantan-1-yl)-6-methylimidazo[1,2-a]pyridin-8-yl]benzyl}piperazin-1-yl)-N-({3-nitro-4-[(tetrahydro-2H-pyran-4-ylmethyl)amino]phenyl}sulfonyl)benzamide;

N-(adamantan-2-yl)-6-methyl-8-{2-[(4-{-4-[({3-nitro-4-[(tetrahydro-2H-pyran-4-ylmethyl)amino]phenyl}sulfonyl)carbamoyl]phenyl}piperazin-1-yl)methyl]phenyl}imidazo[1,2-a]pyridine-2-carboxamide;

4-(4-{2-[(1R,5S)-6,6-dimethylbicyclo[3.1.1]hept-2-en-2-yl]benzyl}piperazin-1-yl)-N-({3-nitro-4-[(tetrahydro-2H-pyran-4-ylmethyl)amino]phenyl}sulfonyl)benzamide;

N-({3-nitro-4-[(tetrahydro-2H-pyran-4-ylmethyl)amino]phenyl}sulfonyl)-4-(4-{2-[5,5,6-trimethylbicyclo[2.2.1]hept-2-en-2-yl]benzyl}piperazin-1-yl)benzamide;

N-cyclooctyl-5-{2-[(4-{-4-[({3-nitro-4-[(tetrahydro-2H-pyran-4-ylmethyl)amino]phenyl}sulfonyl)carbamoyl]phenyl}piperazin-1-yl)methyl]phenyl}-2-furamide;

N-benzyl-7,7-dimethyl-2-{2-[(4-{-4-[({3-nitro-4-[(tetrahydro-2H-pyran-4-ylmethyl)amino]phenyl}sulfonyl)carbamoyl]phenyl}piperazin-1-yl)methyl]phenyl}bicyclo[2.2.1]hept-2-ene-1-carboxamide;

4-[4-(2-{[(1R,5S)-8-methyl-8-azabicyclo[3.2.1]oct-3-yl]amino}benzyl)piperazin-1-yl]-N-({3-nitro-4-[(tetrahydro-2H-pyran-4-ylmethyl)amino]phenyl}sulfonyl)benzamide;

N-({3-nitro-4-[(tetrahydro-2H-pyran-4-ylmethyl)amino]phenyl}sulfonyl)-4-[4-(2-{[(1R,2S,3S,5S)-2,6,6-trimethylbicyclo[3.1.1]hept-3-yl]amino}benzyl)piperazin-1-yl]benzamide;

4-(4-{2-[3-azabicyclo[3.2.2]non-3-yl]benzyl}piperazin-1-yl)-N-({3-nitro-4-[(tetrahydro-2H-pyran-4-ylmethyl)amino]phenyl}sulfonyl)benzamide;

N-({3-nitro-4-[(tetrahydro-2H-pyran-4-ylmethyl)amino]phenyl}sulfonyl)-4-(4-{2-[tricyclo[4.3.1.1$^{3,8}$]undec-4-en-4-yl]benzyl}piperazin-1-yl)benzamide;

7,7-dimethyl-2-{2-[(4-{-4-[({3-nitro-4-[(tetrahydro-2H-pyran-4-ylmethyl)amino]phenyl}sulfonyl)carbamoyl]phenyl}piperazin-1-yl)methyl]phenyl}-N-phenylbicyclo[2.2.1]hept-2-ene-1-carboxamide;

7,7-dimethyl-2-{2-[(4-{-4-[({3-nitro-4-[(tetrahydro-2H-pyran-4-ylmethyl)amino]phenyl}sulfonyl)carbamoyl]phenyl}piperazin-1-yl)methyl]phenyl}-N-[(1S,2S,3S,5R)-2,6,6-trimethylbicyclo[3.1.1]hept-3-yl]bicyclo[2.2.1]hept-2-ene-1-carboxamide;

N-(adamantan-1-ylmethyl)-7,7-dimethyl-2-{2-[(4-{-4-[({3-nitro-4-[(tetrahydro-2H-pyran-4-ylmethyl)amino]phenyl}sulfonyl)carbamoyl]phenyl}piperazin-1-yl)methyl]phenyl}bicyclo[2.2.1]hept-2-ene-1-carboxamide;

N-cyclopropyl-7,7-dimethyl-2-{2-[(4-{-4-[({3-nitro-4-[(tetrahydro-2H-pyran-4-ylmethyl)amino]phenyl}sulfonyl)carbamoyl]phenyl}piperazin-1-yl)methyl]phenyl}bicyclo[2.2.1]hept-2-ene-1-carboxamide;

7,7-dimethyl-2-{2-[(4-{-4-[({3-nitro-4-[(tetrahydro-2H-pyran-4-ylmethyl)amino]phenyl}sulfonyl)carbamoyl]phenyl}piperazin-1-yl)methyl]phenyl}bicyclo[2.2.1]hept-2-ene-1-carboxylic;

4-[4-(2-{5-[8-azabicyclo[3.2.1]oct-8-ylmethyl]-2-thienyl}benzyl)piperazin-1-yl]-N-({3-nitro-4-[(tetrahydro-2H-pyran-4-ylmethyl)amino]phenyl}sulfonyl)benzamide;

4-{4-[adamantan-1-ylcarbonyl]piperazin-1-yl}-N-{[3-nitro-4-(tetrahydro-2H-pyran-4-ylamino)phenyl]sulfonyl}benzamide;

4-{4-[adamantan-2-ylcarbony]piperazin-1-yl}-N-{[3-nitro-4-(tetrahydro-2H-pyran-4-ylamino)phenyl]sulfonyl}benzamide;

4-{5-[adamantan-1-ylcarbonyl]-2,5-diazabicyclo[2.2.1]hept-2-yl}-N-{[3-nitro-4-(tetrahydro-2H-pyran-4-ylamino)phenyl]sulfonyl}benzamide;

4-{1S,5S}-3-[adamantan-1-ylcarbonyl]-3,6-diazabicyclo[3.2.0]hept-6-yl}-N-{[3-nitro-4-(tetrahydro-2H-pyran-4-ylamino)phenyl]sulfonyl}benzamide;

N-{[3-nitro-4-(tetrahydro-2H-pyran-4-ylamino)phenyl]sulfonyl}-4-(4-{(3-phenylpropyl)[(1S,2S,3S,5R)-2,6,6-trimethylbicyclo[3.1.1]hept-3-yl]amino}piperidin-1-yl)benzamide;

N-({4-[(cyclohexylmethyl)amino]-3-nitrophenyl}sulfonyl)-4-(4-{(3-phenylpropanoyl)[(1S,2S,3S,5R)-2,6,6-trimethylbicyclo[3.1.1]hept-3-yl]amino}piperidin-1-yl)benzamide;

4-{4-[adamantan-1-ylmethyl]piperazin-1-yl}-N-({4-[(cyclohexylmethyl)amino]-3-nitrophenyl}sulfonyl)benzamide;

6-{3-[adamantan-1-yl]-4-hydroxyphenyl}-N-({4-[(cyclohexylmethyl)amino]-3-nitrophenyl}sulfonyl)-2-naphthamide;

4-(4-{2-[adamantan-1-yl]-2-oxoethyl}piperazin-1-yl)-N-({4-[(cyclohexylmethyl)amino]-3-nitrophenyl}sulfonyl)benzamide;

4-{[adamantan-2-ylmethyl]amino}-N-{[3-nitro-4-(tetrahydro-2H-pyran-4-ylamino)phenyl]sulfonyl}benzamide;

4-{2-[adamantan-1-yl]ethoxy}-N-{[3-nitro-4-(tetrahydro-2H-pyran-4-ylamino)phenyl]sulfonyl}benzamide;

N$^3$-[adamantan-1-ylacetyl]-N$^3$-benzyl-N-({4-[(cyclohexylmethyl)amino]-3-nitrophenyl}sulfonyl)-beta-alaninamide;

N-({4-[(cyclohexylmethyl)amino]-3-nitrophenyl}sulfonyl)-4-{4-[(1S,2S,3S,5R)-2,6,6-trimethylbicyclo[3.1.1]hept-3-yl]piperazin-1-yl}benzamide;

4-{4-[adamantan-1-yl]piperazin-1-yl}-N-({4-[(cyclohexylmethyl)amino]-3-nitrophenyl}sulfonyl)benzamide;

N-({4-[(cyclohexylmethyl)amino]-3-nitrophenyl}sulfonyl)-4-{4-[3,5-dimethyladamantan-1-yl]piperazin-1-yl}benzamide;

[(3aS,5aR,8aR,8bS)-2,2,7,7-tetramethyltetrahydro-3 aH-bis[1,3]dioxolo[4,5-b4',5'-d]pyran-3a-yl]methyl;

4-{4-[(4'-chlorobiphenyl-2-yl)methyl]piperazin-1-yl}-N-({[(1R,4S)-7,7-dimethyl-2-oxobicyclo[2.2.1]hept-1-yl]methyl}sulfonyl)benzamide;

4-(4-{2-[adamantan-1-yl]ethyl}piperazin-1-yl)-N-({4-[(cyclohexylmethyl)amino]-3-nitrophenyl}sulfonyl)benzamide;

4-{4-[(4'-chlorobiphenyl-2-yl)methyl]piperazin-1-yl}-N-({[(1S,4R)-7,7-dimethyl-2-oxobicyclo[2.2.1]hept-1-yl]methyl}sulfonyl)benzamide;

N-({-4-[(cyclohexylmethyl)amino]-3-nitrophenyl}sulfonyl)-4'-({(3-phenylpropanoyl)[(1S,2S,3S,5R)-2,6,6-trimethylbicyclo[3.1.1]hept-3-yl]amino}methyl)biphenyl-4-carboxamide;

N-({3-nitro-4-[(tetrahydro-2H-pyran-4-ylmethyl)amino]phenyl}sulfonyl)-4-(4-{2-[(1R,4R)-1,7,7-trimethylbicyclo[2.2.1]hept-2-en-2-yl]benzylidene}piperidin-1-yl)benzamide;

N-({3-nitro-4-[(tetrahydro-2H-pyran-4-ylmethyl)amino]phenyl}sulfonyl)-4-(4-{2-[5-(4-phenyl-1,3-thiazol-2-yl)-2-thienyl]benzyl}piperazin-1-yl)benzamide;

4-[4-(2-{5-[4-(adamantan-1-yl)-1,3-thiazol-2-yl]-2-thienyl}benzyl)piperazin-1-yl]-N-({3-nitro-4-[(tetrahydro-2H-pyran-4-ylmethyl)amino]phenyl}sulfonyl)benzamide;

5-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}-N-(2-phenyl-1,3-benzoxazol-5-yl)-2-furamide;

N-({3-nitro-4-[(tetrahydro-2H-pyran-4-ylmethyl)amino]phenyl}sulfonyl)-4-{4-[2-(triphenylvinyl)benzyl]piperazin-1-yl}benzamide;

4-{4-[2-(5-methyl-5,6-dihydrophenanthridin-6-yl)benzyl]piperazin-1-yl}-N-({3-nitro-4-[(tetrahydro-2H-pyran-4-ylmethyl)amino]phenyl}sulfonyl)benzamide;

N-({3-nitro-4-[(tetrahydro-2H-pyran-4-ylmethyl)amino]phenyl}sulfonyl)-4-{4-[2-(4,4,5,5-tetramethyl-1,3,2-dioxaborolan-2-yl)benzyl]piperazin-1-yl}benzamide;

4-(4-{2-[2-(2,6-dimethoxybenzoyl)-3-thienyl]benzylidene}piperidin-1-yl)-N-({3-nitro-4-[(tetrahydro-2H-pyran-4-ylmethyl)amino]phenyl}sulfonyl)benzamide;

1-[adamantan-1-yl]-4-{2-[(1-{-4-[({3-nitro-4-[(tetrahydro-2H-pyran-4-ylmethyl)amino]phenyl}sulfonyl)carbamoyl]phenyl}piperidin-4-ylidene)methyl]phenyl}-N,N-diphenyl-1H-pyrazole-3-carboxamide;

N-({3-nitro-4-[(tetrahydro-2H-pyran-4-ylmethyl)amino]phenyl}sulfonyl)-4-(4-{2-[octahydro-1H-4,7-methanoinden-5-yl(3-phenylpropanoyl)amino]benzyl}piperazin-1-yl)benzamide;

4-[4-(2-{5-[8-azabicyclo[3.2.1]oct-8-ylmethyl]-2-thienyl}benzylidene)piperidin-1-yl]-N-({3-nitro-4-[(tetrahydro-2H-pyran-4-ylmethyl)amino]phenyl}sulfonyl)benzamide;

N-({3-nitro-4-[(tetrahydro-2H-pyran-4-ylmethyl)amino]phenyl}sulfonyl)-4-[4-(4-{[(1S,2S,3S,5R)-2,6,6-trimethylbicyclo[3.1.1]hept-3-yl]amino}benzylidene)piperidin-1-yl]benzamide;

N-({3-nitro-4-[(tetrahydro-2H-pyran-4-ylmethyl)amino]phenyl}sulfonyl)-4-[4-(3-{[(1S,2S,3S,5R)-2,6,6-trimethylbicyclo[3.1.1]hept-3-yl]amino}benzylidene)piperidin-1-yl]benzamide;

4-[4-(2-{5-[4-(adamantan-1-yl)-1,3-thiazol-2-yl]-2-thienyl}benzylidene)piperidin-1-yl]-N-({3-nitro-4-[(tetrahydro-2H-pyran-4-ylmethyl)amino]phenyl}sulfonyl)benzamide;

N-({3-nitro-4-[(tetrahydro-2H-pyran-4-ylmethyl)amino]phenyl}sulfonyl)-4-(4-{2-[5-(4-phenyl-1,3-thiazol-2-yl)-2-thienyl]benzylidene}piperidin-1-yl)benzamide;

N-[(4-{[adamantan-1-ylmethyl]amino}-3-nitrophenypsulfonyl]-4-(4-oxo-4H-chromen-6-yl)benzamide;

N-[(4-{[adamantan-1-ylmethyl]amino}-3-nitrophenypsulfonyl]-4-(1-octyl-1H-pyrazol-4-yl)benzamide;

4-[5-(4-{[(4-{[adamantan-1-ylmethyl]amino}-3-nitrophenyl)sulfonyl]carbamoyl}-phenyl)-1,3-benzothiazol-2-yl]butanoic;

N-{[3-nitro-4-(tetrahydro-2H-pyran-4-ylamino)phenyl]sulfonyl}-4-[(1R,5S)-1,8,8-trimethyl-3-azabicyclo[3.2.1]oct-3-yl]benzamide;

6-{3-[adamantan-1-yl]-4-methoxyphenyl}-N-({4-[(cyclohexylmethyl)amino]-3-nitrophenyl}sulfonyl)-2-naphthamide;

4-{4-[adamantan-1-ylacetyl]piperazin-1-yl}-N-{[3-nitro-4-(tetrahydro-2H-pyran-4-ylamino)phenyl]sulfonyl}benzamide;

4-{[adamantan-1-ylmethyl]amino}-N-{[3-nitro-4-(tetrahydro-2H-pyran-4-ylamino)phenyl]sulfonyl}benzamide;

N-{1-[4-({[3-nitro-4-(tetrahydro-2H-pyran-4-ylamino)phenyl]sulfonyl}carbamoyl)phenyl]piperidin-4-yl}adamantane-1-carboxamide;

4-[adamantan-2-ylamino]-N-{[3-nitro-4-(tetrahydro-2H-pyran-4-ylamino)phenyl]sulfonyl}benzamide; and N-{[3-nitro-4-(tetrahydro-2H-pyran-4-ylamino)phenyl]sulfonyl}-4-{[(1R,2R,3R,5S)-2,6,6-trimethylbicyclo[3.1.1]hept-3-yl]oxy}benzamide.

Pharmaceutical Compositions, Combination Therapies, Methods of Treatment, and Administration Another embodiment comprises pharmaceutical compositions comprising a compound of this invention and an excipient.

Still another embodiment comprises methods of treating cancer in a mammal comprising administering thereto a therapeutically acceptable amount of a compound of this invention.

Still another embodiment comprises methods of treating autoimmune disease in a mammal comprising administering thereto a therapeutically acceptable amount of a compound of this invention.

Still another embodiment pertains to compositions for treating diseases during which anti-apoptotic Bcl-2 proteins are expressed, said compositions comprising an excipient and a therapeutically effective amount of the compound of this invention.

Still another embodiment pertains to methods of treating disease in a patient during which anti-apoptotic Bcl-2 proteins are expressed, said methods comprising administering to the patient a therapeutically effective amount of a compound of this invention.

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer, said compositions comprising an excipient and a therapeutically effective amount of the compound of this invention.

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myclogenous leukemia, myeloma, oral cancer, ovarian cancer, non-small cell lung cancer, prostate cancer, small cell lung cancer or spleen cancer in a patient, said methods comprising administering to the patient a therapeutically effective amount of a compound of this invention.

Still another embodiment pertains to compositions for treating diseases during which are expressed anti-apoptotic Bcl-2 proteins, said compositions comprising an excipient and a therapeutically effective amount of the compound of this invention and a therapeutically effective amount of one additional therapeutic agent or more than one additional therapeutic agent.

Still another embodiment pertains to methods of treating disease in a patient during which are expressed anti-apoptotic Bcl-2 proteins, said methods comprising administering to the patient a therapeutically effective amount of a compound of this invention and a therapeutically effective amount of one additional therapeutic agent or more than one additional therapeutic agent.

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer, said compositions comprising an excipient and a therapeutically effective amount of the compound of this invention and a therapeutically effective amount of one additional therapeutic agent or more than one additional therapeutic agent.

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said methods comprising administering to the patient a therapeutically effective amount of the compound of this invention and a therapeutically effective amount of one additional therapeutic agent or more than one additional therapeutic agent.

Metabolites of compounds of this invention, produced by in vitro or in vivo metabolic processes, may also have utility for treating diseases associated with anti-apoptotic Bcl-2 proteins.

Certain precursor compounds which may be metabolized in vitro or in vivo to form compounds of this invention may also have utility for treating diseases associated with expression of anti-apoptotic Bcl-2 proteins.

Compounds of this invention may exist as acid addition salts, basic addition salts or zwitterions. Salts of the compounds are prepared during isolation or following purification of the compounds. Acid addition salts of the compounds are those derived from the reaction of the compounds with an acid. For example, the acetate, adipate, alginate, bicarbonate, citrate, aspartate, benzoate, benzenesulfonate, bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate, and undecanoate salts of the compounds and prodrugs thereof are contemplated as being embraced by this invention. Basic addition salts of the compounds are those derived from the reaction of the compounds with the hydroxide, carbonate or bicarbonate of cations such as lithium, sodium, potassium, calcium, and magnesium.

The compounds of this invention may be administered, for example, bucally, ophthalmically, orally, osmotically, parenterally (intramuscularly, intraperitoneally intrasternally, intravenously, subcutaneously), rectally, topically, transdermally or vaginally.

Therapeutically effective amounts of compounds of this invention depend on the recipient of the treatment, the disorder being treated and the severity thereof, the composition containing the compound, the time of administration, the route of administration, the duration of treatment, the compound potency, its rate of clearance and whether or not another drug is co-administered. The amount of a compound of this invention used to make a composition to be administered daily to a patient in a single dose or in divided doses is from about 0.03 to about 200 mg/kg body weight. Single dose compositions contain these amounts or a combination of submultiples thereof.

Compounds of this invention may be administered with or without an excipient. Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Excipients for preparation of compositions comprising a compound of this invention to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof. Excipients for preparation of compositions comprising a compound of this invention to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound of this invention to be administered osmotically include, for example, chlorofluorohydrocarbons, ethanol, water and mixtures thereof. Excipients for preparation of compositions comprising a compound of this invention to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound of this invention to be administered rectally or vaginally include, for example, cocoa butter, polyethylene glycol, wax and mixtures thereof.

Compounds are expected to be useful when used with alkylating agents, angiogenesis inhibitors, antibodies, antimetabolites, antimitoties, antiproliferatives, antivirals, aurora kinase inhibitors, other apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (1APs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263, (i.e., N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide) or ABT-737 (i.e., N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) in multiple tumor cell lines (Tse et. al, *Cancer Research* 2008, 68(9), 3421 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-(3-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanylmethyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenyl sulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN®

(aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR™ (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds of this invention may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combrestatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); 0: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), cniluracil, EVIZON™ (squalamine lactate), DIMERICINE® (T4N5 liposome lotion), discodermolide, DX-8951f (exatecan mesylate), enzastaurin, EP0906 (epithilone B), GARDASTL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECTN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zoledronic acid), zorubicin and the like.

Determination of Biological Activity

Assays for the inhibition of Bcl-2 family proteins, using Bcl-xL as a representative example, were performed in 96-well microtiter plates. Compounds of the present invention were diluted in DMSO to concentrations between 10 M and 10 μM and introduced into each cell of the plate. A mixture totaling 125 L per well of assay buffer (20 mM phosphate buffer (pH 7.4), 1 mM EDTA, 50 mM NaCl, 0.05% pluronic F-68), 6 nM of BCL-$X_L$ protein (prepared according to the procedure described in *Science* 1997, 275, 983-986), 1 nM fluorescein-labeled BAD peptide (purchased from Synpep, CA), and the DMSO solution of the compound of the present invention was shaken for 2 minutes and placed in a LJL Analyst (LJL Bio Systems, CA). A negative control (DMSO, 15 nM BAD peptide, assay buffer) and a positive control (DMSO, 15 nM BAD peptide, 30 nM BCL-$X_L$, assay buffer) were used to determine the range of the assay. Polarization was measured at room temperature using a continuous Fluorescein lamp (excitation 485 nm, emission 530 nm). The $K_i$ value was calculated directly from the mP value by Microsoft Excel.

Assays for the inhibition of Bcl-2 were performed in 96-well microtiter plates. Compounds of the instant invention were diluted in DMSO to concentrations between 10 M and 10 μM and introduced into each well of the plate. A mixture totaling 125 L per well of assay buffer (20 mM phosphate buffer (pH 7.4), 1 mM EDTA, 0.05% PF-68), 10 nM of Bcl-2 protein (prepared according to the procedure described in *PNAS* 2001, 98, 3012-3017), 1 nM fluorescein-labeled BAX peptide (prepared in-house), and the DMSO solution of the compound of the instant invention was shaken for 2 minutes and placed in a LJL Analyst (LJL Bio Systems, CA. Polarization was measured at room temperature using a continuous Fluorescein lamp (excitation 485 nm, emission 530 nm). $K_i$ values were calculated using Microsoft Excel.

Inhibition constants ($K_i$) for compounds according to the invention are shown in TABLE 1 below. Where the $K_i$ for a compound is represented as ">" (greater than) a certain numerical value, it is intended to mean that the binding affinity value is greater than the limits of detection of the assay used. Where the $K_i$ for a compound is represented as "<" (less than) a certain numerical value, it is intended to mean that the binding affinity value is lower than the limit of detection of the assay used.

TABLE 1

FPA Bcl-2 Binding Ki (μM)

| Example No. | Bcl-2 FPA 11 pt Ki (uM) | Example No. | Bcl-2 FPA 11 pt Ki (uM) |
|---|---|---|---|
| 1 | 0.174 | 44 | >6.245 |
| 2 | 0.22 | 45 | 0.079 |
| 3 | 0.065 | 46 | 0.033 |
| 4 | 0.19089 | 47 | 0.066928 |
| 5 | 0.059174 | 48 | 1.388 |
| 6 | 0.15496 | 49 | 0.342 |
| 7 | 1.2644 | 50 | 3.556 |
| 8 | 0.084635 | 51 | 1.049 |
| 9 | <0.020 | 52 | 1.392 |
| 10 | <0.020 | 53 | 0.84492 |
| 11 | 1.3044 | 54 | >9.7305 |
| 12 | 0.3038 | 55 | 0.35156 |
| 13 | 0.60807 | 56 | <0.020 |
| 14 | 0.047406 | 57 | 0.13387 |
| 15 | <0.020 | 58 | >18.674 |
| 16 | 0.039706 | 59 | 0.066678 |
| 17 | 0.030083 | 60 | 0.50423 |
| 18 | <0.020 | 61 | <0.020 |
| 19 | 0.6035 | 62 | 0.28077 |
| 20 | >51.897 | 63 | 0.27762 |
| 21 | 5.5988 | 64 | 1.4727 |
| 22 | 0.031403 | 65 | 0.9281 |
| 23 | <0.020 | 66 | 0.0078655 |
| 24 | 2.2651 | 67 | 4.0442 |
| 25 | 0.97859 | 68 | 0.092644 |
| 26 | 1.1655 | 69 | 0.78864 |
| 27 | 0.027114 | 70 | 0.03537 |
| 28 | 0.029579 | 71 | <0.020 |
| 29 | 0.35402 | 72 | 0.28748 |
| 30 | 0.29489 | 73 | 0.093189 |
| 31 | 0.031861 | 74 | 0.10238 |
| 32 | 0.091893 | 75 | 0.25081 |
| 33 | <0.020 | 76 | nd |
| 34 | 0.047684 | 77 | nd |
| 35 | 0.021652 | 78 | nd |
| 36 | 0.12146 | 79 | 1.42 |

TABLE 1-continued

FPA Bcl-2 Binding Ki (μM)

| Example No. | Bcl-2 FPA 11 pt Ki (uM) | Example No. | Bcl-2 FPA 11 pt Ki (uM) |
|---|---|---|---|
| 37 | 0.16544 | 80 | 1.303 |
| 38 | 0.14942 | 81 | 4.726 |
| 39 | 2.9135 | 82 | 2.18 |
| 40 | 0.054683 | 83 | >6.245 |
| 41 | 5.186 | 84 | 2.378 |
| 42 | 2.479 | 85 | 2.878 |
| 43 | >6.245 | | |

The inhibition constant ($K_i$) is the dissociation constant of an enzyme-inhibitor complex or a protein/small molecule complex, wherein the small molecule is inhibiting binding of one protein to another protein. So a large $K_i$ value indicates a low binding affinity and a small $K_i$ value indicates a high binding affinity.

This inhibitory data demonstrates the utility of compounds having formula (I) as inhibitors of anti-apoptotic Bcl-2 protein.

It is expected that, because compounds of this invention bind to Bcl-2, they would also have utility as binders to anti-apoptotic proteins having close structural homology to Bcl-2, such as, for example, anti-apoptotic Bcl-$X_L$, Bcl-w, Mcl-1 and Bfl-1/A1 proteins.

Involvement of Bcl-2 proteins in bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, chronic lymphocytic leukemia, myeloma, prostate cancer spleen cancer, and the like is described in commonly-owned PCT US 2004/36770, published as WO 2005/049593, and PCT US 2004/37911, published as WO 2005/024636.

Involvement of Bcl-2 proteins in immune and autoimmune diseases is described in *Current Allergy and Asthma Reports* 2003, 3, 378-384; *British Journal of Haematology* 2000, 110(3), 584-90; *Blood* 2000, 95(4), 1283-92; and *New England Journal of Medicine* 2004, 351(14), 1409-1418.

Involvement of Bcl-2 proteins in arthritis is disclosed in commonly-owned U.S. Provisional Patent Application Ser. No. 60/988,479.

Involvement of Bcl-2 proteins in bone marrow transplant rejection is disclosed in commonly-owned U.S. patent application Ser. No. 11/941,196.

Overexpression of Bcl-2 proteins correlates with resistance to chemotherapy, clinical outcome, disease progression, overall prognosis or a combination thereof in various cancers and disorders of the immune system. Cancers include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenstrom's macroglobulinemia, testicular tumors, uterine cancer, Wilms' tumor and the like.

It is also expected that compounds of this invention would inhibit growth of cells expressing Bcl-2 proteins derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

Autoimmune disorders include acquired immunodeficiency disease syndrome (AIDS), autoimmune lymphoproliferative syndrome, hemolytic anemia, inflammatory diseases, and thrombocytopenia, acute or chronic immune disease associated with organ transplantation, Addison's disease, allergic diseases, alopecia, alopecia areata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-1-antitrypsin deficiency, Alzheimer's disease, amyotrophic lateral sclerosis, anemia, angina pectoris, ankylosing spondylitis associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anaemia, autoimmune hepatitis, type-1 autoimmune hepatitis (classical autoimmune or lupoid hepatitis), autoimmune mediated hypoglycemia, autoimmune neutropaenia, autoimmune thrombocytopaenia, autoimmune thyroid disease, B cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chlamydia, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, colorectal common varied immunodeficiency (common variable hypogammaglobulinaemia), conjunctivitis, connective tissue disease associated interstitial lung disease, contact dermatitis, Coombs positive haemolytic anaemia, cor pulmonale, Creutzfeldt-Jakob disease, cryptogenic autoimmune hepatitis, cryptogenic fibrosing alveolitis, culture negative sepsis, cystic fibrosis, cytokine therapy associated disorders, Crohn's disease, dementia pugilistica, demyelinating diseases, dengue hemorrhagic fever, dermatitis, dermatitis scleroderma, dermatologic conditions, dermatomyositis/polymyositis associated lung disease, diabetes, diabetic arteriosclerotic disease, diabetes mellitus, Diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine, receptors, drug sensitivity, eczema, encephalomyelitis, endocarditis, endocrinopathy, enteropathic synovitis, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram negative sepsis, gram positive sepsis, granulomas due to intracellular organisms, group B streptococci (GBS) infection, Grave's disease, haemosiderosis associated lung disease, hairy cell leukemia, hairy cell leukemia, Hallerrorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schoenlcin purpurca, Hepatitis A, Hepatitis B, Hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leucopaenia, idiopathic pulmonary fibrosis, idiopathic thrombocytopaenia, idiosyncratic liver disease, infantile spinal muscular atrophy, infectious diseases, inflammation of the aorta, inflammatory bowel disease, insulin dependent diabetes mellitus, interstitial pneumonitis, iridocyclitis/uveitis/optic neuritis, ischemia-reperfusion injury, ischemic stroke, juvenile pernicious anaemia, juvenile rheumatoid arthritis, juvenile spinal muscular atrophy, Kaposi's sarcoma, Kawasaki's disease, kidney transplant rejection, *legionella*, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcemia, microscopic vasculitis of the kidneys, migraine headache, mitochondrial multisystem disorder, mixed connective tissue disease, mixed connective tissue disease associated lung disease, monoclonal gammopathy, multiple myeloma, multiple systems degenerations (Mencel Dejerine-Thomas Shi-Drager and Machado-Joseph), myalgic encephalitis/Royal Free Disease, myasthenia gravis, microscopic vasculitis of the kidneys, *mycobacterium avium intracellulare, mycobacterium tuberculosis*, myelodysplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, Non-alcoholic Steatohepatitis, occlusion of the abdominal aorta and its branches, occlusive arterial disorders, organ transplant rejection, orchitis/epidydimitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, pemphigus vulgaris, pemphigus foliaceus, pemphigoid, perennial rhinitis, pericardial disease, peripheral atherloscle-rotic disease, peripheral vascular disorders, peritonitis, pernicious anemia, phacogenic uveitis, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, Progressive supranucleo Palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease, Raynoud's disease, Refsum's disease, regular narrow QRS tachycardia, Reiter's disease, renal disease NOS, renovascular hypertension, reperfusion injury, restrictive cardiomyopathy, rheumatoid arthritis associated interstitial lung disease, rheumatoid spondylitis, sarcoidosis, Schmidt's syndrome, scleroderma, senile chorea, Senile Dementia of Lewy body type, sepsis syndrome, septic shock, seronegative arthropathies, shock, sickle cell anemia, Sjögren's disease associated lung disease, Sjörgren's syndrome, skin allograft rejection, skin changes syndrome, small bowel transplant rejection, sperm autoimmunity, multiple sclerosis (all subtypes), spinal ataxia, spinocerebellar degenerations, spondyloarthropathy, spondyloarthopathy, sporadic, polyglandular deficiency type I sporadic, polyglandular deficiency type II, Still's disease, streptococcal myositis, stroke, structural lesions of the cerebellum, Subacute sclerosing panencephalitis, sympathetic ophthalmia, Syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, systemic sclerosis, systemic sclerosis-associated interstitial lung disease, T-cell or FAB ALL, Takayasu's disease/arteritis, Telangiectasia, Th2 Type and Th1 Type mediated diseases, thromboangitis obliterans, thrombocytopenia, thyroiditis, toxicity, toxic shock syndrome, transplants, trauma/hemorrhage, type-2 autoimmune hepatitis (anti-LKM antibody hepatitis), type B insulin resistance with acanthosis nigricans, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, vital encephalitis/aseptic meningitis, vital-associated hemaphagocytic syndrome, Wegener's granulomatosis, Wernicke-Korsakoff syndrome, Wilson's disease, xenograft rejection of any organ or tissue, yersinia and *salmonella*-associated arthropathy and the like.

Schemes and Experimentals

The following abbreviations have the meanings indicated. ADDP means 1,1'-(azodicarbonyl)dipiperidine; AD-mix-13 means a mixture of $(DHQD)_2PHAL$, $K_3Fe(CN)_6$, $K_2CO_3$, and $K_2SO_4$; 9-BBN means 9-borabicyclo(3.3.1)nonane; Boc means tert-butoxycarbonyl; $(DHQD)_2PHAL$ means hydroquinidine 1,4-phthalazinediyl diethyl ether; DBU means 1,8-diazabicyclo[5.4.0]undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)-butane; dppe means 1,2-bis(diphenylphosphino)ethane; dppf means 1,1'-bis(diphenylphosphino)ferrocene; dppm means 1,1-bis(diphenylphosphino)methane; EDAC.HCl means 1-(3-dimethylaminopropyl)-3-ethylcarbodiimide hydrochloride; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; MP-$BH_3$ means macroporous triethylammonium methylpolystyrene cyanoborohydride; TEA means triethylamine; TFA means trifluoroacetic acid; THF means tetrahydrofuran; NCS means N-chlorosuccinimide; NMM means N-methylmorpholine; NMP means N-methylpyrrolidine; $PPh_3$ means triphenylphosphine.

Compounds of this invention may be made by synthetic chemical processes, examples of which are shown herein. Exemplary schemes of the most useful and readily understood description of procedures and conceptual aspects of this invention are disclosed in commonly-owned U.S. patent application Ser. No. 12/631,367, and 12/631,404. It is meant to be understood that the order of the steps in the processes may be varied, that reagents, solvents and reaction conditions may be substituted for those specifically mentioned, and that vulnerable moieties may be protected and deprotected, as necessary.

The following examples are presented to provide what is believed to be the most useful and readily understood description of procedures and conceptual aspects of this invention. The exemplified compounds and intermediates were named using ACD/ChemSketch Version 12.01 (13 May 2009), Advanced Chemistry Development Inc., Toronto, Ontario), or ChemDraw® Ver. 9.0.5 (CambridgeSoft, Cambridge, Mass.).

Example 1

4-{4-[(4'-chlorobiphenyl-2-yl)methyl]piperazin-1-yl}-N-[(3-nitro-4-{[(1R,2R,3R,5S)-2,6,6-trimethyl-bicyclo[3.1.1]hept-3-yl]amino}phenyl)sulfonyl]benzamide

Example 1A 4-(4-((4'-chlorobiphenyl-2-yl)methyl)piperazin-1-yl) benzoic Acid EXAMPLE 1A was prepared using methods described by Bruncko, et. al., *J. Med. Chem.* 2007, 50, 641-662.

Example 1B

N-(4-chloro-3-nitrophenylsulfonyl)-4-(4-((4'-chloro-biphenyl-2-yl)methyl)piperazin-1-yl)benzamide EXAMPLE 1A (10 g), 4-chloro-3-nitrobenzenesulfonamide (5.82 g), 1-ethyl-3-[3-(dimethylamino)propyl]-carbodiimide hydrochloride (9.42 g) and 4-dimethylaminopyridine (3.00 g) were combined in dichloromethane (98 ml). The mixture was stirred at room temperature overnight, diluted with dichloromethane, and poured into water. The organic layer was washed thoroughly with water, and washed with 1M aqueous HCl solution and 5% aqueous $NaHCO_3$ solution. The organic layer was washed again with water and brine. The organic layer was dried over $MgSO_4$, filtered, and the filtrate was concentrated under vacuum. The crude material was purified by flash chromatography, eluting with a gradient of 2% methanol/dichloromethane to 10% methanol/dichloromethane. $^1$H NMR (500 MHz, dimethylsulfoxide-$d_6$) δ 12.08 (br s, 1H), 8.64 (d, 1H), 8.37 (d, 1H), 7.94 (dd, 1H), 7.75 (m, 3H), 7.54 (m, 4H), 7.40 (m, 2H), 7.35 (d, 2H), 6.93 (d, 2H), 4.39 (br s, 1H), 4.02 (m, 1H), 3.91 (br s, 2H), 3.28 (br s, 2H), 3.08 (br s, 3H), 2.89 (br s, 2H), 2.73 (m, 1H), 2.40 (m, 1H), 2.09 (m, 1H), 1.97 (m, 1H), 1.87 (m, 1H), 1.64 (m, 1H), 1.24 (s, 3H), 1.12 (d, 3H), 1.08 (s, 3H).

Example 1C

4-{4-[(4'-chlorobiphenyl-2-yl)methyl]piperazin-1-yl}-N-[(3-nitro-4-{[(1R,2R,3R,5S)-2,6,6-trimethyl-bicyclo[3.1.1]hept-3-yl]amino}phenyl)sulfonyl]benzamide EXAMPLE 1B (40 mg) and (1R,2R,3R,5S)-2,6,6-trimethylbicyclo[3.1.1]heptan-3-amine (19.60 mg) were combined in dioxane (1 ml). Triethylamine (0.027 ml) was added. The mixture was heated to 90° C. overnight, concentrated under vacuum, and purified by preparative HPLC using a C18 column, 250×21.20 mm, 5μ, and eluting with a gradient of 20-100% $CH_3CN$ vs. 0.1% trifluoroacetic acid in water, giving the product as a trifluoroacetate salt. $^1$H NMR (500 MHz, dimethylsulfoxide-$d_6$) δ 12.08 (br s, 1H), 8.64 (d, 1H), 8.37 (d, 1H), 7.94 (dd, 1H), 7.75 (m, 3H), 7.54 (m, 4H), 7.40 (m, 2H), 7.35 (d, 2H), 6.93 (d, 2H), 4.39 (br s, 1H), 4.02 (m, 1H), 3.91 (br s, 2H), 3.28 (br s, 2H), 3.08 (br s, 3H), 2.89 (br s, 2H), 2.73 (m, 1H), 2.40 (m, 1H), 2.09 (m, 1H), 1.97 (m, 1H), 1.87 (m, 1H), 1.64 (m, 1H), 1.24 (s, 3H), 1.12 (d, 3H), 1.08 (s, 3H).

Example 2

4-(4-{acetyl[((1S,2S,3S,5R)-2,6,6-trimethylbicyclo [3.1.1]hept-3-yl]amino}piperidin-1-yl)-N-({4-[(cyclohexylmethyl)amino]-3-nitrophenyl}sulfonyl)benzamide

Example 2A

4-{4-[acetyl-((1S,2S,3S,5R)-2,6,6-trimethyl-bicyclo [3.1.1]hept-3-yl)-amino]-piperidin-1-yl}-benzoic acid ethyl ester EXAMPLE 45C (50 mg) was dissolved in dichloromethane (2 mL). Triethylamine (0.022 mL, 16 mg) was added, followed by acetyl chloride (0.010 mL, 11 mg). The solution was mixed at room temperature for 16 hours and then purified by flash column chromatography on silica gel using 30% ethyl acetate in hexanes to afford the title compound.

Example 2B

4-{4-[Acetyl-((1S,2S,3S,5R)-2,6,6-trimethyl-bicyclo [3.1.1]hept-3-yl)-amino]-piperidin-1-yl}-benzoic Acid EXAMPLE 2A (55 mg) was dissolved in tetrahydrofuran (0.6 mL), methanol (0.2 mL), and water (0.2 mL) and treated with lithium hydroxide monohydrate (22 mg). The solution was stirred at room temperature for 16 hours. The solution was acidified with 1M hydrochloric acid, extracted with ethyl acetate, dried with anhydrous sodium sulfate, filtered, and concentrated to afford the title compound.

Example 2C

4-Fluoro-3-nitro-benzenesulfonamide

2-Fluoronitrobenzene (141 g, 1.0 mol) and chlorosulfonic acid (300 mL) were heated at 60° C. for 10 hours. After the reaction mixture cooled to room temperature, it was carefully poured to ice (about 1 kg) in a four liter Erlenmeyer flask and cooled efficiently by an ice-brine bath. The mixture was extracted with ether (4 L), and brine (2 L). The resulting solution was cooled to −40° C. Concentrated ammonium hydroxide (300 mL) was then added with vigorous stirring, and the addition rate was controlled to allow the reaction mixture to stay below −10° C. (internal temperature). Dry ice cubes were added to the reaction mixture to lower the temperature when necessary. Immediately after the addition was complete, the resulting mixture was separated, and the aqueous phase was extracted with ethyl acetate (2 L). The combined organic phases were washed with the aqueous 4 M hydrochloric acid (300 mL) and brine (100 mL), dried on anhydrous magnesium sulfate, filtered, and concentrated. The resulting solid was recrystallized from ethyl acetate/hexane mixture. The mother liquid from the recrystallization was concentrated and recrystallized in the same manner, and the resulting solids were combined to afford the title compound.

Example 2D 4-(Cyclohexylmethyl-amino)-3-nitro-benzene-sulfonamide

To a solution of EXAMPLE 2C (7.70 g) in tetrahydrofuran (35 mL) was added dropwise a solution of cyclohexylmethylamine (6.0 mL, 5.22 g) and diisopropylethylamine (8.0 mL, 5.92 g) in tetrahydrofuran (15 mL). After the addition, tetrahydrofuran (20 mL) was added, and the reaction was stirred at room temperature for 16 hours. The solution was added to water and extracted with a solution of ethyl acetate and dichloromethane (1:1 by volume). The solution was dried over anhydrous sodium sulfate, filtered, and the filtrate volume was reduced to isolate the title compound by crystallization.

Example 2E 4-(4-{acetyl[(1S,2S,3S,5R)-2,6,6-trimethylbicyclo [3.1.1]hept-3-yl]amino}piperidin-1-yl)-N-({4-[(cyclohexylmethyl)amino]-3-nitrophenyl}sulfonyl)benzamide The title compound was prepared by substituting EXAMPLE 2B for EXAMPLE 1A and EXAMPLE 2D for 4-chloro-3-nitrobenzenesulfonamide in EXAMPLE 1B. $^1$H NMR (300 MHz, dimethylsulfoxide-$d_6$) δ 8.50 (br s, 1H), 8.40 (m, 1H), 7.88 (dd, 1H), 7.73 (d, 1H), 7.71 (d, 1H), 7.06 (dd, 1H), 6.86 (d, 1H), 6.81 (d, 1H), 4.16 (m, 1H), 3.96-3.77 (m, 2H), 3.25 (t, 4H), 3.18-3.06 (m, 2H), 2.77 (m, 4H), 2.48-2.23 (m, 2H), 2.14-1.95 (m, 8H), 1.86 (m, 2H), 1.77-1.60 (m, 11H), 1.25-1.14 (m, 8H), 1.07-1.00 (m, 4H), 0.95-0.86 (m, 2H).

Example 3

4-(4-{benzoyl[(1S,2S,3S,5R)-2,6,6-trimethylbicyclo [3.1.1]hept-3-yl]amino}piperidin-1-yl)-N-({4-[(cyclohexylmethyl)amino]-3-nitrophenyl}sulfonyl)benzamide

Example 3A

4-{4-[Benzoyl-((1S,2S,3S,5R)-2,6,6-trimethyl-bicyclo[3.1.1]hept-3-yl)-amino]-piperidin-1-yl}-benzoic Acid Ethyl Ester The title compound was prepared by substituting benzoyl chloride for acetyl chloride in EXAMPLE 2A.

Example 3B

4-{4-[Benzoyl-((1S,2S,3S,5R)-2,6,6-trimethyl-bicyclo[3.1.1]hept-3-yl)-amino]-piperidin-1-yl}-benzoic Acid The title compound was prepared by substituting EXAMPLE 3A for EXAMPLE 2A in EXAMPLE 2B.

Example 3C 4-(4-{benzoyl[(1S,2S,3S,5R)-2,6,6-trimethylbicyclo [3.1.1]hept-3-yl]amino}piperidin-1-yl)-N-({4-[(cyclohexylmethyl)amino]-3-nitrophenyl}sulfonyl)benzamide The title compound was prepared by substituting EXAMPLE 3B for EXAMPLE 1A and EXAMPLE 2D for 4-chloro-3-nitrobenzenesulfonamide in EXAMPLE 1B. $^1$H NMR (300 MHz, dimethylsulfoxide-$d_6$) δ 11.98 (br s, 1H), 8.51 (br s, 1H), 8.42 (br s, 1H), 7.89 (dd, 1H), 7.43 (d, 2H), 7.42 (m, 3H), 7.29 (d, 2H), 7.08 (d, 1H), 6.85 (d, 2H), 4.03-3.75 (m, 3H), 3.24 (t, 4H), 2.86 (m, 2H), 2.37 (m, 2H), 2.11 (m, 2H), 1.97-1.82 (m, 2H), 1.78-1.55 (m, 10H), 1.23-0.91 (m, 11H), 0.79 (d, 2H), 0.45 (s, 1H).

Example 4

N-({4-[(cyclohexylmethyl)amino]-3-nitrophenyl}sulfonyl)-3'-{[(1S,2S,3S,5R)-2,6,6-trimethylbicyclo[3.1.1]hept-3-yl]amino}biphenyl-4-carboxamide

Example 4A

Methyl 3'-bromobiphenyl-4-carboxylate 4-(Methoxycarbonyl)phenylboronic acid (1.55 g, 8.63 mmol), 1-bromo-3-iodobenzene (2.22 g, 7.84 mmol), [1,1'-bis(diphenylphosphino)ferrocene]dichloropalladium(II) (0.29 g, 0.392 mmol), and CsF (2.38 g, 15.7 mmol) in dioxane (40 mL) were stirred at 80° C. for 8 hours. The reaction was cooled, poured into ethyl acetate, washed twice with water and brine, and the combined organic layers were concentrated. The residue was chromatographed on silica gel using 2-20% ethyl acetate in hexanes afford the title compound.

Example 4B

Methyl 3'-((1S,2S,3S,5R)-2,6,6-trimethylbicyclo [3.1.1]heptan-3-ylamino)biphenyl-4-carboxylate EXAMPLE 4A (146 mg, 0.50 mmol), (1S,2S,3S,5R)-2,6, 6-trimethylbicyclo[3.1.1]heptan-3-amine (92 mg, 0.60 mmol), tris(dibenzylideneacetone)dipalladium(0) (23 mg, 0.025 mmol), tri-t-butylphosphonium tetrafluoroborate (11.7 mg, 0.04 mmol), and $K_3PO_4$ (160 mg, 0.75 mmol) in diglyme (5 mL) were stirred at 100° C. for 24 hours. The reaction was cooled and was chromatographed on silica gel using 5% ethyl acetate in hexanes to afford the title compound.

Example 4C

3'-((1S,2S,3S,5R)-2,6,6-trimethylbicyclo[3.1.1]heptan-3-ylamino)biphenyl-4-carboxylic Acid The title compound was prepared as described in EXAMPLE 2B using EXAMPLE 4B in place of EXAMPLE 2A.

Example 4D

N-({4-[(cyclohexylmethyl)amino]-3-nitrophenyl}sulfonyl)-3'-{[(1S,2S,3S,5R)-2,6,6-trimethylbicyclo[3.1.1]hept-3-yl]amino}biphenyl-4-carboxamide The title compound was prepared as described in EXAMPLE 1B using EXAMPLE 4C in place of EXAMPLE 1A and EXAMPLE 2D in place of 4-chloro-3-nitrobenzene-sulfonamide. ¹H NMR (300 MHz, dimethylsulfoxide-$d_6$) δ 11.90 (s, 1H), 8.65 (m, 2H), 7.97 (d, 1H), 7.93 (d, 2H), 7.68 (d, 2H), 7.28 (d, 1H), 7.17 (t, 1H), 6.88 (s, 1H), 6.82 (d, 1H), 6.66 (d, 1H), 5.70 (m, 1H), 3.65 (m, 1H), 2.55 (m, 2H), 2.34 (m, 4H), 1.72 (m, 6H), 1.52 (m, 1H), 0.99-1.49 (m, 16H).

Example 5

N-({4-[cyclohexylmethyl)amino]-3-nitrophenyl}sulfonyl)-4-(4-{(phenylacetyl)[(1S,2S,3S,5R)-2,6,6-trimethylbicyclo[3.1.1]hept-3-yl]amino}piperidin-1-yl)benzamide Example 5A 4-{4-[Phenylacetyl-((1S,2S,3S,5R)-2,6,6-trimethyl-bicyclo[3.1.1]hept-3-yl)-amino]-piperidin-1-yl}-benzoic Acid Ethyl Ester The title compound was prepared by substituting phenyl acetyl chloride for acetyl chloride in EXAMPLE 2A.

Example 5B

4-{4-[Phenylacetyl-01S,2S,3S,5R)-2,6,6-trimethyl-bicyclo[3.1.1]hept-3-yl)-amino]-piperidin-1-yl}-benzoic Acid The title compound was prepared by substituting EXAMPLE 5A for EXAMPLE 2A in EXAMPLE 2B.

Example 5C

N-({4-[(cyclohexylmethyl)amino]-3-nitrophenyl}sulfonyl)-4-(4-{(phenyl acetyl)[(1S,2S,3S,5R)-2,6,6-trimethylbicyclo[3.1.1]hept-3-yl]amino}piperidin-1-yl)benzamide The title compound was prepared by substituting EXAMPLE 5B for EXAMPLE 1A and EXAMPLE 2D for 4-chloro-3-nitrobenzenesulfonamide in EXAMPLE 1B. ¹H NMR (300 MHz, dimethylsulfoxide-$d_6$) δ 11.98 (br s, 1H), 8.63 (m, 2H), 7.93 (dt, 1H), 7.73 (d, 1H), 7.71 (d, 1H), 7.33-7.19 (m, 6H), 6.91 (d, 2H), 4.10 (m, 1H), 3.95 (m, 2H), 3.78 (d, 1H), 3.29 (t, 4H), 3.00-2.60 (m, 4H), 2.34 (m, 1H), 2.17 (m, 1H), 2.05 (m, 1H), 1.90 (m, 1H), 1.80-1.53 (m, 9H), 1.23-1.17 (m, 8H), 0.99 (m, 2H), 0.92-0.86 (m, 6H).

Example 6

N-({4-[(cyclohexylmethyl)amino]-3-nitrophenyl}sulfonyl)-4'-{[(1S,2S,3S,5R)-2,6,6-trimethylbicyclo[3.1.1]hept-3-yl]amino}biphenyl-4-carboxamide Example 6A Methyl 4'-bromobiphenyl-4-carboxylate The title compound was prepared as described in EXAMPLE 4A using 1-bromo-4-iodobenzene in place of 1-bromo-3-iodobenzene.

Example 6B

Methyl 4'-((1S,2S,3S,5R)-2,6,6-trimethylbicyclo[3.1.1]heptan-3-ylamino)biphenyl-4-carboxylate The title compound was prepared as described in EXAMPLE 4B using EXAMPLE 6A in place of EXAMPLE 4A.

Example 6C

4'-((1S,2S,3S,5R)-2,6,6-trimethylbicyclo[3.1.1]heptan-3-ylamino)biphenyl-4-carboxylic Acid The title compound was prepared as described in EXAMPLE 2B using EXAMPLE 6B in place of EXAMPLE 2A.

Example 6D

N-({4-[(cyclohexylmethyl)amino]-3-nitrophenyl}sulfonyl)-4'-{[(1S,2S,3S,5R)-2,6,6-trimethylbicyclo[3.1.1]hept-3-yl]amino}biphenyl-4-carboxamide The title compound was prepared as described in EXAMPLE 1B using EXAMPLE 6C in place of EXAMPLE 1A and EXAMPLE 2D in place of 4-chloro-3-nitrobenzene-sulfonamide. ¹H NMR (300 MHz, dimethylsulfoxide-$d_6$) δ 11.90 (s, 1H), 8.66 (m, 2H), 7.97 (d, 1H), 7.87 (d, 2H), 7.66 (d, 2H), 7.51 (d, 2H), 7.26 (d, 2H), 7.18 (m, 1H), 6.79 (d, 2H), 5.95 (m, 1H), 3.65 (m, 1H), 2.60 (m, 2H), 2.33 (m, 2H), 1.94 (m, 2H), 1.72 (m, 6H), 1.23 (s, 3H), 1.19 (m, 4H), 0.93-1.15 (m, 11H).

Example 7

N-({4-[(cyclohexylmethyl)amino]-3-nitrophenyl}sulfonyl)-4'-{(3-phenylpropyl)[(1S,2S,3S,5R)-2,6,6-trimethylbicyclo[3.1.1]hept-3-yl]amino}biphenyl-4-carboxamide Example 7A 4'-((3-phenylpropyl)((1S,2S,3S,5R)-2,6,6-trimethylbicyclo[3.1.1]heptan-3-yl)amino)biphenyl-4-carboxylic Acid EXAMPLE 6C (100 mg, 0.286 mmol), 3-phenylpropanal (101 mg, 0.715 mmol), and sodium triacetoxyborohydride (182 mg, 0.858 mmol) was stirred in 1,2-dichloroethane (5 mL) for 24 hours. The mixture was triturated with dichloromethane and ether to afford the title compound.

Example 7B

N-({4-[(cyclohexylmethyl)amino]-3-nitrophenyl}sulfonyl)-4'-{(3-phenylpropyl)[(1S,2S,3S,5R)-2,6,6-trimethylbicyclo[3.1.1]hept-3-yl]amino}biphenyl-4-carboxamide The title compound was prepared as described in EXAMPLE 1B using EXAMPLE 7A in place of EXAMPLE 1A and EXAMPLE 2D in place of 4-chloro-3-nitrobenzene-sulfonamide.

Example 8

4-{6-[adamantan-1-ylmethyl]-2,6-diazabicyclo [3.2.1]oct-2-yl}-N-({4-[(cyclohexylmethyl)amino]-3-nitrophenyl}sulfonyl)benzamide

Example 8A

Benzyl 2-(4-(ethoxycarbonyl)phenyl)-2,6-diazabicyclo[3.2.1]octane-6-carboxylate

Benzyl 2,6-diazabicyclo[3.2.1]octane-6-carboxylate (300 mg) was dissolved in dimethylsulfoxide (3 mL), then ethyl 4-fluorobenzoate (172 mg) and potassium carbonate (206 mg) were added. The reaction was heated at 130° C. overnight. After cooling, the reaction was diluted with water and extracted with ethyl acetate. The organic layer was washed with brine and dried over sodium sulfate. After filtration and concentration of the filtrate, the resultant crude material was purified by column chromatography on silica gel using 7/3 hexanes/ethyl acetate to afford the title compound.

Example 8B

Ethyl 4-(2,6-diazabicyclo[3.2.1]octan-2-yl)benzoate

EXAMPLE 8A (82 mg) was dissolved in methanol (6 mL), then 10% palladium on carbon (13 mg) was added, and the reaction stirred under a hydrogen balloon for 3 hours. The reaction was then filtered through celite and the filtrate was concentrated, giving the crude product that was used in the next step with no purification.

Example 8C

Ethyl 4-{6-[adamantan-1-ylcarbonyl]-2,6-diazabicyclo[3.2.1]oct-2-yl}benzoate

EXAMPLE 8B (45 mg) and adamantane-1-carboxylic acid (31 mg) were dissolved in dichloromethane (1 mL), then 1-ethyl-3-[3-(dimethylamino)propyl]-carbodiimide hydrochloride (38 mg), and 4-dimethylaminopyridine (7 mg) were added and the reaction stirred at room temperature overnight. The reaction was then diluted with ethyl acetate and washed with twice with 1M $H_3PO_4$, twice with saturated $NaHCO_3$, and once with brine. The organic layer was dried over sodium sulfate. After filtration and concentration, the title compound was carried on with no further purification.

Example 8D

Ethyl 4-{6-[adamantan-1-ylmethyl]-2,6-diazabicyclo [3.2.1]oct-2-yl}benzoate

EXAMPLE 8C (70 mg) was dissolved in tetrandyrofuran (2 mL), then a 1.0M solution of borane in tetrahydrofuran (0.25 mL) was added and the reaction heated at 70° C. for one hour. After cooling to room temperature, 2.5M HCl in ethanol (2 mL) was added and the reaction heated at 70° C. for one hour. After cooling and concentration the residue was redissolved in 2.5M HCl in ethanol (4 mL) and heated at 70° C. for one hour. The reaction was then cooled to room temperature and partitioned between ethyl acetate and 2M aqueous $Na_2CO_3$. The organic layer was washed with brine and dried over sodium sulfate. After filtration and concentration the resultant product was carried on without further purification.

Example 8E

4-{6-[adamantan-1-ylmethyl]-2,6-diazabicyclo [3.2.1]oct-2-yl}benzoic Acid

EXAMPLE 8D (68 mg) was dissolved in tetrahydrofuran (1 mL) and methanol (1 mL). Then 1N aqueous lithium hydroxide was added (0.32 mL) and the mixture was heated at 65° C. overnight. The reaction was then cooled and concentrated, and water was added, adjusting the pH to 1 with 2N aqueous HCl. The reaction mixture was extracted with chloroform/methanol, and after drying the organic layer over sodium sulfate and filtration, the filtrate was concentrated to afford the title compound as a hydrochloride salt.

Example 8F

4-{6-[adamantan-1-ylmethyl]-2,6-diazabicyclo [3.2.1]oct-2-yl}-N-({4-[(cyclohexylmethyl)amino]-3-nitrophenyl}sulfonyl)benzamide EXAMPLE 8E (32 mg), EXAMPLE 2D (30 mg), 1-ethyl-3-[3-(dimethylamino)propyl]-carbodiimide hydrochloride (32 mg), and 4-dimethylaminopyridine (20 mg) were stirred in dichloromethane (1.5 mL) for 24 hours. The product was purified by preparative HPLC using a C18 column, 250×50 mm, 10u, and eluting with a gradient of 20-100% $CH_3CN$ vs. 0.1% trifluoroacetic acid in water, giving the product as a trifluoroacetate salt. $^1H$ NMR (300 MHz, dimethylsulfoxide-$d_6$) δ 12.05 (br s, 1H), 8.79 (br s, 1H), 8.63 (m, 2H), 7.93 (dd, 1H), 7.78 (d, 2H), 7.26 (d, 1H), 6.90 (m, 2H), 4.90 (br m, 1H), 4.15 (br m, 1H), 3.90 (br m, 1H), 3.76 (br m, 1H), 3.26 (m, 4H), 3.12 (s, 2H), 2.08 (br m, 2H), 1.99 (br m, 5H), 1.60 (m, 18H), 1.18 (m, 3H), 1.00 (m, 2H).

Example 9

N-[(4-{[(2R)-4-(morpholin-4-yl)-1-(phenylthio)butan-2-yl]amino}-3-[(trifluoromethyl)sulfonyl]phenyl)sulfonyl]-4-(4-{(3-phenylpropanoyl)[(1S,2S,3S,5R)-2,6,6-trimethylbicyclo[3.1.1]hept-3-yl] amino}piperidin-1-yl)benzamide

Example 9A 4-((R)-3-Morpholin-4-yl-1-phenylsulfanylmethyl-propylamino)-3-trifluoromethanesulfonyl-benzenesulfonamide The title compound was prepared as described by Park, Cheol-Min; at. al *J. Med. Chem* 2008, 51, 6902-6915.

Example 9B

4-{-4-[3-Phenyl-propionyl)-((1S,2S,3S,5R)-2,6,6-trimethyl-bicyclo[3.1.1]hept-3-yl)-amino]-piperidin-1-yl}-benzoic Acid ethyl ester The title compound was prepared by substituting 3-phenylpropionyl chloride for acetyl chloride in EXAMPLE 2A.

Example 9C

4-{4-[(3-Phenyl-propionyl)-((1S,2S,3S,5R)-2,6,6-trimethyl-bicyclo[3.1.1]hept-3-yl)-amino]-piperidin-1-yl}-benzoic Acid The title compound was prepared by substituting EXAMPLE 9B for EXAMPLE 2A in EXAMPLE 2B.

Example 9D

N-[(4-{[(2R)-4-(morpholin-4-yl)-1-(phenylthio)butan-2-yl]amino}-3-[(trifluoromethyl)sulfonyl]phenyl)sulfonyl]-4-(4-{(3-phenylpropanoyl)[(1S,2S,3S,5R)-2,6,6-trimethylbicyclo[3.1.1]hept-3-yl]amino}piperidin-1-yl)benzamide The title compound was prepared by substituting EXAMPLE 9C for EXAMPLE 1A and EXAMPLE 9A for 4-chloro-3-nitrobenzenesulfonamide in EXAMPLE 1B. $^1$H NMR (300 MHz, dimethylsulfoxide-$d_6$) δ 8.10 (dd, 1H), 7.94 (dt, 1H), 7.72 (d, 2H), 7.39-7.13 (m, 10H), 6.97-6.78 (m, 4H), 4.20 (m, 1H), 4.04 (m, 1H), 3.88 (m, 2H), 3.51 (br s, 4H), 2.92-2.63 (m, 7H), 2.45-2.03 (m, 8H), 1.95 (m, 2H), 1.85-1.54 (m, 4H), 1.41 (m, 2H), 1.24-1.15 (m, 8H), 1.01-0.90 (m, 6H).

Example 10

4-{4-[adamantan-1-ylmethyl]piperazin-1-yl}-N-[(4-{[(2R)-4-(morpholin-4-yl)-1-(phenylthio)butan-2-yl]amino}-3-nitrophenyl)sulfonyl]benzamide

Example 10A

Ethyl 4-(piperazin-1-yl)benzoate

The title compound was prepared by the methods described in Bruncko, M., et. al., *J. Med. Chem.*, 2007 50, 641.

Example 10B

Ethyl 4-{4-[adamantan-1-ylcarbonyl]piperazin-1-yl}benzoate

The title compound was prepared by substituting EXAMPLE 10A for EXAMPLE 8B in EXAMPLE 8C.

Example 10C

Ethyl 4-{-4-[adamantan-1-ylmethyl]piperazin-1-yl}benzoate

The title compound was prepared by substituting EXAMPLE 10B for EXAMPLE 8C in EXAMPLE 8D.

Example 10D

4-{4-[adamantan-1-ylmethyl]piperazin-1-yl}benzoic Acid

The title compound was prepared by substituting EXAMPLE 10C for EXAMPLE 8D in EXAMPLE 8E.

Example 10E (R)-4-(4-morpholino-1-(phenylthio)butan-2-ylamino)-3-nitrobenzenesulfonamide The title compound was prepared by the methods described in Wendt, M., et. al., *J. Med. Chem.*, 2006, 49, 1165.

Example 10F

4-{4-[adamantan-1-ylmethyl]piperazin-1-yl}-N-[(4-{[(2R)-4-(morpholin-4-yl)-1-(phenylthio)butan-2-yl]amino}-3-nitrophenyl)sulfonyl]benzamide The title compound was prepared by substituting EXAMPLE 10D for EXAMPLE 8E and EXAMPLE 10E for EXAMPLE 2D in EXAMPLE 8F. $^1$H NMR (300 MHz, dimethylsulfoxide-$d_6$) δ 9.82 (v br s, 1H), 9.02 (v br s, 1H), 8.57 (d, 1H), 8.30 (d, 2H), 7.87 (dd, 1H), 7.80 (d, 2H), 7.23 (m, 2H), 7.16 (m, 4H), 7.01 (d, 2H), 4.20 (m, 2H), 3.90 (br m, 2H), 3.60, 3.40, 3.20, 3.00 (all br m, total 18H), 2.18 (m, 2H) 1.99 (br s, 3H), 1.62 (br m, 10H).

Example 11

4-{(1S,4S)-5-[adamantan-1-ylmethyl]-2,5-diazabicyclo[2.2.1]hept-2-yl}-N-({4-[(cyclohexylmethyl)amino]-3-nitrophenyl}sulfonyl)benzamide

Example 11A tert-butyl (1S,4S)-5-[4-(ethoxycarbonyl)phenyl]-2,5-diazabicyclo[2.2.1]heptane-2-carboxylate The title compound was prepared by substituting tert-butyl (1S,4S)-2,5-diazabicyclo[2.2.1]heptane-2-carboxylate for benzyl 2,6-diazabicyclo[3.2.1]octane-6-carboxylate in EXAMPLE 8A.

Example 11B

Ethyl 4-[(1S,4S)-2,5-diazabicyclo[2.2.1]hept-2-yl]benzoate

EXAMPLE 11A (280 mg) was dissolved in 4N HCl in dioxane (6 mL) and stirred at room temperature for one hour. The reaction was then partitioned between ethyl acetate and saturated NaHCO$_3$. The organic layer was washed with brine and dried over sodium sulfate. After filtration and concentration the resultant product was carried on with no purification.

Example 11C

Ethyl 4-{(1S,4S)-5-[adamantan-1-ylcarbonyl]-2,5-diazabicyclo[2.2.1]hept-2-yl}benzoate The title compound was prepared by substituting EXAMPLE 11B for EXAMPLE 8B in EXAMPLE 8C.

Example 11D

Ethyl 4-{(1S,4S)-5-[adamantan-1-ylmethyl]-2,5-diazabicyclo[2.2.1]hept-2-yl}benzoate The title compound was prepared by substituting EXAMPLE 11C for EXAMPLE 8C in EXAMPLE 8D.

Example 11E 4-{(1S,4S)-5-[adamantan-1-ylmethyl]-2,5-diazabicyclo[2.2.1]hept-2-yl}benzoic Acid The title compound was prepared by substituting EXAMPLE 11D for EXAMPLE 8D in EXAMPLE 8E.

Example 11F

4-{(1S,4S)-5-[adamantan-1-ylmethyl]-2,5-diazabicyclo[2.2.1]hept-2-yl}-N-({4-[(cyclohexylmethyl)amino]-3-nitrophenyl}sulfonyl)benzamide The title compound was prepared by substituting EXAMPLE 11E for EXAMPLE 8E in EXAMPLE 8F. $^1$H NMR (300 MHz, dimethylsulfoxide-$d_6$) δ 12.05 (br s, 1H), 8.63 (m, 2H), 8.20 (br s, 1H), 7.93 (dd, 1H), 7.78 (d, 2H), 7.26 (d, 1H), 6.70 (m, 2H), 4.78 (br s, 1H), 4.44 (br s, 1H), 3.70 (m, 2H), 3.38 (m, 2H), 3.30 (t, 2H), 3.12 (s, 2H), 2.38 (m, 1H), 2.20 (m, 1H), 1.99 (br m, 3H), 1.60 (m, 18H), 1.18 (m, 3H), 1.00 (m, 2H).

Example 12

4-(4-{[3-bromo-5-methyladamantan-1-yl]methyl}piperazin-1-yl)-N-({4-[(cyclohexylmethyl)amino]-3-nitrophenyl}sulfonyl)benzamide

Example 12A

Ethyl 4-(4-{[3-bromo-5-methyladamantan-1-yl]carbonyl}piperazin-1-yl)benzoate

The title compound was prepared by substituting EXAMPLE 10A for EXAMPLE 8B and 3-methyl-5-bromo-adamantane-1-carboxylic acid for adamantane-1-carboxylic acid in EXAMPLE 8C.

Example 12B

Ethyl 4-(4-{[3-bromo-5-methyladamantan-1-yl]methyl}piperazin-1-yl)benzoate

The title compound was prepared by substituting EXAMPLE 12A for EXAMPLE 8C in EXAMPLE 8D.

Example 12C 4-(4-{[3-bromo-5-methyladamantan-1-yl]methyl}piperazin-1-yl)benzoic Acid The title compound was prepared by substituting EXAMPLE 12B for EXAMPLE 8D in EXAMPLE 8E.

Example 12D 4-(4-{[3-bromo-5-methyl adamantan-1-yl]methyl}piperazin-1-yl)-N-({4-[(cyclohexylmethyl)amino]-3-nitrophenyl}sulfonyl)benzamide The title compound was prepared by substituting EXAMPLE 12C for EXAMPLE 8E in EXAMPLE 8F. $^1$H NMR (300 MHz, dimethylsulfoxide-$d_6$) δ 12.05 (v br s, 1H), 8.97 (v br s, 1H), 8.63 (m, 2H), 7.93 (dd, 1H), 7.80 (d, 2H), 7.25 (d, 1H), 7.00 (d, 2H), 3.90 (br m, 1H), 3.60, 3.40, 3.20, 3.00 (all br m, total 10H), 2.21 (s, 5H) 2.02 (m, 2H), 1.70 (m, 7H), 1.40 (m, 5H), 1.20 (m, 4H), 1.00 (m, 2H), 0.86 (s, 3H).

Example 13

N-({4-[(cyclohexylmethyl)amino]-3-nitrophenyl}sulfonyl)-4-(4-{[3,5-dimethyladamantan-1-yl]methyl}piperazin-1-yl)benzamide

Example 13A

Ethyl 4-(4-{[3,5-dimethyladamantan-1-yl]carbonyl}piperazin-1-yl)benzoate

The title compound was prepared by substituting EXAMPLE 10A for EXAMPLE 8B and 3,5-dimethyl-adamantane-1-carboxylic acid for adamantane-1-carboxylic acid in EXAMPLE 8C.

Example 13B

Ethyl 4-(4-{[3,5-dimethyladamantan-1-yl]methyl}piperazin-1-yl)benzoate

The title compound was prepared by substituting EXAMPLE 13A for EXAMPLE 8C in EXAMPLE 8D.

Example 13C 4-(4-{[3,5-dimethyladamantan-1-yl]methyl}piperazin-1-yl)benzoic Acid The title compound was prepared by substituting EXAMPLE 13B for EXAMPLE 8D in EXAMPLE 8E.

Example 13D

N-({4-[(cyclohexylmethyl)amino]-3-nitrophenyl}sulfonyl)-4-(4-{[3,5-dimethyladamantan-1-yl]methyl}piperazin-1-yl)benzamide The title compound was prepared by substituting EXAMPLE 13C for EXAMPLE 8E in EXAMPLE 8F. $^1$H NMR (300 MHz, dimethylsulfoxide-$d_6$) δ 12.05 (v br s, 1H), 8.97 (v br s, 1H), 8.63 (m, 2H), 7.93 (dd, 1H), 7.80 (d, 2H), 7.25 (d, 1H), 7.00 (d, 2H), 3.90 (br m, 1H), 3.55 (br m, 1H), 3.30 (m, 8H), 2.99 (br s, 2H), 2.08 (br m, 1H), 1.70 (m, 7H), 1.45 (s, 2H), 1.20 (m, 12H), 1.00 (m, 2H), 0.82 (s, 6H).

Example 14

4-{4-[(4'-chlorobiphenyl-2-yl)methyl]piperazin-1-yl}-N-{[4-(1-methyl-2-oxo-3-azabicyclo[3.1.1]hept-3-yl)phenyl]sulfonyl}benzamide EXAMPLE 14 was prepared according to the procedure for EXAMPLE 1B substituting 4-(1-methyl-2-oxo-3-azabicyclo[3.1.1]heptan-3-yl)benzenesulfonamide for 4-chloro-3-nitrobenzenesulfonamide. $^1$H NMR (300 MHz, dimethylsulfoxide-$d_6$) δ ppm 1.45 (s, 3H), 1.56 (dd, 1H), 1.92-1.98 (m, 1H), 2.63 (dd, 1H), 2.69-2.75 (m, 1H), 2.79-2.99 (m, 2H), 3.01-3.21 (m, 4H), 3.30-3.35 (m, 4H), 3.78-4.01 (m, 1H), 4.39 (s, 2H), 6.88-6.95 (m, 2H), 7.29-7.36 (m, 1H), 7.38-7.44 (m, 2H), 7.47-7.58 (m, 6H), 7.72-7.79 (m, 3H), 7.99-8.06 (m, 2H), 9.45-9.59 (m, 1H).

Example 15

N-({3-nitro-4-[(tetrahydro-2H-pyran-4-ylmethyl) amino]phenyl}sulfonyl)-4-(4-{2-[(1R,4R)-1,7,7-trimethylbicyclo[2.2.1]hept-2-en-2-yl] benzyl}piperazin-1-yl)benzamide

Example 15A

Ethyl 4-(4-{2-[(1R,4R)-1,7,7-trimethylbicyclo[2.2.1] hept-2-en-2-yl]benzyl}piperazin-1-yl)benzoate EXAMPLE 62A (100 mg), (1S,4R)-1,7,7-trimethylbicyclo[2.2.1]hept-2-en-2-ylboronic acid (44.6 mg), tris(dibenzylideneacetone)dipalladium(0) (11 mg), tri-t-butylphosphonium tetrafluoroborate (4 mg) and CsF (113 mg) were dissolved in anhydrous tetrahydrofuran (2 mL). The reaction mixture was stirred at room temperature overnight. The reaction mixture was concentrated, and the crude material was purified using flash chromatography with 0-15% ethyl acetate/hexane to afford the title compound.

Example 15B 4-(4-{2-[(1R,4R)-1,7,7-trimethylbicyclo[2.2.1]hept-2-en-2-yl]benzyl}piperazin-1-yl)benzoic acid The title compound was prepared by substituting EXAMPLE 15A for EXAMPLE 2A in EXAMPLE 2B.

Example 15C

N-({3-nitro-4-[(tetrahydro-2H-pyran-4-ylmethyl) amino]phenyl}sulfonyl)-4-(4-{2-[(1R,4R)-1,7,7-trimethylbicyclo[2.2.1]hept-2-en-2-yl] benzyl}piperazin-1-yl)benzamide The title compound was prepared by substituting EXAMPLE 15B for EXAMPLE 1A and EXAMPLE 23A for 4-chloro-3-nitrobenzenesulfonamide in EXAMPLE 1B. $^1$H NMR (400 MHz, dimethylsulfoxide-$d_6$) δ 12.12 (m, 1H), 8.66 (m, 2H), 7.94 (dd, 1H), 7.79 (d, 2H), 7.64 (m, 1H), 7.41 (m, 2H), 7.30 (d, 1H), 7.20 (m, 1H), 6.99 (d, 2H), 6.01 (d, 1H), 4.28 (m, 2H), 3.85 (m, 2H), 3.28 (m, 12H), 1.92 (m, 2H), 1.62 (m, 3H), 1.24 (m, 5H), 0.94 (s, 3H), 0.83 (d, 6H).

Example 16

N-({3-nitro-4-[(tetrahydro-2H-pyran-4-ylmethyl) amino]phenyl}sulfonyl)-4-(4-{2-octahydro-1H-4,7-methanoinden-5-ylamino]benzyl}piperazin-1-yl) benzamide

Example 16A

Ethyl 4-(4-(2-nitrobenzyl)piperazin-1-yl)benzoate

Ethyl 4-(piperazin-1-yl)benzoate (1.5 g), 1-(bromomethyl)-2-nitrobenzene (1.383 g) and sodium carbonate (2.036 g) were suspended in anhydrous N,N-dimethylformamide (20 mL) at room temperature for 4 hours. The reaction mixture was diluted with ethyl acetate, washed with water and brine, and concentrated. The residue was purified by flash column purification with 10-40% ethyl acetate/hexane to afford the title compound.

Example 16B

Ethyl 4-(4-(2-aminobenzyl)piperazin-1-yl)benzoate

EXAMPLE 16A (1.5 g) and 5% Pd/C (0.3 g) were suspended in anhydrous ethanol (75 mL). The reaction mixture was stirred under 1 atmosphere hydrogen for 2 hours. The mixture was filtered, and the filtrate was concentrated to afford the product.

Example 16C

Ethyl 4-(4-{2-[octahydro-1H-4,7-methanoinden-5-ylamino]benzyl}piperazin-1-yl)benzoate The title compound was prepared by substituting tricyclo [5.2.1.0²,⁶]decan-8-one for 2-formylphenylboronic acid and EXAMPLE 16B for EXAMPLE 23C in EXAMPLE 40A.

Example 16D 4-(4-{2-[octahydro-1H-4,7-methanoinden-5-ylamino]benzyl}piperazin-1-yl)benzoic Acid The title compound was prepared by substituting EXAMPLE 16C for EXAMPLE 2A in EXAMPLE 2B.

Example 16E

N-({3-nitro-4-[(tetrahydro-2H-pyran-4-ylmethyl) amino]phenyl}sulfonyl)-4-(4-{2-[octahydro-1H-4,7-methanoinden-5-ylamino]benzyl}piperazin-1-yl) benzamide The title compound was prepared by substituting EXAMPLE 16D for EXAMPLE 1A and EXAMPLE 23A for 4-chloro-3-nitrobenzenesulfonamide in EXAMPLE 1B. $^1$H NMR (400 MHz, dimethylsulfoxide-$d_6$) δ 12.09 (bs, 1H), 8.66 (m, 2H), 7.94 (dd, 1H), 7.79 (d, 2H), 7.30 (d, 1H), 7.22 (t, 2H), 7.01 (m, 2H), 6.72 (d, 1H), 6.65 (m, 1H), 4.26 (m, 2H), 3.85 (dd, 2H), 3.66 (m, 2H), 3.28 (m, 10H), 2.26-1.61 (m, 14H), 1.40-0.92 (m, 8H).

Example 17

N-({3-nitro-4-[(tetrahydro-2H-pyran-4-ylmethyl) amino]phenyl}sulfonyl)-4-[4-(2-{[(1R,4R,6S)-5,5,6-trimethylbicyclo[2.2.1]hept-2-yl]amino}benzyl)piperazin-1-yl]benzamide

Example 17A

Ethyl 4-(4-(2-((1R,4R,6S)-5,5,6-trimethylbicyclo [2.2.1]heptan-2-ylamino)benzyl)piperazin-1-yl)benzoate The title compound was prepared by substituting (1R,4R, 6S)-5,5,6-trimethylbicyclo[2.2.1]heptan-2-one for 2-formylphenylboronic acid and EXAMPLE 16B for EXAMPLE 23C in EXAMPLE 40A.

Example 17B

Ethyl 4-(4-(2-((1R,4R,6S)-5,5,6-trimethylbicyclo[2.2.1]heptan-2-ylamino)benzyl)piperazin-1-yl)benzoate The title compound was prepared by substituting EXAMPLE 17A for EXAMPLE 2A in EXAMPLE 2B.

Example 17C

N-({3-nitro-4-[(tetrahydro-2H-pyran-4-ylmethyl)amino]phenyl}sulfonyl)-4-[4-(2-{[(1R,4R,6S)-5,5,6-trimethylbicyclo[2.2.1]hept-2-yl]amino}benzyl)piperazin-1-yl]benzamide The title compound was prepared by substituting EXAMPLE 17B for EXAMPLE 1A and EXAMPLE 23A for 4-chloro-3-nitrobenzenesulfonamide in EXAMPLE 1B. $^1$H NMR (400 MHz, dimethylsulfoxide-$d_6$) δ 12.06 (bs, 1H), 8.64 (m, 2H), 7.94 (m, 1H), 7.79 (d, 2H), 7.30 (d, 1H), 7.20 (m, 2H), 7.00 (d, 2H), 6.65 (m, 2H), 3.83 (m, 2H), 3.61 (m, 2H), 3.30 (m, 14H), 2.05 (s, 1H), 1.86 (m, 3H), 1.61 (m, 4H), 1.45 (m, 1H), 1.28 (m, 3H), 0.99 (s, 3H), 0.86 (s, 3H), 0.77 (d, 3H).

Example 18

4-[4-(2-[(1R,5S)-6,6-dimethylbicyclo[3.1.1]hept-2-yl]amino benzyl)piperazin-1-yl]-N-({3-nitro-4-[(tetrahydro-2H-pyran-4-ylmethyl)amino]phenyl}sulfonyl)benzamide

Example 18A

Ethyl 4-(4-(2-((1R,5S)-6,6-dimethylbicyclo[3.1.1]heptan-2-ylamino)benzyl)piperazin-1-yl)benzoate The title compound was prepared by substituting (1R,5S)-6,6-dimethylbicyclo[3.1.1]heptan-2-one for 2-formylphenylboronic acid and EXAMPLE 16B for EXAMPLE 23C in EXAMPLE 40A.

Example 18B 4-(4-(2-((1R,5S)-6,6-dimethylbicyclo[3.1.1]heptan-2-ylamino)benzyl)piperazin-1-yl)benzoic acid The title compound was prepared by substituting EXAMPLE 18A for EXAMPLE 2A in EXAMPLE 2B.

Example 18C

4-[4-(2-{[(1R,5S)-6,6-dimethylbicyclo[3.1.1]hept-2-yl]amino}benzyl)piperazin-1-yl]-N-({3-nitro-4-[(tetrahydro-2H-pyran-4-ylmethyl)amino]phenyl}sulfonyl)benzamide The title compound was prepared by substituting EXAMPLE 18B for EXAMPLE 1A and EXAMPLE 23A for 4-chloro-3-nitrobenzenesulfonamide in EXAMPLE 1B. $^1$H NMR (400 MHz, dimethylsulfoxide-$d_6$) δ 12.09 (s, 1H), 8.66 (m, 2H), 7.94 (dd, 1H), 7.79 (d, 2H), 7.30 (d, 1H), 7.19 (m, 2H), 6.99 (d, 2H), 6.59 (m, 2H), 3.85 (m, 4H), 3.29 (m, 14H), 2.33 (m, 2H), 2.17 (m, 1H), 1.82 (m, 7H), 1.27 (dd, 2H), 1.18 (s, 3H), 1.09 (s, 3H), 1.03 (d, 1H).

Example 19

4-(4-{[(1R,5R)-2-(4-chlorophenyl)-6,6-dimethylbicyclo[3.1.1]hept-2-en-3-yl]methyl}piperazin-1-yl)-N-({4-[(cyclohexylmethyl)amino]-3-nitrophenyl}sulfonyl)benzamide

Example 19A (1R,5R)-6,6-Dimethyl-3-methylene-bicyclo[3.1.1]heptan-2-one (1R,5S)-6,6-Dimethylbicyclo[3.1.1]heptan-2-one (0.938 mL, 920 mg) was added to tetrahydrofuran (50 mL) and the mixture was cooled to −78° C. using an isopropanol/dry ice bath. Lithium bis(trimethylsilyl)amide (1M in tetrahydrofuran, 7.99 mL) was added, and the solution was stirred at −78° C. for 15 minutes. The solution was allowed to warm to 0° C. in a water/ice bath and the mixture was stirred for 45 minutes. Paraformaldehyde (2000 mg) was added. The solution was stirred at 0° C. for 15 minutes, allowed to warm to room temperature and stir for an additional four hours. The reaction was quenched with saturated aqueous ammonium chloride, extracted with diethyl ether, washed with brine, dried over anhydrous sodium sulfate, filtered, concentrated, and purified by flash column chromatography on silica gel using 5% ethyl acetate in hexanes.

Example 19B

4-[4-((1R,5R)-6,6-Dimethyl-2-oxo-bicyclo[3.1.1]hept-3-ylmethyl)-piperazin-1-yl]-benzoic acid ethyl ester EXAMPLE 19A (417 mg) and ethyl 4-(piperazin-1-yl)benzoate (520 mg) were added to acetonitrile (6 mL). Bismuth (III) trifluoromethanesulfonate (113 mg) was added, and the mixture was heated at 50° C. for 5.5 hours. The mixture was cooled and purified by flash column chromatography on silica gel using 5% methanol in dichloromethane.

Example 19C

4-{4-[(1R,5R)-2-(4-Chloro-phenyl)-2-hydroxy-6,6-dimethyl-bicyclo[3.1.1]hept-3-ylmethyl]-piperazin-1-yl}-benzoic Acid ethyl ester EXAMPLE 19B (452 mg) was dissolved in tetrahydrofuran (10 mL) and the mixture was cooled to −60° C. using a chloroform/dry ice bath. (4-Chlorophenyl)magnesium bromide (1M in tetrahydrofuran, 2.35 mL) was added drop-wise. Upon completion of the addition, the mixture was warmed quickly to −25° C. using a carbon tetrachloride/dry ice bath and stirred for four hours. The reaction was quenched with saturated aqueous ammonium chloride, extracted with ethyl acetate, dried on anhydrous sodium sulfate, and purified by flash column chromatography on silica gel using 20% ethyl acetate in hexanes.

Example 19D

4-{4-[(1R,5R)-2-(4-Chloro-phenyl)-6,6-dimethyl-bicyclo[3.1.1]hept-2-en-3-ylmethyl]-piperazin-1-yl}-benzoic Acid ethyl ester EXAMPLE 19C (363 mg) was dissolved in tetrahydrofuran (6 mL) and Burgess reagent ((methoxycarbonylsulfamoyl)triethylammonium hydroxide, inner salt, 209 mg) was added. The solution was stirred at room temperature for 16 hours and purified by flash column chromatography on silica gel using 20% ethyl acetate in hexanes.

Example 19E

4-{4-[(1R,5R)-2-(4-Chloro-phenyl)-6,6-dimethyl-bicyclo[3.1.1]hept-2-en-3-ylmethyl]-piperazin-1-yl}-benzoic Acid The title compound was prepared by substituting EXAMPLE 19D for EXAMPLE 2A in EXAMPLE 2B.

Example 19F 4-(4-{[(1R,5R)-2-(4-chlorophenyl)-6,6-dimethylbi-cyclo[3.1.1]hept-2-en-3-yl]methyl}piperazin-1-yl)-N-({4-[(cyclohexylmethyl)amino]-3-nitrophenyl}sulfonyl)benzamide The title compound was prepared by substituting EXAMPLE 19E for EXAMPLE 1A and EXAMPLE 2D for 4-chloro-3-nitrobenzenesulfonamide in EXAMPLE 1B. $^1$H NMR (300 MHz, dimethylsulfoxide-$d_6$) δ 8.56 (m, 1H), 8.48 (m, 1H), 7.90 (dd, 1H), 7.76 (d, 2H), 7.48 (d, 1H), 7.40 (d, 1H), 7.14 (d, 1H), 6.91 (d, 2H), 6.88 (d, 1H), 6.42 (d, 1H), 4.14 (dd, 1H), 3.26 (m, 8H), 2.71 (br s, 2H), 1.95 (m, 2H), 1.77-1.53 (m, 8H), 1.33-1.11 (m, 6H), 1.07 (s, 3H), 0.97 (s, 3H), 0.86 (m, 2H).

Example 20

4-{4-[(2-{[adamantan-2-ylmethyl]amino}-5,5-dim-ethylcyclohexyl)methyl]piperazin-1-yl}-N-({3-nitro-4-[(tetrahydro-2H-pyran-4-ylmethyl)amino]phenyl}sulfonyl)benzamide Example 20A Ethyl 4-[4-({2-[(adamantan-2-ylmethyl)amino]-5,5-dimethylcyclohexyl}methyl)piperazin-1-yl]benzoate (2-Adamantylmethyl)amine hydrochloride salt (195 mg), ethyl 4-(4-((5,5-dimethyl-2-oxocyclohexypmethyl)piper-azin-1-yl)benzoate (200 mg) and sodium acetate (44 mg) were suspended in anhydrous dichloroethane. The reaction mixture was stirred at room temperature for 20 minutes, followed by the addition of sodium triacetoxyborohydride (228 mg). The reaction mixture was stirred at room temperature overnight. The reaction was quenched with saturated NaHCO$_3$ aqueous solution. The reaction mixture was extracted with ethyl acetate, and washed with water and brine. The organic phase was dried over Na$_2$SO$_4$, filtered, and concentrated. The residue was purified by flash column purification with 0-5% methanol/dichloromethane to afford the title compound.

Example 20B

4-[4-({2-[(adamantan-2-ylmethyl)amino]-5,5-dimethylcyclohexyl}methyl)piperazin-1-yl]benzoic acid The title compound was prepared by substituting EXAMPLE 20A for EXAMPLE 2A in EXAMPLE 2B.

Example 20C

4-{4-[(2-{[adamantan-2-ylmethyl]amino}-5,5-dim-ethylcyclohexyl)methyl]piperazin-1-yl}-N-({3-nitro-4-[(tetrahydro-2H-pyran-4-ylmethyl)amino]phenyl}sulfonyl)benzamide The title compound was prepared by substituting EXAMPLE 20B for EXAMPLE 1A and EXAMPLE 23A for 4-chloro-3-nitrobenzenesulfonamide in EXAMPLE 1B. $^1$H NMR (400 MHz, dimethylsulfoxide-$d_6$) δ 12.05 (s, 1H), 8.65 (m, 2H), 7.94 (dd, 1H), 7.78 (d, 2H), 7.30 (d, 1H), 6.99 (d, 2H), 3.83 (m, 2H), 3.26 (m, 8H), 2.98 (m, 4H), 2.72 (m, 4H), 2.27 (m, 2H), 1.64 (m, 22H), 1.25 (m, 5H), 0.93 (d, 6H).

Example 21

4-{4-[(5,5-dimethyl-2-{[(1R,2S,3S,5S)-2,6,6-trim-ethylbicyclo[3.1.1]hept-3-yl]amino}cyclohexyl)me-thyl]piperazin-1-yl}-N-({3-nitro-4-[(tetrahydro-2H-pyran-4-ylmethyl)amino]phenyl}sulfonyl)benzamide Example 21A Ethyl 4-(4-((5,5-dimethyl-2-((1R,2S,3S,5S)-2,6,6-trimethylbicyclo[3.1.1]heptan-3-ylamino)cyclo-hexyl)methyl)piperazin-1-yl)benzoate The title compound was prepared by substituting (1R,2S,3S,5S)-2,6,6-trimethylbicyclo[3.1.1]heptan-3-amine for (2-adamantylmethyl)amine hydrochloride salt in EXAMPLE 20B.

Example 21B 4-(4-((5,5-dimethyl-2-((1R,2S,3S,5S)-2,6,6-trimeth-ylbicyclo[3.1.1]heptan-3-ylamino)cyclohexyl)me-thyl)piperazin-1-yl)benzoic Acid The title compound was prepared by substituting EXAMPLE 21A for EXAMPLE 2A in EXAMPLE 2B.

Example 21C

4-{4-[(5,5-dimethyl-2-{[(1R,2S,3S,5S)-2,6,6-trim-ethylbicyclo[3.1.1]hept-3-yl]amino}cyclohexyl)me-thyl]piperazin-1-yl}-N-({3-nitro-4-[(tetrahydro-2H-pyran-4-ylmethyl)amino]phenyl}sulfonyl)benzamide The title compound was prepared by substituting EXAMPLE 21B for EXAMPLE 1A and EXAMPLE 23A for 4-chloro-3-nitrobenzenesulfonamide in EXAMPLE 1B. $^1$H NMR (400 MHz, dimethylsulfoxide-$d_6$) δ 12.07 (m, 1H), 8.65 (m, 2H), 7.94 (dd, 1H), 7.77 (m, 2H), 7.30 (d, 1H), 6.98 (d, 2H), 3.84 (dd, 2H), 3.29 (m, 10H), 2.79 (m, 6H), 2.30 (m, 4H), 1.78 (m, 11H), 1.28 (m, 3H), 1.16 (m, 8H), 0.95 (m, 9H).

Example 22

4-{4-[2-(3-azabicyclo[3.2.2]non-3-yl)-5-nitrobenzyl] piperazin-1-yl}N-({3-nitro-4-[(tetrahydro-2H-pyran-4-ylmethyl)amino]phenyl}sulfonyl)benzamide

Example 22A tert-butyl 4-(4-(methoxycarbonyl)phenyl)piperazine-1-carboxylate The title compound was prepared as described in EXAMPLE 45A using tert-butyl piperazine-1-carboxylate in place of 1,4-dioxa-8-azaspiro[4.5]decane.

Example 22B 4-(4-(tert-butoxycarbonyl)piperazin-1-yl)benzoic Acid

The title compound was prepared as described in EXAMPLE 2B using EXAMPLE 22A in place of EXAMPLE 2A.

Example 22C tert-butyl 4-(4-(4-(cyclohexylmethylamino)-3-nitrophenylsulfonylcarbamoyl)phenyl)piperazine-1-carboxylate The title compound was prepared as described in EXAMPLE 1B using EXAMPLE 22B in place of EXAMPLE 1A and EXAMPLE 2D in place of 4-chloro-3-nitrobenzenesulfonamide.

Example 22D

N-(4-(cyclohexylmethylamino)-3-nitrophenylsulfonyl)-4-(piperazin-1-yl)benzamide Trifluoroacetic Acid Salt A solution of EXAMPLE 22C (0.85 g, 1.4 mmol) in dichloromethane (10 mL), trifluoroacetic acid (10 mL) and triethylsilane (1 mL) was stirred for 24 hours. The mixture was concentrated to afford the title compound.

Example 22E

4-{4-[2-(3-azabicyclo[3.2.2]non-3-yl)-5-nitrobenzyl] piperazin-1-yl}-N-({3-nitro-4-[(tetrahydro-2H-pyran-4-ylmethyl)amino]phenyl}sulfonyl)benzamide EXAMPLE 22D (50 mg, 0.081 mmol), 2-((1s,5s)-3-azabicyclo[3.2.2]nonan-3-yl)-5-nitrobenzaldehyde (27 mg, 0.097 mmol), and polymer-supported sodium cyanoborohydride (41 mg, 0.097 mmol) was stirred in tetrahydrofuran (1 mL) and acetic acid (0.33 mL) for 24 hours. The crude mixture was chromatographed on silica gel using 10% methanol in ethyl acetate, without and then with 1% triethylamine, to afford the title compound. MS (ELSD) m/e 762 (M+H)$^+$.

Example 23

4-(4-{2-[2,3,3a,4,7,7a-hexahydro-1H-4,7-methanoinden-5-yl]benzyl}piperazin-1-yl)-N-({3-nitro-4-[(tetrahydro-2H-pyran-4-ylmethyl)amino] phenyl}sulfonyl)benzamide

Example 23A

3-Nitro-4-[(tetrahydro-pyran-4-ylmethyl)-amino]-benzenesulfonamide

The title compound was prepared by substituting 4-aminomethyltetrahydropyran for cyclohexylmethylamine in EXAMPLE 2D.

Example 23B 4-(4-{3-Nitro-4-[(tetrahydro-pyran-4-ylmethyl)-amino]-benzenesulfonylaminocarbonyl}-phenyl)-piperazine-1-carboxylic Acid Tert-butyl Ester The title compound was prepared by substituting 4-(4-carboxy-phenyl)-piperazine-1-carboxylic acid tert-butyl ester for EXAMPLE 1A and EXAMPLE 23A for 4-chloro-3-nitrobenzenesulfonamide in EXAMPLE 1B.

Example 23C

N-({3-nitro-4-[(tetrahydro-2H-pyran-4-ylmethyl) amino]phenyl}sulfonyl)-4-(piperazin-1-yl)benzamide EXAMPLE 23B (3.813 g) was added to dichloromethane (50 mL). Triethylsilane (5.5 mL, 4.004 g) was added, followed by trifluoroacetic acid (6 mL, 8.880 g). The solution was stirred at room temperature for five hours. Heptane was added and the solvents were removed under reduced pressure, after which, toluene was added and the solvents again removed under reduced pressure to isolate the title compound as the mono trifluoroacetic acid salt.

Example 23D 2,3,3a,4,7,7a-hexahydro-1H-4,7-methanoinden-5-yl trifluoromethanesulfonate Tricyclo[5.2.1.02,6]decan-8-one (300 mg) was added to tetrahydrofuran (10 mL).

Sodium bis(trimethylsilyl)amide (1M in tetrahydrofuran, 2.40 mL) was added, and the solution was stirred at room temperature for 10 minutes. The solution was cooled to −78° C. using an isopropanol/dry ice bath, and 1,1,1-trifluoro-N-phenyl-N-(trifluoromethylsulfonyl)methanesulfonamide (857 mg) was added. The solution was allowed to warm to room temperature and stirred for 16 hours. The reaction mixture was concentrated, diluted with hexanes (20 mL), filtered and again concentrated. The residue was purified by flash column chromatography on silica gel using a gradient of 0 to 10% ethyl acetate in hexanes.

Example 23E 2-(2,3,3a,4,7,7a-Hexahydro-1H-4,7-methano-inden-5-yl)-benzaldehyde EXAMPLE 23D (941 mg), 2-formylphenylboronic acid (600 mg), potassium phosphate, tribasic (1416 mg), and [1,1'- bis(diphenylphosphino)ferrocene]dichloropalladium(II) (244 mg) were added to tetrahydrofuran (15 mL) which had been degassed and flushed with nitrogen three times. The solution was heated to 60° C. and stirred for 16 hours. The solution was concentrated and purified by flash column chromatography on silica gel using 10% ethyl acetate in hexanes.

Example 23F 4-(4-{2-[2,3,3a,4,7,7a-hexahydro-1H-4,7-methanoinden-5-yl]benzyl}piperazin-1-yl)-N-({3-nitro-4-[(tetrahydro-2H-pyran-4-ylmethyl)amino]phenyl}sulfonyl)benzamide EXAMPLE 23C (60 mg) and EXAMPLE 23E (26 mg) were added to tetrahydrofuran (1 mL) and acetic acid (0.33 mL). Sodium cyanoborohydride (2.38 mmol/g on resin, 45 mg) was added and the solution was stirred at room temperature for 16 hours. The solution was purified by flash column chromatography on silica gel using 5% methanol in dichloromethane to isolate the title compound as the mono acetic acid salt. $^1$H NMR (300 MHz, dimethylsulfoxide-$d_6$) δ 11.94 (br s, 1H), 8.63 (t, 1H), 8.62 (d, 1H), 7.93 (dd, 1H), 7.73 (d, 2H), 7.42 (d, 1H), 7.28-7.20 (m, 4H), 6.92 (d, 2H), 6.25 (d, 1H), 3.85 (dd, 4H), 3.60-3.41 (m, 6H), 3.37-3.26 (m, 8H), 3.22 (br s, 2H), 2.75 (br s, 2H), 2.64 (br s, 2H), 2.13 (m, 4H), 1.95-1.76 (m, 6H), 1.91 (s, 3H), 1.64-1.50 (m, 6H), 1.32-1.19 (m, 3H), 1.03 (m, 2H).

Example 24

1-[adamantan-1-yl]-4-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}-N,N-diphenyl-1H-pyrazole-3-carboxamide

Example 24A

1-[adamantan-1-yl]-4-(2-formylphenyl)-N,N-diphenyl-1H-pyrazole-3-carboxamide

1-Adamantan-1-yl-4-bromo-1H-pyrazole-3-carboxylic acid diphenylamide (47 mg), 2-formylphenylboronic acid (18 mg), sodium carbonate (32 mg), and tetrakis(triphenylphosphine)palladium(0) (7 mg) were combined in dimethoxyethane/ethanol/water 12/3/4 (1 mL) and heated in a CEM Discover microwave reactor at 180° C. for 5 minutes. The reaction was cooled, diluted with water and extracted with ethyl acetate. The organic layer was washed with brine and dried over sodium sulfate. After filtration and concentration, the crude material was purified by column chromatography on silica gel using hexanes/ethyl acetate 4/1.

Example 24B

1-[adamantan-1-yl]-4-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}-N,N-diphenyl-1H-pyrazole-3-carboxamide The title compound was prepared by substituting EXAMPLE 24A for 2-formylphenylboronic acid in EXAMPLE 40A, except here product was purified by preparative HPLC using a C18 column, 250×50 mm, 10μ, and eluting with a gradient of 20-100% CH$_3$CN vs. 0.1% trifluoroacetic acid in water, giving the product as a trifluoroacetate salt. $^1$H NMR (300 MHz, dimethylsulfoxide-$d_6$) δ 9.70 (br s, 1H), 8.70 (t, 1H), 8.66 (d, 1H), 7.96 (dd, 1H), 7.89 (br s, 1H), 7.80 (d, 2H), 7.63 (br s, 1H), 7.50 (br s, 2H), 7.32 (m, 6H), 7.19 (m, 6H), 6.98 (d, 2H), 4.15 (br s, 1H) 3.80 (m, 4H), 3.40, (m, 4H), 3.25 (m, 4H), 2.97 (br s, 1H), 2.00, 1.80, 1.60 (all m, total 18H), 1.24 (m, 4H).

Example 25

4-(4-{2-[2-(adamantan-1-yl)-6-methylimidazo[1,2-a]pyridin-8-yl]benzyl}piperazin-1-yl)-N-({3-nitro-4-[(tetrahydro-2H-pyran-4-ylmethyl)amino]phenyl}sulfonyl)benzamide $^1$H NMR (400 MHz, dimethylsulfoxide-$d_6$) δ ppm 12.05 (s, 1H), 8.55-8.74 (m, 3H), 8.07 (s, 1H), 7.93 (dd, 1H), 7.73 (d, 2H), 7.55-7.71 (m, 4H), 7.48 (d, 1H), 7.29 (d, 1H), 6.86 (d, 2H), 3.81-3.89 (m, 4H), 3.31-3.38 (m, 2H), 3.22-3.30 (m, 2H), 2.42 (s, 3H), 2.03 (s, 3H), 1.91 (d, 8H), 1.56-1.77 (m, 10H), 1.20-1.32 (m, 3H). MS (ESI) m/e 856 (M−H)$^-$.

Example 26

N-(adamantan-2-yl)-6-methyl-8-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}imidazo[1,2-a]pyridine-2-carboxamide $^1$H NMR (400 MHz, dimethylsulfoxide-$d_6$) δ ppm 12.10 (s, 1H), 8.75 (s, 1H), 8.62-8.69 (m, 2H), 8.57 (s, 1H), 7.88-7.98 (m, 2H), 7.81 (d, J=8.9 Hz, 2H), 7.67-7.73 (m, 1H), 7.60-7.67 (m, 2H), 7.46-7.52 (m, 1H), 7.26-7.33 (m, 2H), 6.97 (d, J=9.2 Hz, 2H), 4.25 (s, 2H), 3.80-3.91 (m, 4H), 3.35 (t, J=6.4 Hz, 3H), 3.16-3.31 (m, 6H), 2.40 (s, 3H), 1.85-2.02 (m, 3H), 1.82 (s, 2H), 1.76 (s, 1H), 1.54-1.71 (m, 8H), 1.45 (d, J=12.6 Hz, 2H), 1.19-1.33 (m, 2H). MS (ESI) m/e 856 (M−H)$^-$.

Example 27

4-(4-{2-[(1R,5S)-6,6-dimethylbicyclo[3.1.1]hept-2-en-2-yl]benzyl}piperazin-1-yl)-N-({3-nitro-4-[(tetrahydro-2H-pyran-4-ylmethyl)amino]phenyl}sulfonyl)benzamide

Example 27A 6,6-dimethylbicyclo[3.1.1]hept-2-en-2-yl trifluoromethanesulfonate The title compound was prepared by substituting (1R)-(+)-nopinone for tricyclo[5.2.1.0$^{2,6}$]decan-8-one in EXAMPLE 23D.

Example 27B 2-(6,6-Dimethyl-bicyclo[3.1.1]hept-2-en-2-yl)-benzaldehyde

The title compound was prepared by substituting EXAMPLE 27A for EXAMPLE 23D in EXAMPLE 23E.

Example 27C 4-(4-{2-[6,6-dimethylbicyclo[3.1.1]hept-2-en-2-yl]benzyl}piperazin-1-yl)-N-({3-nitro-4-[(tetrahydro-2H-pyran-4-ylmethyl)amino]phenyl}sulfonyl)benzamide The title compound was prepared by substituting EXAMPLE 27B for EXAMPLE 23E in EXAMPLE 23F. $^1$H NMR (300 MHz, dimethylsulfoxide-$d_6$) δ 11.94 (br s, 1H), 8.63 (t, 1H), 8.62 (d, 1H), 7.93 (dd, 1H), 7.74 (d, 2H), 7.47-7.35 (m, 2H), 7.24 (m, 2H), 7.03 (m, 1H), 6.92 (d, 2H), 5.55 (1H), 3.85 (dd, 2H), 3.63-3.41 (m, 2H), 3.37-3.23 (m, 8H), 2.41 (m, 2H), 2.37-2.29 (m, 4H), 2.15 (m, 2H), 1.91 (s, 3H), 1.62 (d, 2H), 1.40 (d, 1H), 1.30 (s, 3H), 1.26 (m, 4H), 0.98 (s, 3H).

Example 28

N-({3-nitro-4-[(tetrahydro-2H-pyran-4-ylmethyl)amino]phenyl}sulfonyl)-4-(4-{2-[5,5,6-trimethylbicyclo[2.2.1]hept-2-en-2-yl]benzyl}piperazin-1-yl)benzamide

Example 28A 5,5,6-trimethylbicyclo[2.2.1]hept-2-en-2-yl trifluoromethanesulfonate The title compound was prepared by substituting 5,5,6-trimethylbicyclo[2.2.1]heptan-2-one for tricyclo[5.2.1.0$^{2,6}$]decan-8-one in EXAMPLE 23D.

Example 28B

The title compound was prepared by substituting EXAMPLE 28A for EXAMPLE 23D in EXAMPLE 23E.

Example 28C

N-({3-nitro-4-[(tetrahydro-2H-pyran-4-ylmethyl)amino]phenyl}sulfonyl)-4-(4-{2-[5,5,6-trimethylbicyclo[2.2.1]hept-2-en-2-yl]benzyl}piperazin-1-yl)benzamide The title compound was prepared by substituting EXAMPLE 28B for EXAMPLE 23E in EXAMPLE 23F. $^1$H NMR (300 MHz, dimethylsulfoxide-$d_6$) δ 11.93 (br s, 1H), 8.60 (m, 2H), 7.93 (d, 1H), 7.74 (d, 2H), 7.44 (m, 1H), 7.27-7.17 (m, 4H), 6.90 (d, 2H), 6.20 (br s, 1H), 3.85 (dd, 2H), 3.56 (m, 2H), 3.36-3.23 (m, 8H), 2.62 (br s, 2H), 2.42 (br s, 2H), 1.91 (br s, 3H), 1.82 (d, 2H), 1.62 (dd, 2H), 1.52 (d, 1H), 1.28 (m, 5H), 1.04-1.00 (m, 6H), 0.90 (s, 3H).

Example 29

N-cyclooctyl-5-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}-2-furamide $^1$H NMR (400 MHz, dimethylsulfoxide-$d_6$) δ ppm 12.10 (s, 1H), 9.21 (s, 1H), 8.63-8.72 (m, 2H), 8.29 (d, 1H), 7.90-7.99 (m, 2H), 7.81 (d, 1H), 7.55-7.63 (m, 2H), 7.50 (t, 1H), 7.43 (d, 1H), 7.30 (d, 1H), 7.22 (m, 2H), 7.05 (d, 2H), 4.64 (s, 2H), 3.93-4.17 (m, 3H), 3.81-3.90 (m, 2H), 3.77 (s, 2H), 3.33-3.38 (m, 4H), 3.22-3.30 (m, 4H), 1.92 (s, 1H), 1.43-1.79 (m, 14H), 1.18-1.39 (m, 3H). MS (ESI) m/e 811 (M−H).

Example 30

N-benzyl-7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}bicyclo[2.2.1]hept-2-ene-1-carboxamide $^1$H NMR (400 MHz, dimethylsulfoxide-$d_6$) δ ppm 12.11 (s, 1H), 10.06 (s, 1H), 8.85 (s, 1H), 8.60-8.69 (m, 2H), 7.93 (dd, J=9.1, 2.0 Hz, 1H), 7.79 (d, J=8.9 Hz, 1H), 7.37-7.51 (m, 3H), 7.28 (d, J=9.5 Hz, 1H), 7.18-7.25 (m, 1H), 7.01-7.12 (m, 3H), 6.97 (d, J=9.2 Hz, 2H), 6.85 (d, J=6.8 Hz, 2H), 6.12 (d, J=2.8 Hz, 1H), 4.79 (d, J=10.1 Hz, 1H), 4.14-4.30 (m, 2H), 4.07 (dd, J=14.9, 6.0 Hz, 2H), 3.77-3.87 (m, 2H), 3.30-3.36 (m, 2H), 3.18-3.29 (m, 4H), 3.14 (s, 2H), 2.83-2.98 (m, 2H), 2.74 (d, J=11.7 Hz, 1H), 2.61 (t, J=3.2 Hz, 1H), 2.07-2.19 (m, 1H), 1.82-1.97 (m, 1H), 1.70-1.80 (m, 1H), 1.54-1.69 (m, 2H), 1.18-1.37 (m, 4H), 1.10 (s, 3H), 0.92 (s, 3H). MS (ESI) m/e 845 (M−H)$^-$.

Example 31

4-[4-(2-{[(1R,5S)-8-methyl-8-azabicyclo[3.2.1]oct-3-yl]amino}benzyl)piperazin-1-yl]-N-({3-nitro-4-[(tetrahydro-2H-pyran-4-ylmethyl)amino]phenyl}sulfonyl)benzamide

Example 31A

Ethyl 4-(4-(2-((1R,5S)-8-methyl-8-azabicyclo[3.2.1]octan-3-ylamino)benzyl)piperazin-1-yl)benzoate The title compound was prepared by substituting (1R,5S)-8-methyl-8-azabicyclo[3.2.1]octan-3-one for 2-formylphenylboronic acid and EXAMPLE 16B for EXAMPLE 23C in EXAMPLE 40A.

Example 31B 4-(4-(2-((1R,5S)-8-methyl-8-azabicyclo[3.2.1]octan-3-ylamino)benzyl)piperazin-1-yl)benzoic Acid The title compound was prepared by substituting EXAMPLE 31A for EXAMPLE 2A in EXAMPLE 2B.

Example 31C

4-[4-(2-{[(1R,5S)-8-methyl-8-azabicyclo[3.2.1]oct-3-yl]amino}benzyl)piperazin-1-yl]({3-nitro-4-[(tetrahydro-2H-pyran-4-ylmethyl)amino]phenyl}sulfonyl)benzamide The title compound was prepared by substituting EXAMPLE 31B for EXAMPLE 1A and EXAMPLE 23A for 4-chloro-3-nitrobenzenesulfonamide in EXAMPLE 1B. $^1$H NMR (400 MHz, dimethylsulfoxide-$d_6$) δ 9.42 (s, 1H), 8.64 (m, 2H), 7.93 (dd, 1H), 7.76 (m, 2H), 7.28 (d, 1H), 7.17 (m, 1H), 6.96 (m, 3H), 6.63 (s, 1H), 3.84 (m, 5H), 3.26 (m, 15H), 2.67 (d, 3H), 2.29 (m, 8H), 1.90 (m, 2H), 1.59 (m, 2H), 1.24 (m, 2H).

Example 32

N-({3-nitro-4-[(tetrahydro-2H-pyran-4-ylmethyl) amino]phenyl}sulfonyl)-4-[4-(2-{[(1R,2S,3S,5S)-2, 6,6-trimethylbicyclo[3.1.1]hept-3-yl]amino}benzyl) piperazin-1-yl]benzamide

Example 32A 2-((1R,2S,3S,5S)-2,6,6-trimethylbicyclo[3.1.1]heptan-3-ylamino)benzonitrile 2-Fluorobenzonitrile (100 mg), (1R,2S,3S,5S)-2,6,6-trimethylbicyclo[3.1.1]heptan-3-amine (380 mg), triethylamine (1.5 mL) were dissolved in anhydrous dimethylsulfoxide (5 mL) and heated at 130° C. overnight. The reaction mixture was cooled to room temperature, and diluted with ethyl acetate. The organic phase was washed with water and brine, dried over $Na_2SO_4$, filtered, and concentrated. The residue was purified by flash column purification with 0-5% methanol/dichloromethane to afford the title compound.

Example 32B 2-((1R,2S,3S,5S)-2,6,6-trimethylbicyclo[3.1.1]heptan-3-ylamino)benzaldehyde EXAMPLE 32A (80 mg) was dissolved in anhydrous dichloromethane (5 mL). The solution was cooled at 0° C., and diisobutylaluminum hydride 1M in dichloromethane solution (0.7 mL) was added. The reaction mixture was stirred at room temperature for 3 hours. The reaction was quenched with methanol and 5% L-tartaric acid aqueous solution. The solution was extracted with ethyl acetate, dried over $Na_2SO_4$, filtered, and concentrated. The residue was purified by flash column purification with 0-30% ethyl acetate in hexane to afford the title compound.

Example 32C

Ethyl 4-(4-(2-((1R,2S,3S,5S)-2,6,6-trimethylbicyclo[3.1.1]heptan-3-ylamino)benzyl)piperazin-1-yl)benzoate The title compound was prepared by substituting EXAMPLE 32B for 2-formylphenylboronic acid and ethyl 4-(piperazin-1-yl)benzoate for EXAMPLE 23C in EXAMPLE 40A.

Example 32D 4-(4-(2-((1R,2S,3S,5S)-2,6,6-trimethylbicyclo[3.1.1] heptan-3-ylamino)benzyl)piperazin-1-yl)benzoic Acid The title compound was prepared by substituting EXAMPLE 32C for EXAMPLE 2A in EXAMPLE 2B.

Example 32E

N-({3-nitro-4-[(tetrahydro-2H-pyran-4-ylmethyl) amino]phenyl}sulfonyl)-4-[4-(2-{[(1R,2S,3S,5S)-2, 6,6-trimethylbicyclo[3.1.1]hept-3-yl]amino}benzyl) piperazin-1-yl]benzamide The title compound was prepared by substituting EXAMPLE 32D for EXAMPLE 1A and EXAMPLE 23A for 4-chloro-3-nitrobenzenesulfonamide in EXAMPLE 1B. $^1$H NMR (400 MHz, dimethylsulfoxide-$d_6$) δ 12.10 (s, 1H), 8.65 (m, 2H), 7.93 (dd, 1H), 7.78 (d, 2H), 7.26 (m, 3H), 7.00 (d, 2H), 6.73 (d, 1H), 6.64 (t, 1H), 4.26 (m, 1H), 3.83 (dd, 2H), 3.65 (m, 2H), 3.25 (m, 14H), 2.63 (m, 1H), 2.32 (d, 1H), 2.13 (m, 1H), 1.88 (m, 3H), 1.60 (m, 2H), 1.48 (m, 1H), 1.26 (m, 5H), 1.07 (m, 6H).

Example 33

4-(4-{2-[3-azabicyclo[3.2.2]non-3-yl] benzyl}piperazin-1-yl)-N-({3-nitro-4-[(tetrahydro-2H-pyran-4-ylmethyl)amino]phenyl}sulfonyl)benzamide

Example 33A 2-(3-azabicyclo[3.2.2]nonan-3-yl)benzaldehyde

The title compound was prepared by substituting 2-fluorobenzaldehyde for 2-fluorobenzonitrile and (1s,5s)-3-azabicyclo[3.2.2]nonane for (1R,2S,3S,5S)-2,6,6-trimethylbicyclo[3.1.1]heptan-3-amine in EXAMPLE 32A.

Example 33B

Ethyl 4-(4-(2-(3-azabicyclo[3.2.2]nonan-3-yl)benzyl)piperazin-1-yl)benzoate

The title compound was prepared by substituting EXAMPLE 33A for 2-formylphenylboronic acid and ethyl 4-(piperazin-1-yl)benzoate for EXAMPLE 23C in EXAMPLE 40A.

Example 33C 4-(4-(2-(3-azabicyclo[3.2.2]nonan-3-yl)benzyl)piperazin-1-yl)benzoic Acid The title compound was prepared by substituting EXAMPLE 33B for EXAMPLE 2A in EXAMPLE 2B.

Example 33D 4-(4-{2-[3-azabicyclo[3.2.2]non-3-yl] benzyl}piperazin-1-yl)-N-({3-nitro-4-[(tetrahydro-2H-pyran-4-ylmethyl)amino]phenyl}sulfonyl)benzamide The title compound was prepared by substituting EXAMPLE 33C for EXAMPLE 1A and EXAMPLE 23A for 4-chloro-3-nitrobenzenesulfonamide in EXAMPLE 1B. $^1$H NMR (400 MHz, dimethylsulfoxide-$d_6$) δ 12.07 (m, 1H), 8.65 (m, 2H), 7.93 (dd, 1H), 7.79 (d, 2H), 7.56 (d, 1H), 7.44 (d, 2H), 7.26 (m, 2H), 7.00 (d, 2H), 4.48 (s, 2H), 4.01 (s, 2H), 3.83 (dd, 2H), 3.28 (m, 10H), 2.98 (d, 4H), 1.90 (m, 7H), 1.62 (m, 6H), 1.25 (m, 2H).

Example 34

N-({3-nitro-4-[(tetrahydro-2H-pyran-4-ylmethyl) amino]phenyl}sulfonyl)-4-(4-{2-[tricyclo[4.3.1.1$^{3,8}$] undec-4-en-4-yl]benzyl}piperazin-1-yl)benzamide

Example 34A tricyclo[4.3.1.1$^{3,8}$]undec-4-en-4-yltrifluoromethanesulfonate The title compound was prepared by substituting tricyclo [4.3.1.1$^{3,8}$]undecan-4-one for tricyclo[5.2.1.0$^{2,6}$]decan-8-one in EXAMPLE 23D.

Example 34B

2-Tricyclo[4.3.1.1$^{3,8}$]undec-4-en-4-yl-benzaldehyde

The title compound was prepared by substituting EXAMPLE 34A for EXAMPLE 23D in EXAMPLE 23E.

Example 34C

N-({3-nitro-4-[(tetrahydro-2H-pyran-4-ylmethyl) amino]phenyl}sulfonyl)-4-(4-{2-[tricyclo[4.3.1.1$^{3,8}$] undec-4-en-4-yl]benzyl}piperazin-1-yl)benzamide The title compound was prepared by substituting EXAMPLE 34B for EXAMPLE 23E in EXAMPLE 23F. $^1$H NMR (300 MHz, dimethylsulfoxide-d$_6$) δ 11.97 (br s, 1H), 8.65 (t, 1H), 8.62 (d, 1H), 7.93 (dd, 1H), 7.74 (d, 2H), 7.41 (m, 1H), 7.28-7.21 (m, 3H), 7.08 (m, 1H), 6.92 (d, 2H), 5.52 (m, 1H), 3.84 (dd, 2H), 3.54 (m, 2H), 3.37-3.24 (m, 8H), 2.57-2.44 (m, 2H), 2.29-2.09 (m, 4H), 1.94-1.84 (m, 2H), 1.91 (s, 3H), 1.62 (d, 2H), 1.36-1.18 (m, 4H), 0.88 (s, 9H).

Example 35

7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}-N-phenylbicyclo[2.2.1]hept-2-ene-1-carboxamide $^1$H NMR (500 MHz, dimethylsulfoxide-d$_6$) δ ppm 12.14 (s, 1H), 9.63 (s, 1H), 9.35 (s, 1H), 8.68 (t, 1H), 8.65 (d, 1H), 7.94 (dd, 1H), 7.80 (d, 2H), 7.53-7.60 (m, 1H), 7.33-7.41 (m, 2H), 7.30 (d, 1H), 7.20-7.27 (m, 3H), 7.07 (t, 1H), 7.01 (d, 2H), 6.18 (d, 1H), 4.77 (s, 1H), 4.38 (d, 1H), 4.07 (s, 2H), 3.85 (dd, 3H), 3.32-3.37 (m, 4H), 3.22-3.30 (m, 4H), 3.07-3.20 (m, 2H), 2.71-2.84 (m, 1H), 2.65 (t, 1H), 2.12-2.25 (m, 1H), 1.85-1.96 (m, 1H), 1.74-1.82 (m, 1H), 1.56-1.66 (m, 2H), 1.20-1.34 (m, 4H), 1.17 (s, 3H), 1.00-1.05 (m, 3H). MS (ESI) m/e 831 (M−H)$^-$.

Example 36

7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}-N-[(1S,2S,3S,5R)-2,6,6-trimethylbicyclo[3.1.1]hept-3-yl]bicyclo[2.2.1]hept-2-ene-1-carboxamide $^1$H NMR (500 MHz, dimethylsulfoxide-d$_6$) δ ppm 12.11 (s, 1H), 10.24 (s, 1H), 8.57-8.73 (m, 2H), 8.00 (d, 1H), 7.94 (dd, J=9.2, 2.1 Hz, 1H), 7.80 (d, 2H), 7.50 (dd, 1H), 7.33-7.43 (m, 2H), 7.30 (d, 1H), 7.20 (dd, 1H), 7.01 (d, 2H), 6.14 (d, 1H), 4.87 (d, 1H), 4.21-4.29 (m, 1H), 4.06-4.20 (m, 4H), 3.84 (dd, 4H), 3.51-3.59 (m, 2H), 3.35 (t, 2H), 3.21-3.31 (m, 4H), 3.01-3.20 (m, 2H), 2.94 (d, 1H), 2.63 (t, 1H), 2.53-2.61 (m, 1H), 2.20-2.29 (m, 1H), 2.08-2.19 (m, 2H), 1.80 (t, 2H), 1.58-1.73 (m, 4H), 1.51-1.59 (m, 1H), 1.20-1.33 (m, 6H), 1.17 (s, 3H), 1.10-1.15 (m, 4H), 0.94 (s, 3H), 0.86 (s, 3H), 0.47 (d, 3H). MS (ESI) m/e 891 (M−H)$^-$.

Example 37

N-(adamantan-1-ylmethyl)-7,7-dimethyl-2-{2-[(4-{4-[({3-nitro-4-[(tetrahydro-2H-pyran-4-ylmethyl) amino]phenyl}sulfonyl)carbamoyl] phenyl}piperazin-1-yl)methyl]phenyl}bicyclo[2.2.1] hept-2-ene-1-carboxamide $^1$H NMR (500 MHz, dimethylsulfoxide-d$_6$) δ ppm 12.14 (s, 1H), 10.53 (s, 1H), 8.68 (t, 1H), 8.64 (d, 1H), 8.17 (s, 1H), 7.94 (dd, 1H), 7.82 (t, 1H), 7.47 (d, 1H), 7.40 (t, 1H), 7.36 (t, 1H), 7.30 (d, 1H), 7.23 (d, 1H), 6.13 (d, 1H), 4.88 (d, 1H), 4.11-4.22 (m, 3H), 3.84 (dd, 2H), 3.56 (d, 1H), 3.22-3.29 (m, 4H), 3.14-3.22 (m, 2H), 2.88-3.03 (m, 2H), 2.80 (dd, 1H), 2.62-2.68 (m, 1H), 2.53-2.63 (m, 1H), 2.08-2.18 (m, 1H), 1.84-1.96 (m, 1H), 1.68 (s, 4H), 1.62 (d, 2H), 1.48 (d, 3H), 1.34 (d, 3H), 1.20-1.30 (m, 4H), 1.10-1.19 (m, 6H), 1.00-1.07 (m, 3H), 0.97 (s, 3H). MS (ESI) m/e 903 (M−H)$^-$.

Example 38

N-cyclopropyl-7,7-dimethyl-2-{2-[(4-{4-[({3-nitro-4-[(tetrahydro-2H-pyran-4-ylmethyl)amino] phenyl}sulfonyl)carbamoyl]phenyl}piperazin-1-yl) methyl]phenyl}bicyclo[2.2.1]hept-2-ene-1-carboxamide $^1$H NMR (500 MHz, dimethylsulfoxide-d$_6$) δ ppm 12.15 (s, 1H), 10.14 (s, 1H), 8.68 (t, 1H), 8.64 (d, 1H), 8.04 (s, 1H), 7.94 (dd, 1H), 7.80 (d, 2H), 7.53 (dd, 1H), 7.35-7.43 (m, 2H), 7.30 (d, 1H), 7.12-7.17 (m, 1H), 6.99-7.05 (m, 2H), 6.10 (d, 1H), 4.82 (d, 1H), 4.27 (d, 1H), 4.13 (t, 2H), 3.85 (dd, 2H), 3.35 (t, 2H), 3.16-3.30 (m, 6H), 3.09 (s, 2H), 2.60 (t, 1H), 2.52-2.58 (m, 1H), 2.43-2.49 (m, 1H), 2.03-2.14 (m, 1H), 1.85-1.97 (m, 1H), 1.62 (d, 3H), 1.17-1.32 (m, 3H), 1.14 (s, 3H), 0.91 (s, 3H), 0.45-0.58 (m, 2H), 0.37-0.45 (m, 1H), 0.11-0.19 (m, 1H). MS (ESI) m/e 795 cm−H)$^-$.

Example 39

7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl] phenyl}bicyclo[2.2.1]hept-2-ene-1-carboxylic Acid $^1$H NMR (500 MHz, dimethylsulfoxide-d$_6$) δ ppm 11.96 (s, 1H), 8.57-8.66 (m, 2H), 7.92 (dd, 1H), 7.73 (d, 2H), 7.46-7.51 (m, 1H), 7.40-7.46 (m, 1H), 7.26 (d, 1H), 7.11-7.22 (m, 4H), 7.06 (d, 2H), 7.00 (dd, 1H), 6.91 (d, 2H), 6.26 (d, 1H), 6.16 (d, 1H), 5.10 (s, 1H), 4.59 (s, 1H), 3.83 (dd, 2H), 3.65-3.73 (m, 1H), 3.38-3.52 (m, 3H), 3.23 (s, 2H), 2.50-2.56 (m, 4H), 2.26-2.42 (m, 2H), 1.98-2.07 (m, 2H), 1.90 (s, 3H), 1.46-1.66 (m, 4H), 1.19-1.31 (m, 4H), 1.14 (s, 3H), 1.11 (s, 3H), 1.01-1.10 (m, 2H), 0.93 (s, 6H). MS (ESI) m/e 757

Example 40

4-[4-(2-{5-[8-azabicyclo[3.2.1]oct-8-ylmethyl]-2-thienyl}benzyl)piperazin-1-yl]-N-({3-nitro-4-[(tetrahydro-2H-pyran-4-ylmethyl)amino]phenyl}sulfonyl)benzamide

Example 40A 2-((4-(4-(3-nitro-4-((tetrahydro-2H-pyran-4-yl)methylamino)phenylsulfonylcarbamoyl)phenyl)piperazin-1-yl)methyl)phenylboronic acid EXAMPLE 23C (151 mg) and 2-formylphenylboronic acid (54 mg) were combined in a mixture of tetrahydrofuran (3.5 mL) and acetic acid (1.1 mL). Sodium cyanoborohydride resin (252 mg of 2.38 mmol/g resin) was added and the reaction was stirred at room temperature overnight. The reaction mixture was quenched with aqueous NaHCO₃ solution and extracted with dichloromethane. The organic layer was washed thoroughly with water and with brine, dried over MgSO₄, filtered, and concentrated under vacuum. The crude material was then triturated with ether to afford the title compound.

Example 40B

4-[4-(2-{5-[8-azabicyclo[3.2.1]oct-8-ylmethyl]-2-thienyl}benzyl)piperazin-1-yl]-N-({3-nitro-4-[(tetrahydro-2H-pyran-4-ylmethyl)amino]phenyl}sulfonyl)benzamide nitro-4-((tetrahydro-2H-pyran-4-yl)methylamino)phenylsulfonyl)-2-phenoxybenzamide EXAMPLE 40A (45 mg), 8-((5-bromothiophen-2-yl)methyl)-8-azabicyclo[3.2.1]octane hydrochloride (27 mg), bis(triphenylphosphine)palladium(II) dichloride (5 mg), and lithium hydroxide (7 mg) were combined in a mixture of dimethoxyethane (1.6 mL), methanol (0.5 mL) and water (0.7 mL) in a microwave vial. The reaction mixture was heated in a CEM Discover microwave reactor at 150° C. for 15 minutes. The crude material was purified by preparative HPLC using a C18 column, 250×21.20 mm, 5µ, and eluting with a gradient of 20-100% CH₃CN vs. 0.1% trifluoroacetic acid in water. $^1$H NMR (300 MHz, dimethylsulfoxide-d₆) δ 11.79 (br s, 1H), 8.51 (d, 1H), 8.41 (t, 1H), 7.90 (dd, 1H), 7.73 (m, 4H), 7.60 (d, 2H), 7.41 (m, 2H), 7.35 (m, 1H), 6.81 (m, 2H), 3.83 (dd, 2H), 3.65 (s, 2H), 3.51 (s, 2H), 3.17 (m, 4H), 3.08 (m, 4H), 2.45 (m, 6H), 1.92 (m, 2H), 1.62 (m, 4H), 1.54 (m, 3H), 1.38 (m, 6H).

Example 41

4-{4-[adamantan-1-ylcarbonyl]piperazin-1-yl}-N-{[3-nitro-4-(tetrahydro-2H-pyran-4-ylamino)phenyl]sulfonyl}benzamide

Example 41A 3-nitro-4-(tetrahydro-2H-pyran-4-ylamino)benzenesulfonamide

The title compound was prepared by substituting tetrahydro-2H-pyran-4-amine for cyclohexylmethylamine in EXAMPLE 2D.

Example 41B

4-{-4-[adamantan-1-ylcarbonyl]piperazin-1-yl}benzoic Acid

The title compound was prepared by substituting EXAMPLE 10B for EXAMPLE 8D in EXAMPLE 8E.

Example 41C

4-{4-[adamantan-1-ylcarbonyl]piperazin-1-yl}-N-{[3-nitro-4-(tetrahydro-2H-pyran-4-ylamino)phenyl]sulfonyl}benzamide The title compound was prepared by substituting EXAMPLE 41A for EXAMPLE 2D and EXAMPLE 41B for EXAMPLE 8E in EXAMPLE 8F. $^1$H NMR (300 MHz, dimethylsulfoxide-d₆) δ 12.05 (br s, 1H), 8.64 (d, 1H), 8.30 (d, 1H), 7.95 (dd, 1H), 7.56 (d, 2H), 7.38 (d, 1H), 6.95 (d, 2H), 3.94 (m, 1H), 3.76 (m, 2H), 3.70 (m, 4H), 3.45 (m, 2H), 3.29 (m, 4H), 1.90 (m, 11H), 1.65 (m, 8H).

Example 42

4-{4-[adamantan-2-ylcarbonyl]piperazin-1-yl}-N-{[3-nitro-4-(tetrahydro-2H-pyran-4-ylamino)phenyl]sulfonyl}benzamide

Example 42A

Ethyl 4-{-4-[adamantan-2-ylcarbonyl]piperazin-1-yl}benzoate

The title compound was prepared by substituting EXAMPLE 10A for EXAMPLE 8B and adamantane-2-carboxylic acid for adamantane-1-carboxylic acid in EXAMPLE 8F.

Example 42B

4-{-4-[adamantan-2-ylcarbonyl]piperazin-1-yl}benzoic Acid

The title compound was prepared by substituting EXAMPLE 42A for EXAMPLE 8D in EXAMPLE 8E.

Example 42C

4-{4-[adamantan-2-ylcarbonyl]piperazin-1-yl}-N-{[3-nitro-4-(tetrahydro-2H-pyran-4-ylamino)phenyl]sulfonyl}benzamide The title compound was prepared by substituting EXAMPLE 41A for EXAMPLE 2D and EXAMPLE 42B for EXAMPLE 8E in EXAMPLE 8F. $^1$H NMR (300 MHz, dimethylsulfoxide-d₆) δ 12.05 (br s, 1H), 8.64 (d, 1H), 8.30 (d, 1H), 7.95 (dd, 1H), 7.56 (d, 2H), 7.38 (d, 1H), 6.95 (d, 2H), 3.94 (m, 1H), 3.76 (m, 2H), 3.70 (m, 4H), 3.45 (m, 2H), 3.29 (m, 4H), 2.86 (s, 1H), 2.22 (s, 1H), 2.18 (s, 1H), 1.90 (m, 5H), 1.78 (m, 5H), 1.65 (m, 4H), 1.50 (m, 2H).

Example 43

4-{5-[adamantan-1-ylcarbonyl]-2,5-diazabicyclo[2.2.1]hept-2-yl}-N-{[3-nitro-4-(tetrahydro-2H-pyran-4-ylamino)phenyl]sulfonyl}benzamide

Example 43A

4-{5-[adamantan-1-ylcarbonyl]-2,5-diazabicyclo[2.2.1]hept-2-yl}benzoic Acid

The title compound was prepared by substituting EXAMPLE 11C for EXAMPLE 8D in EXAMPLE 8E.

Example 43B

4-{5-[adamantan-1-ylcarbonyl]-2,5-diazabicyclo[2.2.1]hept-2-yl}-N-{[3-nitro-4-(tetrahydro-2H-pyran-4-ylamino)phenyl]sulfonyl}benzamide The title compound was prepared by substituting EXAMPLE 41A for EXAMPLE 2D and EXAMPLE 43A for EXAMPLE 8E in EXAMPLE 8F. $^1$H NMR (300 MHz, dimethylsulfoxide-$d_6$) δ 11.94 (br s, 1H), 8.64 (d, 1H), 8.30 (d, 1H), 7.95 (dd, 1H), 7.76 (d, 2H), 7.38 (d, 1H), 6.62 (d, 2H), 5.03 (v br s, 1H), 4.63 (s, 1H), 3.87 (m, 3H), 3.61 (br s, 1H), 3.48 (m, 2H), 3.30 (m, 2H), 3.04 (d, 1H), 1.90 (m, 8H), 1.80 (m, 5H), 1.60 (m, 8H).

Example 44

4-{1S,5S)-3-[adamantan-1-ylcarbonyl]-3,6-diazabicyclo[3.2.0]hept-6-yl}-N-{[3-nitro-4-(tetrahydro-2H-pyran-4-ylamino)phenyl]sulfonyl}benzamide

Example 44A (1S,5S)-benzyl 6-(4-(ethoxycarbonyl)phenyl)-3,6-diazabicyclo[3.2.0]heptane-3-carboxylate The title compound was prepared by substituting (1S,5S)-benzyl 3,6-diazabicyclo[3.2.0]heptane-3-carboxylate 4-methylbenzenesulfonate for benzyl 2,6-diazabicyclo[3.2.1]octane-6-carboxylate in EXAMPLE 8A.

Example 44B

Ethyl 4-((1R,5S)-3,6-diazabicyclo[3.2.0]heptan-6-yl)benzoate

The title compound was prepared by substituting EXAMPLE 44A for EXAMPLE 8A in EXAMPLE 8B.

Example 44C

Ethyl 4-[(1S,5S)-3-(adamantan-1-ylcarbonyl)-3,6-diazabicyclo[3.2.0]hept-6-yl]benzoate The title compound was prepared by substituting EXAMPLE 44B for EXAMPLE 8B in EXAMPLE 8C.

Example 44D

4-[(1S,5S)-3-(adamantan-1-ylcarbonyl)-3,6-diazabicyclo[3.2.0]hept-6-yl]benzoic acid The title compound was prepared by substituting EXAMPLE 44C for EXAMPLE 8D in EXAMPLE 8E.

Example 44E

4-{(1S,5S)-3-[(1s,3R,5S)-adamantan-1-ylcarbonyl]-3,6-diazabicyclo[3.2.0]hept-6-yl}-N-{[3-nitro-4-(tetrahydro-2H-pyran-4-ylamino)phenyl]sulfonyl}benzamide The title compound was prepared by substituting EXAMPLE 41A for EXAMPLE 2D and EXAMPLE 44D for EXAMPLE 8E in EXAMPLE 8F. $^1$H NMR (300 MHz, dimethylsulfoxide-$d_6$) δ 11.94 (br s, 1H), 8.64 (d, 1H), 8.30 (d, 1H), 7.95 (dd, 1H), 7.56 (d, 2H), 7.38 (d, 1H), 4.71 (t, 1H), 4.29 (d, 1H), 4.20 (d, 1H), 3.97 (m, 2H) 3.86 (m, 2H), 3.48 (m, 3H), 3.21 (m, 2H), 3.11 (m, 1H), 1.85 (m, 6H), 1.76 (m, 6H), 1.60 (m, 7H).

Example 45

N-{[3-nitro-4-(tetrahydro-2H-pyran-4-ylamino)phenyl]sulfonyl}-4-(4-{(3-phenylpropyl)[(1S,2S,3S,5R)-2,6,6-trimethylbicyclo[3.1.1]hept-3-yl]amino}piperidin-1-yl)benzamide

Example 45A

Ethyl 4-(1,4-dioxa-8-azaspiro[4.5]decan-8-yl)benzoate

Ethyl 4-fluorobenzoate (11.65 g, 69.3 mmol), 1,4-dioxa-8-azaspiro[4.5]decane (9.92 g, 69.3 mmol), and triethylamine (9.66 mL, 69.3 mmol) in N,N-dimethylacetamide (80 mL) were stirred at 80° C. for 24 hours. The reaction was cooled, poured into ethyl acetate, washed with 3× water and brine, and concentrated to afford the title compound.

Example 45B

Ethyl 4-(4-oxopiperidin-1-yl)benzoate

EXAMPLE 45A (20 g, 68 mmol) was stirred at 90° C. for 24 hours in a mixture of dioxane (200 mL), acetic acid (70 mL) and water (150 mL). The reaction mixture was concentrated, and partitioned between ethyl acetate and water. The organic layer was washed with brine and concentrated. The residue was chromatographed on silica gel using 20% ethyl acetate in hexanes to afford the title compound.

Example 45C

Ethyl 4-(4-((1S,2S,3S,5R)-2,6,6-trimethylbicyclo[3.1.1]heptan-3-ylamino)cyclohexyl)benzoate EXAMPLE 45B (2.72 g, 11 mmol) and (1S,2S,3S,5R)-2,6,6-trimethylbicyclo[3.1.1]heptan-3-amine (1.69 g, 11 mmol) were refluxed for 24 hours in toluene (50 mL) under a Dean-Stark trap. The resulting mixture was cooled and ethanol (50 mL) was added, followed by the portionwise addition of NaBH$_4$ (2.0 g). The mixture was stirred for 30 minutes, and water was added. The solution was extracted three times with ether, and the combined extracts were washed with water and brine, and concentrated. The residue was chromatographed on silica gel using ethyl acetate to afford the title compound.

Example 45D

Ethyl 4-(4-((3-phenylpropyl)((1S,2S,3S,5R)-2,6,6-trimethylbicyclo[3.1.1]heptan-3-yl)amino)cyclohexyl)benzoate The title compound was prepared as described in EXAMPLE 7A using EXAMPLE 45C in place of EXAMPLE 6C.

Example 45E 4-(4-((3-phenylpropyl)((1S,2S,3S,5R)-2,6,6-trimethylbicyclo[3.1.1]heptan-3-yl)amino)cyclohexyl)benzoic Acid The title compound was prepared as described in EXAMPLE 2B using EXAMPLE 45D in place of EXAMPLE 2A.

Example 45F

N-{[3-nitro-4-(tetrahydro-2H-pyran-4-ylamino)phenyl]sulfonyl}-4-(4-{(3-phenylpropyl)[(1S,2S,3S,5R)-2,6,6-trimethylbicyclo[3.1.1]hept-3-yl]amino}piperidin-1-yl)benzamide The title compound was prepared as described in EXAMPLE 1B using EXAMPLE 45E in place of EXAMPLE 1A and EXAMPLE 41A in place of 4-chloro-3-nitrobenzenesulfonamide. $^1$H NMR (300 MHz, dimethylsulfoxide-$d_6$) δ 11.90 (s, 1H), 8.54 (s, 1H), 8.14 (d, 1H), 7.89 (d, 1H), 731 (d, 2H), 7.10-7.30 (m, 6H), 6.84 (d, 2H), 3.87 (m, 4H), 3.47 (t, 2H), 3.07 (m, 2H), 2.75 (m, 2H), 2.52 (m, 2H), 2.19 (m, 2H), 1.78-1.99 (m, 6H), 1.53-1.75 (m, 7H), 1.27 (m, 2H), 1.17 (m, 2H), 1.15 (s, 3H), 1.00 (m, 2H), 0.94 (s, 3H), 0.76 (d, 2H).

Example 46

N-({4-[(cyclohexylmethyl)amino]-3-nitrophenyl}sulfonyl)-4-(4-{(3-phenylpropanoyl)[(1S,2S,5R)-2,6,6-trimethylbicyclo[3.1.1]hept-3-yl]amino}piperidin-1-yl)benzamide Example 46A Ethyl 4-(4-(3-phenyl-N-((1S,2S,3S,5R)-2,6,6-trimethylbicyclo[3.1.1]heptan-3-yl)propanamido)cyclohexyl)benzoate To a solution of EXAMPLE 45C (192 mg, 0.5 mmol), triethylamine (0.077 mL, 0.55 mmol) and 4-dimethylaminopyridine (6 mg, 0.05 mmol) in tetrahydrofuran (5 mL) was added 3-phenylpropanoyl chloride (0.082 mL, 0.55 mmol), and the reaction was stirred for 24 hours. The residue was chromatographed on silica gel using 20-50% ethyl acetate in hexanes to afford the title compound.

Example 46B 4-(4-(3-phenyl-N-((1S,2S,3S,5R)-2,6,6-trimethylbicyclo[3.1.1]heptan-3-yl)propanamido)cyclohexyl)benzoic Acid The title compound was prepared as described in EXAMPLE 2B using EXAMPLE 46A in place of EXAMPLE 2A.

Example 46C

N-({4-[(cyclohexylmethyl)amino]-3-nitrophenyl}sulfonyl)-4-(4-{(3-phenylpropanoyl)[(1S,2S,3S,5R)-2,6,6-trimethylbicyclo[3.1.1]hept-3-yl]amino}piperidin-1-yl)benzamide The title compound was prepared as described in EXAMPLE 1B using EXAMPLE 46B in place of EXAMPLE 1B and EXAMPLE 2D in place of 4-chloro-3-nitrobenzenesulfonamide. $^1$H NMR (300 MHz, dimethylsulfoxide-$d_6$) δ 11.90 (s, 1H), 8.61 (m, 2H), 7.92 (d, 1H), 7.72 (d, 2H), 7.20 (m, 5H), 6.90 (m, 2H), 4.07 (m, 4H), 3.93 (m, 2H), 3.18 (m, 4H), 2.65-2.95 (m, 6H), 2.08 (m, 2H), 1.91 (m, 2H), 1.78-1.99 (m, 6H), 1.55-1.76 (m, 11H), 1.22 (s, 3H), 1.17 (m, 2H), 1.01 (s, 3H), 0.99 (d, 2H), 0.90 (d, 2H).

Example 47

4-{4-[adamantan-1-ylmethyl]piperazin-1-yl}-N-({4-[(cyclohexylmethyl)amino]-3-nitrophenyl}sulfonyl)benzamide The title compound was prepared by substituting EXAMPLE 10D for EXAMPLE 8E in EXAMPLE 8F. $^1$H NMR (300 MHz, dimethylsulfoxide-$d_6$) δ 12.05 (br s, 1H), 8.82 (br s, 1H), 8.62 (m, 2H), 7.96 (dd, 1H), 7.78 (d, 2H), 7.26 (d, 1H), 7.00 (d, 2H), 3.86 (br s, 1H), 3.55 (br s, 2H), 3.30 (m, 8H), 2.96 (br s, 1H), 1.99 (s, 3H), 1.60 (m, 18H), 1.18 (m, 3H), 1.00 (m, 2H).

Example 48

6-{3-[adamantan-1-yl]-4-hydroxyphenyl}-N-({4-[(cyclohexylmethyl)amino]-3-nitrophenyl}sulfonyl)-2-naphthamide The title compound was prepared by substituting 6-[3-(1-adamantyl)-4-hydroxyphenyl]-2-naphthalenecarboxylic acid for EXAMPLE 1A and EXAMPLE 2D for 4-chloro-3-nitrobenzenesulfonamide in EXAMPLE 1B. $^1$H NMR (300 MHz, dimethylsulfoxide-$d_6$) δ 12.57 (br s, 1H), 9.52 (s, 1H), 8.68 (d, 1H), 8.61 (m, 1H), 8.54 (s, 1H), 8.27-8.21 (m, 1H), 8.14 (s, 1H), 8.07 (d, 1H), 8.02-7.95 (m, 3H), 7.56-7.47 (m, 2H), 7.25 (d, 1H), 6.91 (d, 1H), 2.16 (br s, 6H), 2.07 (br s, 4H), 1.76-1.65 (m, 12H), 1.25-1.13 (m, 4H), 1.01 (t, 2H).

Example 49

4-(4-{2-[adamantan-1-yl]-2-oxoethyl}piperazin-1-yl)-N-({4-[(cyclohexylmethyl)amino]-3-nitrophenyl}sulfonyl)benzamide Example 49A Ethyl 4-(4-{2-[adamantan-1-yl]-2-oxoethyl}piperazin-1-yl)benzoate Ethyl 4-(piperazin-1-yl)benzoate (100 mg), 1-admantyl bromomethyl ketone (110 mg) and sodium carbonate (46 mg)

were suspended in anhydrous acetonitrile (2 mL). The reaction mixture was stirred at room temperature overnight. The reaction was quenched with saturated NaHCO$_3$ aqueous solution, and extracted with ethyl acetate. The organic phase was washed with water, brine, dried over Na$_2$SO$_4$, filtered and concentrated to afford the title compound Example 49B 4-(4-{2-[adamantan-1-yl]-2-oxoethyl}piperazin-1-yl)benzoic Acid The title compound was prepared by substituting EXAMPLE 49A for EXAMPLE 2A in EXAMPLE 2B.

Example 49C 4-(4-{2-[adamantan-1-yl]-2-oxoethyl}piperazin-1-yl)-N-({4-[(cyclohexylmethyl)amino]-3-nitrophenyl}sulfonyl)benzamide The title compound was prepared by substituting EXAMPLE 49B for EXAMPLE 1A and EXAMPLE 2D for 4-chloro-3-nitrobenzenesulfonamide in EXAMPLE 1B. $^1$H NMR (400 MHz, dimethylsulfoxide-d$_6$) δ 12.16 (m, 1H), 8.65 (m, 2H), 7.94 (dd, 1H), 7.81 (d, 2H), 7.26 (d, 1H), 7.02 (d, 2H), 4.58 (s, 2H), 4.01 (s, 2H), 3.29 (m, 10H), 1.71 (m, 18H), 1.17 (m, 3H), 1.00 (m, 2H).

Example 50

4-{[adamantan-2-ylmethyl]amino}-N-{[3-nitro-4-(tetrahydro-2H-pyran-4-ylamino)phenyl]sulfonyl}benzamide Example 50A 4-[(Adamantan-1-ylmethyl)-amino]-benzoic Acid Ethyl Ester Ethyl 4-fluorobenzoate (336 mg), (2-adamantylmethyl)amine hydrochloride (504 mg) and sodium carbonate (636 mg) were combined in dimethylsulfoxide (5 mL). The reaction was heated to 130° C. overnight. The reaction mixture was diluted with ethyl acetate, poured into water, and the organic layer was washed thoroughly with water and with brine. The combined organic layers were dried over MgSO$_4$, filtered and concentrated under vacuum. The crude material was purified by flash chromatography eluting with 9/1 hexanes/ether.

Example 50B

4-[(Adamantan-1-ylmethyl)-amino]-benzoic Acid

EXAMPLE 50A (365 mg) was dissolved in tetrahydrofuran (6 mL), methanol (2 mL) and water (2 mL). The reaction was heated to 60° C. overnight. The solution was then acidified with 1M aqueous HCl solution. The product was collected by filtration and dried under vacuum.

Example 50C

4-{[adamantan-2-ylmethyl]amino}-N-{[3-nitro-4-(tetrahydro-2H-pyran-4-ylamino)phenyl]sulfonyl}benzamide The title compound was prepared by substituting EXAMPLE 50B for EXAMPLE 1A and EXAMPLE 41A for 4-chloro-3-nitrobenzenesulfonamide in EXAMPLE 1B. $^1$H NMR (500 MHz, dimethylsulfoxide-d$_6$) δ 11.80 (s, 1H), 8.64 (d, 1H), 8.29 (d, 1H), 7.94 (dd, 1H), 7.62 (d, 2H), 7.38 (d, 1H), 6.57 (m, 3H), 3.94 (m, 1H), 3.87 (m, 2H), 3.47 (m, 2H), 3.17 (t, 2H), 1.91 (m, 6H), 1.81 (m, 5H), 1.65 (m, 6H), 1.50 (d, 2H).

Example 51

4-{2-[adamantan-1-yl]ethoxy}-N-{[3-nitro-4-(tetrahydro-2H-pyran-4-ylamino)phenyl]sulfonyl}benzamide Example 51A 4-(2-adamantan-1-yl-ethoxy)-benzoic acid ethyl ester Ethyl 4-hydroxybenzoate (83 mg) and 1-adamantaneethanol (90 mg) were combined in tetrahydrofuran (2 mL). Polymer-supported triphenylphospine (250 mg of 3 mmol/g) and di-tert-butyl azodicarboxylate (173 mg) were added. The reaction was stirred at room temperature overnight. The resin was removed by filtration through celite. The filtrate was concentrated under vacuum, and the residue was triturated with 95/5 hexanes/ether to afford the title compound.

Example 51B 4-(2-adamantan-1-yl-ethoxy)-benzoic Acid

The title compound was prepared by substituting EXAMPLE 51A for EXAMPLE 50A in EXAMPLE 50B.

Example 51C

4-{2-[adamantan-1-yl]ethoxy}-N-{[3-nitro-4-(tetrahydro-2H-pyran-4-ylamino)phenyl]sulfonyl}benzamide The title compound was prepared by substituting EXAMPLE 51B for EXAMPLE 1A and EXAMPLE 41A for 4-chloro-3-nitrobenzenesulfonamide in EXAMPLE 1B. $^1$H NMR (500 MHz, dimethylsulfoxide-d$_6$) δ 12.25 (s, 1H), 8.65 (d, 1H), 8.30 (d, 1H), 7.95 (dd, 1H), 7.83 (d, 2H), 7.40 (d, 1H), 7.00 (d, 2H), 4.09 (t, 2H), 3.95 (m, 1H), 3.87 (m, 2H), 3.47 (m, 2H), 1.92 (m, 5H), 1.64 (m, 8H), 1.54 (d, 6H), 1.52 (t, 2H).

Example 52

N$^3$-[adamantan-1-ylacetyl]-N$^3$-benzyl-N-({4-[(cyclohexylmethyl)amino]-3-nitrophenyl}sulfonyl)-beta-alaninamide Example 52A 3-[(2-adamantan-1-yl-acetyl)-benzyl-amino]-propionic Acid Ethyl Ester The title compound was prepared by substituting 1-adamantaneacetic acid for EXAMPLE 1A and ethyl 3-(benzylamino)propanoate for 4-chloro-3-nitrobenzenesulfonamide in EXAMPLE 1B.

Example 52B

3-[(2-adamantan-1-yl-acetyl)-benzyl-amino]-propionic Acid

The title compound was prepared by substituting EXAMPLE 52A for EXAMPLE 2A in EXAMPLE 2B.

Example 52C $N^3$-[adamantan-1-ylacetyl]-$N^3$-benzyl-N-({4-[(cyclohexylmethyl)amino]-3-nitrophenyl}sulfonyl)-beta-alaninamide The title compound was prepared by substituting EXAMPLE 52B for EXAMPLE 1A, and EXAMPLE 2D for 4-chloro-3-nitrobenzenesulfonamide in EXAMPLE 1B. $^1$H NMR (300 MHz, dimethylsulfoxide-$d_6$) δ 12.12 (br s, 1H), 8.66 (t, 1H), 8.56 (d, 1H), 7.86 (m, 1H), 7.37-7.21 (m, 4H), 7.09 (t, 2H), 4.45 (s, 1H), 4.34 (s, 1H), 3.39 (t, 1H), 2.47 (t, 1H), 1.97 (s, 2H), 1.86 (m, 3H), 1.78-1.52 (m, 18H), 1.24 (s, 1H), 1.22-1.12 (m, 6H), 0.98 (m, 2H).

Example 53

N-({4-[(cyclohexylmethyl)amino]-3-nitrophenyl}sulfonyl)-4-{4-[(1S,2S,3S,5R)-2,6,6-trimethylbicyclo[3.1.1]hept-3-yl]piperazin-1-yl}benzamide

Example 53A

Ethyl 4-(bis(2-hydroxyethyl)amino)benzoate

The title compound was prepared by the methods described in Soloway, A. H., Nyilas, E., J. Org. Chem. 26, 1091 (1961).

Example 53B

Ethyl 4-(bis(2-(methylsulfonyloxy)ethyl)amino)benzoate

EXAMPLE 53A (506 mg) was dissolved in dichloromethane (10 mL) and the mixture was cooled to −14° C. (acetone-ice bath). Triethylamine (0.83 mL) was added, followed by the addition of methanesulfonyl chloride (0.46 mL) dropwise, keeping the temperature below 2° C. The acetone-ice bath was removed and reaction continued at room temperature under nitrogen for 3.5 hours. The reaction was partitioned between saturated aqueous $NaHCO_3$ and ether. The organic layer was washed twice with 1M $H_3PO_4$, and crystals formed in the organic layer. The mixture was filtered and the solid material was washed with ether and dried to give the product.

Example 53C

Ethyl 4-(4-((1S,2S,3S,5R)-2,6,6-trimethylbicyclo[3.1.1]heptan-3-yl)piperazin-1-yl)benzoate EXAMPLE 53B (409 mg) was dissolved in acetonitrile (10 mL), then (1S,2S,3S,5R)-2,6,6-trimethylbicyclo[3.1.1]heptan-3-amine (0.17 mL), potassium carbonate (375 mg), and lithium bromide (183 mg) were added. The reaction was heated under reflux overnight. The reaction was diluted with water and extracted with ethyl acetate. The organic layer was washed with brine and dried over sodium sulfate. The mixture was filtered and the crude material was purified by column chromatography on silica gel using 85/15 hexanes/ethyl acetate.

Example 53D 4-(4-((1S,2S,3S,5R)-2,6,6-trimethylbicyclo[3.1.1]heptan-3-yl)piperazin-1-yl)benzoic Acid The title compound was prepared by substituting EXAMPLE 53C for EXAMPLE 8D in EXAMPLE 8E.

Example 53E

N-({4-[(cyclohexylmethyl)amino]-3-nitrophenyl}sulfonyl)-4-{4-[(1S,2S,3S,5R)-2,6,6-trimethylbicyclo[3.1.1]hept-3-yl]piperazin-1-yl}benzamide The title compound was prepared by substituting EXAMPLE 53D for EXAMPLE 8E in EXAMPLE 8F. $^1$H NMR (300 MHz, dimethylsulfoxide-$d_6$) δ 12.15 (br s, 1H), 9.40 (br s, 1H), 8.62 (m, 2H), 7.96 (dd, 1H), 7.80 (d, 2H), 7.26 (d, 1H), 7.03 (d, 2H), 4.14 (br s, 2H), 3.72 (br m, 2H), 3.28 (t, 2H), 3.17 (br m, 4H), 2.30 (m, 3H), 2.00 (m, 2H), 1.83 (m, 1H), 1.70 (m, 6H), 1.20 (m, 8H), 1.07 (m, 4H), 0.95 (s, 3H).

Example 54

4-{4-[adamantan-1-yl]piperazin-1-yl}-N-({4-[(cyclohexylmethyl)amino]-3-nitrophenyl}sulfonyl)benzamide

Example 54A

Ethyl 4-[4-(adamantan-1-yl)piperazin-1-yl]benzoate

The title compound was prepared by substituting adamantane-1-amine hydrochloride for (1S,2S,3S,5R)-2,6,6-trimethylbicyclo[3.1.1]heptan-3-amine in EXAMPLE 53C.

Example 54B

4-[4-(adamantan-1-yl)piperazin-1-yl]benzoic acid

The title compound was prepared by substituting EXAMPLE 54A for EXAMPLE 8D in EXAMPLE 8E.

Example 54C

4-{-4-[adamantan-1-yl]piperazin-1-yl}-N-({4-[(cyclohexylmethyl)amino]-3-nitrophenyl}sulfonyl)benzamide The title compound was prepared by substituting EXAMPLE 54B for EXAMPLE 8E in EXAMPLE 8F. $^1$H NMR (300 MHz, dimethylsulfoxide-$d_6$) δ 12.10 (br s, 1H), 9.18 (br s, 1H), 8.62 (m, 2H), 7.96 (dd, 1H), 7.80 (d, 2H), 7.24 (d, 1H), 7.03 (d, 2H), 4.09 (br d, 2H), 3.65 (br m, 2H), 3.28 (t, 2H), 3.10 (br m, 4H), 2.20 (s, 3H), 1.95 (s, 6H), 1.70 (m, 12H), 1.18 (m, 3H), 1.00 (m, 2H).

Example 55

N-({4-[(cyclohexylmethyl)amino]-3-nitrophenyl}sulfonyl)-4-{4-[3,5-dimethyladamantan-1-yl]piperazin-1-yl}benzamide

Example 55A

Ethyl 4-[4-(3,5-dimethyladamantan-1-yl)piperazin-1-yl]benzoate

The title compound was prepared by substituting 3,5-dimethyladamantane-1-amine hydrochloride for (1S,2S,3S,5R)-2,6,6-trimethylbicyclo[3.1.1]heptan-3-amine in EXAMPLE 53C.

Example 55B

4-[4-(3,5-dimethyladamantan-1-yl)piperazin-1-yl]benzoic Acid

The title compound was prepared by substituting EXAMPLE 55A for EXAMPLE 8D in EXAMPLE 8E.

Example 55

CN-({4-[(cyclohexylmethyl)amino]-3-nitrophenyl}sulfonyl)-4-{-4-[3,5-dimethyladamantan-1-yl]piperazin-1-yl}benzamide The title compound was prepared by substituting EXAMPLE 55B for EXAMPLE 8E in EXAMPLE 8F. $^1$H NMR (300 MHz, dimethylsulfoxide-$d_6$) δ 12.10 (v br s, 1H), 9.18 (v br s, 1H), 8.62 (m, 2H), 7.96 (dd, 1H), 7.80 (d, 2H), 7.24 (d, 1H), 7.03 (d, 2H), 4.07 (br s, 2H), 3.62 (br s, 2H), 3.28 (t, 2H), 3.10 (br m, 4H), 2.25 (m, 1H), 1.70 (m, 12H), 1.35 (s, 3H), 1.18 (m, 6H), 1.00 (m, 2H), 0.89 (s, 6H).

Example 56

[(3aS,5aR,8aR,8bS)-2,2,7,7-tetramethyltetrahydro-3aH-bis[1,3]dioxolo[4,5-b:4',5'-d]pyran-3a-yl]methyl (4-{4-[(4'-chlorobiphenyl-2-yl)methyl]piperazin-1-yl}benzoyl)sulfamate The title compound was prepared by substituting ((3aS,5aR,8aR,8bS)-2,2,7,7-tetramethyltetrahydro-3 aH-bis[1,3]dioxolo[4,5-b:4',5'-d]pyran-3a-yl)methyl sulfamate for 4-chloro-3-nitrobenzenesulfonamide in EXAMPLE 1B. $^1$H NMR (500 MHz, dimethylsulfoxide-$d_6$) δ 7.81 (d, 2H), 7.75 (m, 1H), 7.55 (m, 4H), 7.41 (d, 2H), 7.35 (m, 1H), 6.96 (d, 2H), 4.54 (dd, 1H), 4.35 (br s, 1H), 4.31 (d, 1H), 4.22 (t, 2H), 4.14 (d, 1H), 3.91 (br s, 2H), 3.72 (m, 2H), 3.60 (m, 3H), 3.11 (br s, 2H), 2.91 (br s, 2H), 1.45 (s, 3H), 1.35 (s, 3H), 1.14 (d, 6H).

Example 57

4-{4-[(4'-chlorobiphenyl-2-yl)methyl]piperazin-1-yl}-N-({[(1R,4S)-7,7-dimethyl-2-oxobicyclo[2.2.1]hept-1-yl]methyl}sulfonyl)benzamide The title compound was prepared as described in EXAMPLE 1B using 41R,4S)-7,7-dimethyl-2-oxobicyclo[2.2.1]heptan-1-yl)methanesulfonamide in place of 4-chloro-3-nitrobenzenesulfonamide. $^1$H NMR (300 MHz, dimethylsulfoxide-$d_6$) δ 11.95 (s, 1H), 7.80 (d, 2H), 7.48 (m, 5H), 7.38 (m, 2H), 7.27 (d, 1H), 6.93 (d, 2H), 3.77 (d, 1H), 3.42 (m, 3H), 3.24 (m, 4H), 2.40 (m, 4H), 2.30 (m, 1H), 2.03 (m, 1H), 1.92 (m, 2H), 1.55 (m, 1H), 1.40 (m, 1H), 1.02 (s, 3H), 0.88 (s, 3H).

Example 58

4-(4-{2-[adamantan-1-yl]ethyl}piperazin-1-yl)-N-({4-[(cyclohexylmethyl)amino]-3-nitrophenyl}sulfonyl)benzamide

Example 58A

Ethyl 4-[4-(adamantan-1-ylacetyl)piperazin-1-yl]benzoate

The title compound was prepared by substituting EXAMPLE 10A for EXAMPLE 8B and 1-adamantylacetic acid for adamantane-1-carboxylic acid in EXAMPLE 8C.

Example 58B

Ethyl 4-{4-[2-(adamantan-1-yl)ethyl]piperazin-1-yl}benzoate

The title compound was prepared by substituting EXAMPLE 58A for EXAMPLE 8C in EXAMPLE 8D.

Example 58C

4-{4-[2-(adamantan-1-yl)ethyl]piperazin-1-yl}benzoic Acid

The title compound was prepared by substituting EXAMPLE 58B for EXAMPLE 8D in EXAMPLE 8E.

Example 58D 4-(4-{2-[adamantan-1-yl]ethyl}piperazin-1-yl)-N-({4-[(cyclohexylmethyl)amino]-3-nitrophenyl}sulfonyl)benzamide The title compound was prepared by substituting EXAMPLE 58C for EXAMPLE 8E in EXAMPLE 8F. $^1$H NMR (300 MHz, dimethylsulfoxide-$d_6$) δ 12.10 (v br s, 1H), 9.44 (v br s, 1H), 8.62 (m, 2H), 7.96 (dd, 1H), 7.80 (d, 2H), 7.26 (d, 1H), 7.02 (d, 2H), 4.07 (br s, 2H), 3.60 (br s, 2H), 3.29 (t, 2H), 3.10 (m, 6H), 1.95 (s, 3H), 1.65 (m, 12H), 1.45 (m, 8H), 1.18 (m, 3H), 1.00 (m, 2H).

Example 59

4-{4-[(4'-chlorobiphenyl-2-yl)methyl]piperazin-1-yl}-N-({[(1S,4R)-7,7-dimethyl-2-oxobicyclo[2.2.1]hept-1-yl]methyl}sulfonyl)benzamide The title compound was prepared as described in EXAMPLE 1B using ((1S,4R)-7,7-dimethyl-2-oxobicyclo[2.2.1]heptan-1-yl)methanesulfonamide in place of 4-chloro-3-nitrobenzenesulfonamide. $^1$H NMR (300 MHz, dimethylsulfoxide-$d_6$) δ 11.95 (s, 1H), 7.80 (d, 2H), 7.48 (m, 5H), 7.38 (m, 2H), 7.27 (d, 1H), 6.91 (d, 2H), 3.75 (d, 1H), 3.40 (m, 3H), 3.25 (m, 4H), 2.40 (m, 4H), 2.30 (m, 1H), 2.03 (m, 1H), 1.91 (m, 2H), 1.50 (m, 1H), 1.38 (m, 1H), 1.02 (s, 3H), 0.80 (s, 3H).

Example 60

N-({4-[(cyclohexylmethyl)amino]-3-nitrophenyl}sulfonyl)-4'-({(3-phenylpropanoyl)[(1S,2S,3S,5R)-2,6,6-trimethylbicyclo[3.1.1]hept-3-yl]amino}methyl)biphenyl-4-carboxamide

Example 60A

Methyl 4'-formylbiphenyl-4-carboxylate

The title compound was prepared as described in EXAMPLE 4A using 4-iodobenzaldehyde in place of 1-bromo-3-iodobenzene.

Example 60B

Methyl 4'-(((1S,2S,3S,5R)-2,6,6-trimethylbicyclo[3.1.1]hept-3-ylamino)methyl)biphenyl-4-carboxylate The title compound was prepared as described in EXAMPLE 7A using (1S,2S,3S,5R)-2,6,6-trimethylbicyclo[3.1.1]heptan-3-amine in place of EXAMPLE 6C and EXAMPLE 60A in place of phenylpropanal.

Example 60C

Methyl 4'-((3-phenyl-N-((1S,2S,3S,5R)-2,6,6-trimethylbicyclo[3.1.1]heptan-3-yl)propanamido)methyl)biphenyl-4-carboxylate The title compound was prepared as described in EXAMPLE 46A using EXAMPLE 60B in place of EXAMPLE 45C.

Example 60D 4'-((3-phenyl-N-((1 S,2 S,3S,5R)-2,6,6-trimethylbicyclo[3.1.1]heptan-3-yl)propanamido)methyl)biphenyl-4-carboxylic Acid The title compound was prepared as described in EXAMPLE 2B using EXAMPLE 60C in place of EXAMPLE 2A.

Example 60E

N-({4-[(cyclohexylmethyl)amino]-3-nitrophenyl}sulfonyl)-4'-({(3-phenylpropanoyl)[(1S,2S,3S,5R)-2,6,6-trimethylbicyclo[3.1.1]hept-3-yl]amino}methyl)biphenyl-4-carboxamide The title compound was prepared as described in EXAMPLE 1B using EXAMPLE 60D in place of EXAMPLE 1A and EXAMPLE 2D in place of 4-chloro-3-nitrobenzenesulfonamide. $^1$H NMR (300 MHz, dimethylsulfoxide-$d_6$) δ 11.90 (s, 1H), 8.63 (d, 1H), 8.59 (m, 1H), 7.94 (m, 3H), 7.73 (d, 2H), 7.68 (d, 1H), 7.62 (d, 1H), 7.05-7.26 (m, 7H), 4.61 (m, 1H), 4.36 (m, 1H), 2.88 (m, 3H), 2.30 (m, 3H), 1.66 (m, 10H), 1.20 (m, 2H), 1.19 (s, 3H), 1.17 (s, 3H), 0.87-1.06 (m, 10H).

Example 61

N-({3-nitro-4-[(tetrahydro-2H-pyran-4-ylmethyl)amino]phenyl}sulfonyl)-4-(4-{2-[(1R,4R)-1,7,7-trimethylbicyclo[2.2.1]hept-2-en-2-yl]benzylidene}piperidin-1-yl)benzamide

Example 61A

Methyl 4-(4-oxopiperidin-1-yl)benzoate

This EXAMPLE was prepared using methods described by Bruncko, et. al., *J. Med. Chem.* 2007, 50, 641-662.

Example 61B

Methyl 4-(4-(2-bromobenzylidene)piperidin-1-yl)benzoate

Dimethylsulfoxide (22.88 mL) with sodium hydride (0.332 g) was heated to 70° C. for 1 hour, the mixture was cooled to room temperature and (2-bromobenzyl)triphenylphosphonium bromide (3.40 g) was added in several portions. The reaction mixture was stirred at room temperature for 1 hour. A solution of EXAMPLE 61A (1.8 g) in dimethylsulfoxide (5.20 mL) was then added and the reaction was heated at 70° C. over the weekend. The reaction mixture was acidified with 1M aqueous HCl solution and extracted with ether. The organic layer was washed thoroughly with water and with brine, dried over MgSO$_4$, filtered and concentrated under vacuum. The crude material was purified by flash chromatography eluting with 100% hexanes to 20% ethyl acetate in hexanes.

Example 61C 4-(4-(2-((1R)-1,7,7-trimethylbicyclo[2.2.1]hept-2-en-2-yl)benzylidene)piperidin-1-yl)benzoic Acid The title compound was prepared by substituting (1S)-1,7,7-trimethylbicyclo[2.2.1]hept-2-en-2-ylboronic acid for EXAMPLE 40A and EXAMPLE 61B for 8-((5-bromothiophen-2-yl)methyl)-8-azabicyclo[3.2.1]octane hydrochloride in EXAMPLE 40B.

Example 61D

N-({3-nitro-4-[(tetrahydro-2H-pyran-4-ylmethyl)amino]phenyl}sulfonyl)-4-(4-{2-[(1R,4R)-1,7,7-trimethylbicyclo[2.2.1]hept-2-en-2-yl]benzylidene}piperidin-1-yl)benzamide The title compound was prepared by substituting EXAMPLE 61C for EXAMPLE 1A and EXAMPLE 23A for 4-chloro-3-nitrobenzenesulfonamide in EXAMPLE 1B. $^1$H NMR (500 MHz, dimethylsulfoxide-$d_6$) δ 11.97 (s, 1H), 8.64 (m, 2H), 7.93 (dd, 1H), 7.74 (d, 2H), 7.30 (d, 1H), 7.21 (m, 2H), 7.14 (m, 1H), 6.95 (d, 2H), 6.36 (s, 1H), 5.87 (d, 1H), 3.84 (m, 2H), 3.48 (m, 2H), 3.40, 3.32, 3.24 (all m, total 6H), 2.40 (t, 1H), 2.34 (m, 4H), 1.90 (m, 2H), 1.61 (m, 3H), 1.27 (m, 3H), 1.06 (m, 1H), 0.94 (s, 3H), 0.83 (s, 3H), 0.79 (s, 3H).

Example 62

N-({3-nitro-4-[(tetrahydro-2H-pyran-4-ylmethyl) amino]phenyl}sulfonyl)-4-(4-{2-[5-(4-phenyl-1,3-thiazol-2-yl)-2-thienyl]benzyl}piperazin-1-yl)benzamide

Example 62A

Ethyl 4-(4-(2-bromobenzyl)piperazin-1-yl)benzoate

This EXAMPLE was prepared using methods described by Bruncko, et. al., *J. Med. Chem.* 2007, 50, 641-662.

Example 62B

Ethyl 4-(4-(2-(4,4,5,5-tetramethyl-1,3,2-dioxaborolan-2-yl)benzyl)piperazin-1-yl)benzoate A solution of tris(dibenzylideneacetone)dipalladium(0) (0.284 g) and tricyclohexylphosphine (0.417 g) in dioxane (75 mL) was stirred at room temperature for 30 minutes. EXAMPLE 62A (5 g), 4,4,4',4',5,5,5',5'-octamethyl-2,2'-bi (1,3,2-dioxaborolane) (3.46 g) and potassium acetate (1.825 g) were added, and the reaction was heated to 85° C. for 36 hours. The reaction mixture was diluted with ethyl acetate and washed thoroughly with water and with brine. The combined organic layers were dried over $MgSO_4$, filtered and concentrated under vacuum. The crude solid was washed with hexanes and with hexanes/ether (2:1) to obtain the title compound.

Example 62C 4-(4-(2-(5-(4-phenylthiazol-2-yl)thiophen-2-yl)benzyl)piperazin-1-yl)benzoic Acid The title compound was prepared by substituting EXAMPLE 62B for EXAMPLE 40A and 2-(5-bromothiophen-2-yl)-4-phenylthiazole for 8-((5-bromothiophen-2-yl)methyl)-8-azabicyclo[3.2.1]octane hydrochloride in EXAMPLE 40B.

Example 62D

N-({3-nitro-4-[(tetrahydro-2H-pyran-4-ylmethyl) amino]phenyl}sulfonyl)-4-(4-{2-[5-(4-phenyl-1,3-thiazol-2-yl)-2-thienyl]benzyl}piperazin-1-yl)benzamide The title compound was prepared by substituting EXAMPLE 62C for EXAMPLE 1A and EXAMPLE 23A for 4-chloro-3-nitrobenzenesulfonamide in EXAMPLE 1B. $^1$H NMR (300 MHz, dimethylsulfoxide-$d_6$) δ 11.79 (s, 1H), 8.64 (s, 1H), 8.59 (s, 1H), 8.06 (br s, 1H), 7.99 (d, 1H), 7.83 (d, 2H), 7.60 (d, 2H), 7.50 (m, 3H), 7.36 (d, 1H), 7.11 (m, 3H), 7.01 (m, 4H), 6.97 (d, 1H), 3.71 (m, 2H), 3.60 (m, 4H), 3.45 (m, 4H), 3.02 (m, 2H), 2.60 (m, 4H), 1.83 (m, 1H), 1.56 (m, 4H).

Example 63

4-[4-(2-{5-[4-(adamantan-1-yl)-1,3-thiazol-2-yl]-2-thienyl}benzyl)piperazin-1-yl]-N-({3-nitro-4-[(tetrahydro-2H-pyran-4-ylmethyl)amino] phenyl}sulfonyl)benzamide $^1$H NMR (400 MHz, dimethylsulfoxide-$d_6$) δ ppm 12.04 (s, 1H), 8.66 (t, 1H), 8.63 (d, 1H), 7.93 (dd, 1H), 7.75 (d, 3H), 7.63 (d, 1H), 7.57 (s, 3H), 7.29 (d, 1H), 7.20-7.26 (m, 2H), 6.95 (d, 2H), 4.56 (s, 1H), 3.78-3.89 (m, 2H), 3.31-3.37 (m, 6H), 3.26 (dd, 4H), 2.97-3.18 (m, 2H), 2.04 (s, 3H), 1.93 (s, 3H), 1.93 (s, 3H), 1.57-1.80 (m, 10H), 1.21-1.40 (m, 5H). MS (ESI) m/e 891 (M–H)$^-$.

Example 64

5-{2-[(4-{4-[({3-nitro-[(tetrahydro-2H-pyran-4-ylmethyl)amino]phenyl}sulfonyl)carbamoyl] phenyl}piperazin-1-yl)methyl]phenyl}-N-(2-phenyl-1,3-benzoxazol-5-yl)-2-furamide $^1$H NMR (400 MHz, dimethylsulfoxide-$d_6$) δ ppm 12.09 (s, 1H), 10.46 (s, 1H), 9.27 (s, 1H), 8.59-8.70 (m, 2H), 8.29 (d, 1H), 8.22 (dd, 2H), 8.02 (d, 1H), 7.94 (dd, 1H), 7.75-7.84 (m, 3H), 7.59-7.73 (m, 7H), 7.50-7.57 (m, 1H), 7.34 (s, 1H), 7.29 (d, 1H), 7.05 (d, 2H), 4.71 (s, 1H), 4.14 (s, 1H), 3.72-3.90 (m, 3H), 3.20-3.32 (m, 4H), 1.83-1.97 (m, 1H), 1.61 (d, 2H), 1.16-1.33 (m, 3H). MS (ESI) m/e 894 (M–H)$^-$.

Example 65

N-({3-nitro-4-[(tetrahydro-2H-pyran-4-ylmethyl) amino]phenyl}sulfonyl)-4-{4-[2-(triphenylvinyl) benzyl]piperazin-1-yl}benzamide

Example 65A 4-(4-(2-(1,2,2-triphenylvinyl)benzyl)piperazin-1-yl) benzoic Acid The title compound was prepared by substituting EXAMPLE 62B for EXAMPLE 40A and bromotriphenylethylene for 8-((5-bromothiophen-2-yl)methyl)-8-azabicyclo[3.2.1]octane hydrochloride in EXAMPLE 40B.

Example 65B

N-({3-nitro-4-[(tetrahydro-2H-pyran-4-ylmethyl) amino]phenyl}sulfonyl)-4-{-4-[2-(triphenylvinyl) benzyl]piperazin-1-yl}benzamide The title compound was prepared by substituting EXAMPLE 65A for EXAMPLE 1A and EXAMPLE 23A for 4-chloro-3-nitrobenzenesulfonamide in EXAMPLE 1B. $^1$H NMR (500 MHz, dimethylsulfoxide-$d_6$) δ 11.97 (s, 1H), 8.63 (s, 1H), 8.07 (br s, 1H), 7.99 (d, 1H), 7.60 (d, 2H), 7.42 (m, 6H), 7.30 (m, 4H), 7.26 (m, 6H), 7.07 (m, 2H), 6.99 (m, 4H), 3.82 (br s, 2H), 3.60 (m, 4H), 3.45 (m, 4H), 3.02 (m, 2H), 2.62 (m, 4H), 1.83 (m, 1H), 1.56 (m, 4H).

Example 66

4-{4-[2-(5-methyl-5,6-dihydrophenanthridin-6-yl) benzyl]piperazin-1-yl}-N-({3-nitro-4-[(tetrahydro-2H-pyran-4-ylmethyl)amino]phenyl}sulfonyl)benzamide The title compound was prepared by substituting 2-(5-methyl-5,6-dihydro-phenanthridin-6-yl)-benzaldehyde for EXAMPLE 23E in EXAMPLE 23F. $^1$H NMR (300 MHz, dimethylsulfoxide-$d_6$) δ 12.03 (br s, 1H), 8.57 (d, 1H), 8.53 (t, 1H), 7.92 (dd, 1H), 7.90 (d, 2H), 7.83 (m, 1H), 7.76 (d, 2H), 7.41 (d, 1H), 7.28-6.99 (m, 6H), 6.92 (d, 2H), 6.77 (td, 1H), 6.59 (dd, 1H), 6.13 (s, 1H), 3.91 (d, 1H), 3.85 (dd, 2H), 3.65

(d, 1H), 3.30-3.23 (m, 2H), 2.78 (s, 3H), 2.70-2.53 (m, 5H), 1.91 (s, 3H), 1.90 (m, 1H), 1.62 (dd, 2H), 1.38-1.20 (m, 6H), 0.86 (m, 2H).

Example 67

N-({3-nitro-4-[(tetrahydro-2H-pyran-4-ylmethyl) amino]phenyl}sulfonyl)-4-{4-[2-(4,4,5,5-tetramethyl-1,3,2-dioxaborolan-2-yl)benzyl]piperazin-1-yl}benzamide The title compound was prepared by substituting (2-formylphenyl)boronic acid pinacol ester for EXAMPLE 23E in EXAMPLE 23F. $^1$H NMR (300 MHz, dimethylsulfoxide-$d_6$) δ 11.94 (br s, 1H), 8.60 (d, 1H), 7.94-7.89 (m, 1H), 7.75 (d, 2H), 7.62 (m, 1H), 7.50-7.21 (m, 4H), 7.25 (d, 1H), 6.92 (d, 2H), 3.84 (dd, 2H), 3.36-3.32 (m, 8H), 2.51 (br s, 2H), 1.91 (s, 3H), 1.62 (dt, 2H), 1.30 (br s, 9H), 1.26 (dd, 2H), 1.16 (s, 6H), 1.07 (s, 2H).

Example 68

4-(4-{2-[2-(2,6-dimethoxybenzoyl)-3-thienyl] benzylidene}piperidin-1-yl)-N-({3-nitro-4-[(tetrahydro-2H-pyran-4-ylmethyl)amino]phenyl}sulfonyl) benzamide

Example 68A

Methyl 4-(4-(2-(4,4,5,5-tetramethyl-1,3,2-dioxaborolan-2-yl)benzylidene)piperidin-1-yl)benzoate EXAMPLE 61B (259 mg), bis(pinacolato)diboron (206 mg), [1,1'-bis(diphenylphosphino)ferrocene]dichloropalladium(II) dichloromethane (22 mg), and potassium acetate (159 mg) were combined in dimethylsulfoxide (2.7 mL). The reaction mixture was heated at 90° C. for 36 hours. The reaction mixture was diluted with ethyl acetate, washed thoroughly with water and with brine, dried over MgSO$_4$, filtered and concentrated under vacuum. The crude solid was washed with hexanes and with hexanes/ether (2:1) to obtain the title compound.

Example 68B

Ethyl 4-(4-(2-(2-(2,6-dimethoxybenzoyl)thiophen-3-yl)benzylidene)piperidin-1-yl)benzoate EXAMPLE 68A (0.043 g), (3-bromothiophen-2-yl)(2,6-dimethoxyphenyl)methanone (0.03114 g), tetrakis(triphenylphosphine)palladium(0) (11.00 mg) and cesium fluoride (0.043 g) were combined in 1,2-dimethoxyethane (0.333 ml) and ethanol (0.143 ml). The reaction was heated to 90° C. for 2 hours. The reaction mixture was diluted with ethyl acetate, poured into water, and washed thoroughly with water and with brine. The combined organic layers were dried over MgSO$_4$, filtered, and concentrated under vacuum. The crude material was purified by flash chromatography, eluting with a gradient of 1% methanol/dichloromethane to 5% methanol/dichloromethane.

Example 68C 4-(4-(2-(2-(2,6-dimethoxybenzoyl)thiophen-3-yl) benzylidene)piperidin-1-yl)benzoic Acid The title compound was prepared by substituting EXAMPLE 68B for EXAMPLE 50A in EXAMPLE 50B.

Example 68D 4-(4-{2-[2-(2,6-dimethoxybenzoyl)-3-thienyl] benzylidene}piperidin-1-yl)-N-({3-nitro-4-[(tetrahydro-2H-pyran-4-ylmethyl)amino]phenyl}sulfonyl) benzamide The title compound was prepared by substituting EXAMPLE 68C for EXAMPLE 1A and EXAMPLE 23A for 4-chloro-3-nitrobenzenesulfonamide in EXAMPLE 1B. $^1$H NMR (400 MHz, dimethylsulfoxide-$d_6$) δ 11.95 (s, 1H), 8.63 (m, 2H), 7.93 (dd, 1H), 7.87 (d, 1H), 7.72 (d, 2H), 7.27 (d, 1H), 7.20 (s, 1H), 7.09 (m, 3H), 6.93 (m, 4H), 6.40 (d, 2H), 5.99 (s, 1H), 3.83 (dd, 2H), 3.60 (s, 6H), 3.26 (m, 6H), 2.31 (m, 2H), 2.22 (m, 2H), 1.90 (br s, 1H), 1.60 (m, 2H), 1.26 (m, 4H).

Example 69

1-[adamantan-1-yl]-4-{2-[(1-{4-[({3-nitro-4-[(tetrahydro-2H-pyran-4-ylmethyl)amino] phenyl}sulfonyl)carbamoyl]phenyl}piperidin-4-ylidene)methyl]phenyl}-N,N-diphenyl-1H-pyrazole-3-carboxamide

Example 69A

4-{4-[2-(1-adamantan-1-yl-3-diphenylcarbamoyl-1H-pyrazol-4-yl)-benzylidene]-piperidin-1-yl}-benzoic Acid ethyl ester The title compound was prepared by substituting 1-adamantan-1-yl-4-bromo-1H-pyrazole-3-carboxylic acid diphenylamide for (3-bromothiophen-2-yl)(2,6-dimethoxyphenyl)methanone in EXAMPLE 68B.

Example 69B

4-{4-[2-(1-adamantan-1-yl-3-diphenylcarbamoyl-1H-pyrazol-4-yl)-benzylidene]-piperidin-1-yl}-benzoic Acid The title compound was prepared by substituting EXAMPLE 69A for EXAMPLE 50A in EXAMPLE 50B.

Example 69C

1-[adamantan-1-yl]-4-{2-[(1-{4-[({3-nitro-4-[(tetrahydro-2H-pyran-4-ylmethyl)amino] phenyl}sulfonyl)carbamoyl]phenyl}piperidin-4-ylidene)methyl]phenyl}-N,N-diphenyl-1H-pyrazole-3-carboxamide The title compound was prepared by substituting EXAMPLE 69B for EXAMPLE 1A and EXAMPLE 23A for 4-chloro-3-nitrobenzenesulfonamide in EXAMPLE 1B. $^1$H NMR (500 MHz, dimethylsulfoxide-$d_6$) δ 11.95 (s, 1H), 8.64 (m, 2H), 7.93 (dd, 1H), 7.43 (d, 2H), 7.52 (s, 1H), 7.26 (m, 4H), 7.19 (m, 4H), 7.13 (m, 3H), 6.91 (m, 6H), 5.58 (s, 1H), 3.83 (dd, 2H), 3.47 (t, 2H), 3.25 (m, 6H), 2.23 (m, 4H), 2.07 (m, 3H), 1.89 (m, 6H), 1.62 (m, 8H), 1.26 (m, 3H).

Example 70

N-({3-nitro-4-[(tetrahydro-2H-pyran-4-ylmethyl)amino]phenyl}sulfonyl)-4-(4-{2-[octahydro-1H-4,7-methanoinden-5-yl(3-phenylpropanoyl)amino]benzyl}piperazin-1-yl)benzamide

Example 70A

Ethyl 4-(4-{2-[octahydro-1H-4,7-methanoinden-5-yl(3-phenylpropanoyl)amino]benzyl}piperazin-1-yl)benzoate EXAMPLE 16C (60 mg), 3-phenylpropanoyl chloride (22 mg) and diisopropylethylamine (0.05 mL) were dissolved in anhydrous dichloromethane (3 mL). The reaction mixture was stirred at room temperature overnight. The reaction was quenched with saturated NaHCO$_3$ aqueous solution, and extracted with ethyl acetate. The organic phase was washed with water, brine, dried over Na$_2$SO$_4$, filtered, and concentrated. The residue was purified by flash column purification with 0-5% methanol in dichloromethane to afford the title compound.

Example 70B 4-(4-{2-[octahydro-1H-4,7-methanoinden-5-yl(3-phenylpropanoyl)amino]benzyl}piperazin-1-yl)benzoic Acid The title compound was prepared by substituting EXAMPLE 70A for EXAMPLE 2A in EXAMPLE 2B.

Example 70C

N-({3-nitro-4-[(tetrahydro-2H-pyran-4-ylmethyl)amino]phenyl}sulfonyl)-4-(4-{2-[octahydro-1H-4,7-methanoinden-5-yl(3-phenylpropanoyl)amino]benzyl}piperazin-1-yl)benzamide The title compound was prepared by substituting EXAMPLE 70B for EXAMPLE 1A and EXAMPLE 23A for 4-chloro-3-nitrobenzenesulfonamide in EXAMPLE 1B. $^1$H NMR (400 MHz, dimethylsulfoxide-d$_6$) δ 12.03 (m, 1H), 8.64 (m, 2H), 7.93 (dd, 1H), 7.76 (d, 2H), 7.58 (s, 1H), 7.39 (m, 2H), 7.28 (d, 1H), 7.18 (m, 3H), 7.00 (m, 5H), 4.32 (m, 1H), 3.83 (m, 2H), 3.26 (m, 8H), 2.81 (m, 6H), 2.19 (m, 2H), 1.90 (m, 4H), 1.67 (m, 7H), 1.22 (m, 11H).

Example 71

4-[4-(2-{5-[8-azabicyclo[3.2.1]oct-8-ylmethyl]-2-thienyl}benzylidene)piperidin-1-yl]-N-({3-nitro-4-[(tetrahydro-2H-pyran-4-ylmethyl)amino]phenyl}sulfonyl)benzamide

Example 71A

Ethyl 4-(4-(2-(5-(8-azabicyclo[3.2.1]octan-8-ylmethyl)thiophen-2-yl)benzylidene)piperidin-1-yl)benzoate The title compound was prepared by substituting 8-((5-bromothiophen-2-yl)methyl)-8-azabicyclo[3.2.1]octane hydrochloride for (3-bromothiophen-2-yl)(2,6-dimethoxyphenyl)methanone in EXAMPLE 68B.

Example 71B 4-(4-(2-(5-(8-azabicyclo[3.2.1]octan-8-ylmethyl)thiophen-2-yl)benzylidene)piperidin-1-yl)benzoic Acid The title compound was prepared by substituting EXAMPLE 71A for EXAMPLE 50A in EXAMPLE 50B.

Example 71C

4-[4-(2-{5-[8-azabicyclo[3.2.1]oct-8-ylmethyl]-2-thienyl}benzylidene)piperidin-1-yl]-N-({3-nitro-4-[(tetrahydro-2H-pyran-4-lmethyl)amino]phenyl}sulfonyl)benzamide The title compound was prepared by substituting EXAMPLE 71B for EXAMPLE 1A and EXAMPLE 23A for 4-chloro-3-nitrobenzenesulfonamide in EXAMPLE 1B. $^1$H NMR (300 MHz, dimethylsulfoxide-d$_6$) δ 11.54 (s, 1H), 9.36 (br s, 1H), 8.48 (d, 1H), 7.76 (dd, 1H), 7.53 (m, 3H), 7.34 (m, 3H), 7.00 (m, 1H), 6.84 (d, 2H), 6.81 (dd, 1H), 6.44 (d, 1H), 6.37 (br s, 1H), 4.36 (d, 2H), 3.82 (m, 3H), 3.36 (m, 2H), 3.26 (m, 4H), 3.18 (m, 2H), 2.36 (m, 3H), 2.23 (m, 4H), 1.90 (m, 3H), 1.81 (m, 2H), 1.62 (m, 5H), 1.40 (m, 3H).

Example 72

N-({3-nitro-4-[(tetrahydro-2H-pyran-4-ylmethyl)amino]phenyl}sulfonyl)-4-[4-(4-{[(1S,2S,3S,5R)-2,6,6-trimethylbicyclo[3.1.1]hept-3-yl]amino}benzylidene)piperidin-1-yl]benzamide

Example 72A

Ethyl 4-(4-(4-bromobenzylidene)piperidin-1-yl)benzoate

The title compound was prepared by substituting (4-bromobenzyl)triphenylphosphonium bromide for (2-bromobenzyl)triphenylphosphonium bromide in EXAMPLE 61B.

Example 72B

Ethyl 4-(4-(4-((1S,2S,3S,5R)-2,6,6-trimethylbicyclo[3.1.1]heptan-3-ylamino)benzylidene)piperidin-1-yl)benzoate EXAMPLE 72A (40 mg), (1S,2S,3S,5R)-2,6,6-trimethylbicyclo[3.1.1]heptan-3-amine (100 μl), 2,2'-bis(diphenylphosphino)-1,1'-binaphthyl (9.2 mg), palladium(II) acetate (2.4 mg), and sodium tert-butoxide (14 mg) were added to toluene (0.2 mL), the reaction was purged with nitrogen and heated at 100° C. overnight. The reaction was cooled, then diluted with water and extracted with ethyl acetate. The organic layer was washed with brine and dried over sodium sulfate. After filtration and concentration, the crude material was purified by column chromatography on silica gel using 94/6 hexanes/ethyl acetate.

Example 72C 4-(4-(4-((1S,2S,3S,5R)-2,6,6-trimethylbicyclo[3.1.1]heptan-3-ylamino)benzylidene)piperidin-1-yl)benzoic Acid The title compound was prepared by substituting EXAMPLE 72B for EXAMPLE 8D in EXAMPLE 8E.

Example 72D

N-({3-nitro-4-[(tetrahydro-2H-pyran-4-ylmethyl)amino]phenyl}sulfonyl)-4-[4-(4-{[(1S,2S,3S,5R)-2,6,6-trimethylbicyclo[3.1.1]hept-3-yl]amino}benzylidene)piperidin-1-yl]benzamide The title compound was prepared by substituting EXAMPLE 72C for EXAMPLE 8E and EXAMPLE 23A for EXAMPLE 2D in EXAMPLE 8F. $^1$H NMR (300 MHz, dimethylsulfoxide-$d_6$) δ 11.97 (br s, 1H), 8.65 (t, 1H), 8.63 (d, 1H), 7.95 (dd, 1H), 7.76 (d, 2H), 7.28 (d, 1H), 7.06 (br s, 2H), 6.95 (d, 2H), 6.90 (v br s, 2H), 6.26 (s, 1H), 3.85 (m, 2H), 3.50 (m, 5H), 3.33 (t, 2H), 3.25 (m, 2H), 2.38 (m, 3H), 2.00 (m, 1H), 1.94 (m, 2H), 1.80 (m, 1H), 1.60 (m, 3H), 1.25 (m, 5H), 1.21 (s, 3H), 1.09 (d, 1H), 1.00 (s, 6H).

Example 73

N-({3-nitro-4-[(tetrahydro-2H-pyran-4-ylmethyl)amino]phenyl}sulfonyl)-4-[4-(3-{[(1S,2S,3S,5R)-2,6,6-trimethylbicyclo[3.1.1]hept-3-yl]amino}benzylidene)piperidin-1-yl]benzamide

Example 73A

Ethyl 4-(4-(3-bromobenzylidene)piperidin-1-yl)benzoate

The title compound was prepared by substituting (3-bromobenzyl)triphenylphosphonium bromide for (2-bromobenzyl)triphenylphosphonium bromide in EXAMPLE 61B.

Example 73B

Ethyl 4-(4-(3-((1S,2S,3S,5R)-2,6,6-trimethylbicyclo[3.1.1]heptan-3-ylamino)benzylidene)piperidin-1-yl)benzoate The title compound was prepared by substituting EXAMPLE 73A for EXAMPLE 72A in EXAMPLE 72B.

Example 73C 4-(4-(3-((1S,2S,3S,5R)-2,6,6-trimethylbicyclo[3.1.1]heptan-3-ylamino)benzylidene)piperidin-1-yl)benzoic Acid The title compound was prepared by substituting EXAMPLE 73B for EXAMPLE 8D in EXAMPLE 8E.

Example 73D

N-({3-nitro-4-[(tetrahydro-2H-pyran-4-ylmethyl)amino]phenyl}sulfonyl)-4-[4-(3-{[(1S,2S,3S,5R)-2,6,6-trimethylbicyclo[3.1.1]hept-3-yl]amino}benzylidene)piperidin-1-yl]benzamide The title compound was prepared by substituting EXAMPLE 73C for EXAMPLE 8E and EXAMPLE 23A for EXAMPLE 2D in EXAMPLE 8F. $^1$H NMR (300 MHz, dimethylsulfoxide-$d_6$) δ 12.00 (br s, 1H), 8.68 (t, 1H), 8.63 (d, 1H), 7.95 (dd, 1H), 7.76 (d, 2H), 7.30 (d, 1H), 7.18 (v br s, 2H), 6.96 (d, 2H), 6.75 (v br s, 2H), 6.26 (s, 1H), 3.85 (m, 2H), 3.50 (m, 5H), 3.37 (t, 2H), 3.25 (m, 2H), 2.40 (m, 2H), 2.37 (m, 1H), 2.00 (m, 1H), 1.94 (m, 2H), 1.80 (m, 1H), 1.60 (m, 3H), 1.25 (m, 5H), 1.20 (s, 3H), 1.12 (d, 1H), 1.00 (s, 6H).

Example 74

4-[4-(2-{5-[4-(adamantan-1-yl)-1,3-thiazol-2-yl]-2-thienyl}benzylidene)piperidin-1-yl]-N-({3-nitro-4-[(tetrahydro-2H-pyran-4-ylmethyl)amino]phenyl}sulfonyl)benzamide $^1$H NMR (400 MHz, dimethylsulfoxide-$d_6$) δ ppm 11.96 (s, 1H), 8.59-8.72 (m, 2H), 7.93 (dd, 1H), 7.72 (d, 2H), 7.64 (dd, 1H), 7.54 (d, 1H), 7.22-7.40 (m, 4H), 7.16 (s, 1H), 6.94 (d, 2H), 6.43 (s, 1H), 3.83 (dd, 2H), 3.53-3.62 (m, 2H), 3.37-3.43 (m, 4H), 3.19-3.29 (m, 2H), 2.40-2.46 (m, 2H), 2.28-2.36 (m, 2H), 1.97 (s, 2H), 1.83-1.93 (m, 5H), 1.55-1.70 (m, 6H), 1.18-1.31 (m, 2H). MS (ESI) m/e 888 (M−H).

Example 75

N-({3-nitro-4-[(tetrahydro-2H-pyran-4-ylmethyl)amino]phenyl}sulfonyl)-4-(4-{2-[5-(4-phenyl-1,3-thiazol-2-yl)-2-thienyl]benzylidene}piperidin-1-yl)benzamide $^1$H NMR (400 MHz, dimethylsulfoxide-$d_6$) δ ppm 11.97 (s, 1H), 8.58-8.71 (m, 2H), 8.08 (s, 1H), 7.89-7.98 (m, 3H), 7.88-7.98 (m, 3H), 7.74 (d, 2H), 7.63-7.71 (m, 2H), 7.24-7.46 (m, 8H), 6.97 (d, 2H), 6.47 (s, 1H), 3.83 (dd, 2H), 3.57-3.67 (m, 2H), 3.38-3.46 (m, 2H), 3.33-3.37 (m, 2H), 3.19-3.29 (m, 4H), 2.40-2.48 (m, 2H), 2.29-2.37 (m, 2H), 1.82-1.98 (m, 1H), 1.61 (d, 2H), 1.16-1.32 (m, 2H). MS (ESI) m/e 830 (M−H)⁻.

Example 76

N-[(4-{[adamantan-1-ylmethyl]amino}-3-nitrophenyl)sulfonyl]-4-(4-oxo-4H-chromen-6-yl)benzamide

Example 76A 4-(4-oxo-4H-chromen-6-yl)benzoic Acid

The title compound was prepared as described in EXAMPLE 4A using 4-boronobenzoic acid in place of 4-(methoxycarbonyl)phenylboronic acid and 6-bromo-4H-chromen-4-one in place of 1-bromo-3-iodobenzene.

Example 76B

N-[(4-{[adamantan-1-ylmethyl]amino}-3-nitrophenyl)sulfonyl]-4-(4-oxo-4H-chromen-6-yl)benzamide The title compound was prepared as described in EXAMPLE 1B using EXAMPLE 76A in place of EXAMPLE 1A and 4-[(adamantan-1-ylmethyl)amino]-3-nitrobenzenesulfonamide in place of 4-chloro-3-nitrobenzenesulfonamide. $^1$H NMR (300 MHz, dimethylsulfoxide-$d_6$) δ 11.95 (s, 1H), 8.52 (t, 1H), 8.40 (t, 1H), 8.33 (d, 1H), 8.25 (d, 1H), 8.15 (d, 1H), 8.00 (d, 2H), 7.89 (d, 1H), 7.73 (m, 2H), 7.16 (d, 1H), 6.40 (d, 1H), 4.03 (m, 1H), 3.13 (d, 2H), 1.99 (m, 3H), 1.65 (m, 3H), 1.58 (s, 6H).

Example 77

N-[(4-{[adamantan-1-ylmethyl]amino}-3-nitrophenyl)sulfonyl]-4-(1-octyl-1H-pyrazol-4-yl)benzamide

Example 77A 4-iodo-1-octyl-1H-pyrazole

To a slurry of NaH (60% in mineral oil, 271 mg, 6.77 mmol) in N,N-dimethylformamide (20 mL) was added 4-iodo-1H-pyrazole (1.25 g, 6.44 mmol), and the reaction was stirred for 30 minutes. 1-Octyl bromide (1.22 mL, 7.08 mmol) was then added and the reaction stirred for 24 hours. The mixture was poured into water (200 mL), and the resulting solution was extracted three times with ether. The combined ether extracts were washed three times with water and brine, dried over $Na_2SO_4$, filtered, and concentrated to give the title compound.

Example 77B 4-(1-octyl-1H-pyrazol-4-yl)benzoic Acid

The title compound was prepared as described in EXAMPLE 4A using 4-boronobenzoic acid in place of 4-(methoxycarbonyl)phenylboronic acid and EXAMPLE 77A in place of 1-bromo-3-iodobenzene.

Example 77C

N-[(4-[adamantan-1-ylmethyl]amino-3-nitrophenypsulfonyl]-4-(1-octyl-1H-pyrazol-4-yl)benzamide The title compound was prepared as described in EXAMPLE 1B using EXAMPLE 77B in place of EXAMPLE 1A and 4-[(adamantan-1-ylmethyl)amino]-3-nitrobenzenesulfonamide in place of 4-chloro-3-nitrobenzenesulfonamide. $^1$H NMR (300 MHz, dimethylsulfoxide-$d_6$) δ 11.95 (s, 1H), 8.55 (d, 1H), 8.43 (t, 1H), 8.23 (s, 1H), 7.90 (m, 3H), 7.55 (d, 2H), 7.19 (d, 1H), 4.03 (m, 1H), 3.14 (d, 2H), 1.97 (m, 3H), 1.78 (t, 2H), 1.65 (m, 5H), 1.58 (s, 6H), 1.23 (br s, 10H), 0.84 (t, 3H).

Example 78

4-[5-(4-{[(4-{[adamantan-1-ylmethyl]amino}-3-nitrophenyl)sulfonyl]carbamoyl}phenyl)-1,3-benzothiazol-2-yl]butanoic Acid

Example 78A

4-[(adamantan-1-ylmethyl)-amino]-3-nitro-benzenesulfonamide

The title compound was prepared by substituting 1-adamantanemethylamine for cyclohexylmethylamine in EXAMPLE 2D.

Example 78B 4-(5-Bromo-benzothiazol-2-yl)-butyric Acid Methyl Ester

5-Bromo-2-methylbenzothiazole (1000 mg) was dissolved in tetrahydrofuran (25 mL) and the mixture was cooled to −78° C. using an isopropanol/dry ice bath. Lithium diisopropylamide (1.5M in cyclohexane, 4.40 mL) was added, and the solution stirred for 30 minutes at −78° C. Methyl 3-bromopropionate (1.20 mL, 1836 mg) was added and the solution stirred at −78° C. for two hours. The reaction was quenched with 1M aqueous hydrochloric acid, extracted with ethyl acetate, washed with brine, dried over anhydrous sodium sulfate, filtered, concentrated, and purified by flash column chromatography on silica gel using 10% ethyl acetate hexanes.

Example 78C

4-[2-(3-Ethoxycarbonyl-propyl)-benzothiazol-5-yl]-benzoic Acid

EXAMPLE 78B (275 mg), 4-carboxyphenylboronic acid (160 mg), sodium carbonate (2M aqueous, 1.1 mL), and [1,1'-bis(diphenylphosphino)ferrocene]dichloropalladium (II) dichloromethane adduct (65 mg) were added to dimethylformamide (1.5 mL), ethanol (1.5 mL), and water (0.5 mL) which had been degassed and flushed with nitrogen three times. The solution was heated to 90° C. and stirred for 16 hours. The solution was cooled, added to water, extracted with ethyl acetate, washed with brine, dried on anhydrous sodium sulfate, filtered, concentrated, and purified by flash column chromatography on silica gel using 5% methanol in ethyl acetate to obtain the ethyl ester product via transesterification with the ethanol solvent.

Example 78D

4-[5-(4-{4-[(adamantan-1-ylmethyl)-amino]-3-nitro-benzenesulfonylaminocarbonyl}-phenyl)-benzothiazol-2-yl]-butyric Acid Ethyl Ester The title compound was prepared by substituting EXAMPLE 78C for EXAMPLE 1A and EXAMPLE 78A for 4-chloro-3-nitrobenzenesulfonamide in EXAMPLE 1B.

Example 78E

4-[5-(4-{[(4-{[adamantan-1-ylmethyl]amino}-3-nitrophenyl)sulfonyl]carbamoyl}phenyl)-1,3-benzothiazol-2-yl]-butanoic Acid The title compound was prepared by substituting EXAMPLE 78D for EXAMPLE 2A in EXAMPLE 2B. $^1$H NMR (300 MHz, dimethylsulfoxide-$d_6$) δ 12.52 (br s, 1H), 12.13 (br s, 1H), 8.68 (d, 1H), 8.59 (t, 1H), 8.31 (d, 1H), 8.17 (d, 1H), 8.00-7.91 (m, 5H), 7.78 (dd, 1H), 7.38 (d, 1H), 3.22-3.13 (m, 4H), 2.39 (t, 2H), 2.05 (m, 2H), 1.97 (br s, 4H), 2.66 (m, 4H), 1.58 (br s, 6H), 0.86 (m, 1H).

Example 79

N-{[3-nitro-4-(tetrahydro-2H-pyran-4-ylamino)phenyl]sulfonyl}-4-[(1R,5S)-1,8,8-trimethyl-3-azabicyclo[3.2.1]oct-3-yl]benzamide

Example 79A

Ethyl 4-((1R,5S)-1,8,8-trimethyl-3-azabicyclo[3.2.1]octan-3-yl)benzoate

The title compound was prepared by substituting (1R,5S)-1,8,8-trimethyl-3-azabicyclo[3.2.1]octane for benzyl 2,6-diazabicyclo[3.2.1]octane-6-carboxylate in EXAMPLE 8A.

Example 79B 4-41R,5S)-1,8,8-trimethyl-3-azabicy-clo[3.2.1]octan-3-yl)benzoic Acid The title compound was prepared by substituting EXAMPLE 79A for EXAMPLE 8D in EXAMPLE 8E.

Example 79C

N-{[3-nitro-4-(tetrahydro-2H-pyran-4-ylamino)phenyl]sulfonyl}-4-[(1R,5S)-1,8,8-trimethyl-3-azabicyclo[3.2.1]oct-3-yl]benzamide The title compound was prepared by substituting EXAMPLE 41A for EXAMPLE 2D and EXAMPLE 79B for EXAMPLE 8E in EXAMPLE 8F. $^1$H NMR (300 MHz, dimethylsulfoxide-$d_6$) δ 11.99 (br s, 1H), 8.63 (d, 1H), 8.28 (d, 1H), 7.95 (dd, 1H), 7.74 (d, 2H), 7.39 (d, 1H), 6.80 (d, 2H), 3.95 (m, 1H), 3.88 (m, 2H), 3.47 (m, 2H), 3.40 (d, 1H), 3.22 (d, 1H), 3.18 (d, 1H), 2.84 (d, 1H), 1.90 (m, 4H), 1.62 (m, 4H), 1.40 (m, 1H), 0.92 (s, 3H), 0.90 (s, 6H).

Example 80

6-{3-[adamantan-1-yl]-4-methoxyphenyl}-N-({4-[(cyclo hexylmethyl)amino]-3-nitrophenyl}sulfonyl)-2-naphthamide The title compound was prepared by substituting 6-(3-adaman-1-yl-4-methoxy-phenyl)-naphthalene-2-carboxylic acid for EXAMPLE 1A and EXAMPLE 2D for 4-chloro-3-nitrobenzenesulfonamide in EXAMPLE 1B. $^1$H NMR (300 MHz, dimethylsulfoxide-$d_6$) δ 12.57 (br s, 1H), 8.70 (d, 1H), 8.65 (t, 1H), 8.57 (s, 1H), 8.21 (s, 1H), 8.10 (d, 1H), 8.06 (d, 1H), 8.00 (dd, 1H), 7.88 (m, 2H), 7.66 (dd, 1H), 7.58 (d, 1H), 7.28 (d, 1H), 7.13 (d, 1H), 3.87 (s, 3H), 2.63 (br s, 6H), 2.07 (br s, 4H), 1.78-1.62 (m, 12H), 1.26-1.15 (m, 4H), 1.01 (t, 2H).

Example 81

4-{4-[adamantan-1-ylacetyl]piperazin-1-yl}-N-{[3-nitro-4-(tetrahydro-2H-pyran-4-ylamino)phenyl]sulfonyl}benzamide

Example 81A

4-[4-(adamantan-1-ylacetyl)piperazin-1-yl]benzoic Acid

The title compound was prepared by substituting EXAMPLE 58A for EXAMPLE 8D in EXAMPLE 8E.

Example 81B

4-{4-[adamantan-1-ylacetyl]piperazin-1-yl}-N-{[3-nitro-4-(tetrahydro-2H-pyran-4-ylamino)phenyl]sulfonyl}benzamide The title compound was prepared by substituting EXAMPLE 41A for EXAMPLE 2D and EXAMPLE 81A for EXAMPLE 8E in EXAMPLE 8F. $^1$H NMR (300 MHz, dimethylsulfoxide-$d_6$) δ 12.05 (br s, 1H), 8.64 (d, 1H), 8.30 (d, 1H), 7.95 (dd, 1H), 7.76 (d, 2H), 7.40 (d, 1H), 6.95 (d, 2H), 3.94 (m, 1H), 3.87 (m, 2H), 3.60 (m, 4H), 3.45 (m, 2H), 3.29 (m, 4H), 2.15 (s, 2H), 1.90 (m, 5H), 1.60 (m, 14H).

Example 82

4-{[adamantan-1-ylmethyl]amino}-N-{[3-nitro-4-(tetrahydro-2H-pyran-4-ylamino)phenyl]sulfonyl}benzamide

Example 82A

Ethyl 4-{[adamantan-1-ylmethyl]amino}benzoate

The title compound was prepared by substituting 1-adamantanemethylamine for (2-adamantylmethyl)amine hydrochloride in EXAMPLE 50A.

Example 82B

4-{[adamantan-1-ylmethyl]amino}benzoic Acid

The title compound was prepared by substituting EXAMPLE 82A for EXAMPLE 50A in EXAMPLE 50B.

Example 82C

4-{[adamantan-1-ylmethyl]amino}-N-{[3-nitro-4-(tetrahydro-2H-pyran-4-ylamino)phenyl]sulfonyl}benzamide The title compound was prepared by substituting EXAMPLE 82B for EXAMPLE 1A and EXAMPLE 41A for 4-chloro-3-nitrobenzenesulfonamide in EXAMPLE 1B.

Example 83

N-{1-[4-({[3-nitro-4-(tetrahydro-2H-pyran-4-ylamino)phenyl]sulfonyl}carbamoyl)phenyl]piperidin-4-yl}adamantane-1-carboxamide

Example 83A

Ethyl 4-(4-(tert-butoxycarbonylamino)piperidin-1-yl)benzoate

The title compound was prepared by substituting tert-butyl piperidin-4-ylcarbamate for benzyl 2,6-diazabicyclo[3.2.1]octane-6-carboxylate in EXAMPLE 8A.

Example 83B

Ethyl 4-(4-aminopiperidin-1-yl)benzoate

The title compound was prepared by substituting EXAMPLE 83A for EXAMPLE 11A in EXAMPLE 11B.

Example 83C

Ethyl 4-{4-[(adamantan-1-ylcarbonyl)amino]piperidin-1-yl}benzoate

The title compound was prepared by substituting EXAMPLE 83B for EXAMPLE 8B in EXAMPLE 8C.

Example 83D

4-{4-[(adamantan-1-ylcarbonyl)amino]piperidin-1-yl}benzoic Acid

The title compound was prepared by substituting EXAMPLE 83C for EXAMPLE 8D in EXAMPLE 8E.

Example 83E

N-{1-[4-({[3-nitro-4-(tetrahydro-2H-pyran-4-ylamino)phenyl]sulfonyl}carbamoyl)phenyl]piperidin-4-yl}adamantane-1-carboxamide The title compound was prepared by substituting EXAMPLE 41A for EXAMPLE 2D and EXAMPLE 83D for EXAMPLE 8E in EXAMPLE 8F. $^1$H NMR (300 MHz, dimethylsulfoxide-d$_6$) δ 12.00 (br s, 1H), 8.64 (d, 1H), 8.30 (d, 1H), 7.95 (dd, 1H), 7.76 (d, 2H), 7.39 (d, 1H), 7.10 (d, 1H), 6.92 (d, 2H), 3.90 (m, 6H), 3.45 (m, 2H), 2.92 (m, 2H), 1.90 (br s, 6H), 1.70 (m, 15H), 1.45 (m, 2H).

Example 84

4-[adamantan-2-ylamine]-N-{[3-nitro-4-(tetrahydro-2H-pyran-4-ylamino)phenyl]sulfonyl}benzamide

Example 84A

Ethyl 4-[adamantan-2-ylamino]benzoate

The title compound was prepared by substituting 2-adamantanamine hydrochloride for (2-adamantylmethyl)amine hydrochloride in EXAMPLE 50A.

Example 84B

4-[adamantan-2-ylamino]benzoic acid

The title compound was prepared by substituting EXAMPLE 84A for EXAMPLE 50A in EXAMPLE 50B.

Example 84C

4-[adamantan-2-ylamino]-N-{[3-nitro-4-(tetrahydro-2H-pyran-4-ylamino)phenyl]sulfonyl}benzamide The title compound was prepared by substituting EXAMPLE 84B for EXAMPLE 1A and EXAMPLE 41A for 4-chloro-3-nitrobenzenesulfonamide in EXAMPLE 1B. $^1$H NMR (500 MHz, dimethylsulfoxide-d$_6$) δ 11.82 (s, 1H), 8.63 (d, 1H), 8.29 (d, 1H), 7.94 (dd, 1H), 7.61 (d, 2H), 7.38 (d, 1H), 6.64 (d, 2H), 3.95 (m, 1H), 3.88 (m, 2H), 3.36 (m, 1H), 3.47 (m, 2H), 2.01 (m, 2H), 1.92 (m, 4H), 1.83 (m, 6H), 1.70 (m, 4H), 1.50 (m, 2H).

Example 85

N-{[3-nitro-4-(tetrahydro-2H-pyran-4-ylamino)phenyl]sulfonyl}-4-{[(1R,2R,3R,5S)-2,6,6-trimethylbicyclo[3.1.1]hept-3-yl]oxy}benzamide

Example 85A

Ethyl 4-((1R,2R,3R,5S)-2,6,6-trimethylbicyclo[3.1.1]heptan-3-yloxy)benzoate

Ethyl 4-iodobenzoate (276 mg), (1R,2R,3R,5S)-2,6,6-trimethylbicyclo[3.1.1]heptan-3-ol (154 mg), 1,10-phenanthroline (36 mg), copper iodide (19 mg) and cesium carbonate (652 mg) were combined in toluene (0.5 mL). The reaction was heated to 120° C. over 36 hours. The reaction mixture was removed from heat, allowed to cool, diluted with ethyl acetate and poured into water. The organic layer was washed thoroughly with water and brine, dried over MgSO$_4$, filtered and concentrated under vacuum. The crude material was purified by flash chromatography eluting with 95/5 hexanes/ether.

Example 85B 4-((1R,2R,3R,5S)-2,6,6-trimethylbicyclo[3.1.1]heptan-3-yloxy)benzoic Acid The title compound was prepared by substituting EXAMPLE 85A for EXAMPLE 50A in EXAMPLE 50B.

Example 85C

N-{[3-nitro-4-(tetrahydro-2H-pyran-4-ylamino)phenyl]sulfonyl}-4-{[(1R,2R,3R,5S)-2,6,6-trimethylbicyclo[3.1.1]hept-3-yl]oxy}benzamide The title compound was prepared by substituting EXAMPLE 85B for EXAMPLE 1A and EXAMPLE 41A for 4-chloro-3-nitrobenzenesulfonamide in EXAMPLE 1B. $^1$H NMR (500 MHz, dimethylsulfoxide-d$_6$) δ 12.26 (br s, 1H), 8.66 (d, 1H), 8.30 (d, 1H), 7.95 (dd, 1H), 7.82 (d, 2H), 7.40 (d, 1H), 7.03 (d, 2H), 4.67 (m, 1H), 3.96 (m, 1H), 3.88 (m, 2H), 3.47 (m, 3H), 2.65 (m, 1H), 2.36 (m, 1H), 2.25 (m, 1H), 1.93 (m, 3H), 1.85 (m, 1H), 1.64 (m, 3H), 1.23 (s, 3H), 1.10 (d, 3H), 0.99 (s, 3H).

What is claimed is:

1. A method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T cell or B cell origin, melanoma, myelogenous leukemia, myeloma, oral cancer, ovarian cancer, non small cell lung cancer, chronic lymphocytic leukemia, myeloma, prostate cancer, small cell lung cancer or spleen cancer in a patient, said method comprising administering to the patient a therapeutically effective amount of a compound, or a therapeutically acceptable salt thereof, wherein the compound is selected from the group consisting of:

4-{4-[(4'-chlorobiphenyl-2-yl)methyl]piperazin-1-yl}-N-[(3-nitro-4-{[(1R,2R,3R,5S)-2,6,6-trimethylbicyclo[3.1.1]hept-3-yl]amino}phenyl)sulfonyl]benzamide;

4-(4-{acetyl[(1S,2S,3S,5R)-2,6,6-trimethylbicyclo[3.1.1]hept-3-yl]amino}piperidin-1-yl)-N-({4-[(cyclohexylmethyl)amino]-3-nitrophenyl}sulfonyl)benzamide:

4-(4-{benzoyl[(1S,2S,3S,5R)-2,6,6-trimethylbicyclo[3.1.1]hept-3-yl]amino}piperidin-1-yl)-N-({4-[(cyclohexylmethyl)amino]-3-nitrophenyl}sulfonyl)benzamide:

N-({4-[(cyclohexylmethyl)amino]-3-nitrophenyl}sulfonyl)-3'-{[(1S,2S,3S,5R)-2,6,6-trimethylbicyclo[3.1.1]hept-3-yl]amino}biphenyl-4-carboxamide;

N-({4-[(cyclohexylmethyl)amino]-3-nitrophenyl}sulfonyl)-4-(4-{(phenylacetyl)[(1S,2S,3S,5R)-2,6,6-trimethylbicyclo[3.1.1]hept-3-yl]amino}piperidin-1-yl)benzamide:

N-({4-[(cyclohexylmethyl)amino]-3-nitrophenyl}sulfonyl)-4'-{[(1S,2S,3S,5R)-2,6,6-trimethylbicyclo[3.1.1]hept-3-yl]amino}biphenyl-4-carboxamide;

N-({4-[(cyclohexylmethyl)amino]-3-nitrophenyl}sulfonyl)-4'-{(3-phenylpropyl)[(1S,2S,3S,5R)-2,6,6-trimethylbicyclo[3.1.1]hept-3-yl]amino}biphenyl-4 carboxamide;

4-{6-[adamantan-1-ylmethyl]-2,6-diazabicyclo[3.2.1]oct-2-yl}-N-({4-[(cyclohexylmethyl)amino]-3-nitrophenyl}sulfonyl)benzamide;

N-[(4-{[(2R)-4-(morpholin-4-yl)-1-(phenylthio)butan-2-yl]amino}-3-[(trifluoromethyl)sulfonyl]phenyl]sulfonyl]-4-(4-{(3-phenylpropanoyl)[1S,2S,3S,5R)-2,6,6-trimethylbicyclo[3.1.1]hept-3-yl]amino}piperidin-1-yl)benzamide;

4-{4-[adamantan-1-yl]piperazin-1-yl}-N-[(4-{[(2R)-4-(morpholin-4-yl)-1-(phenylthio)butan-2-yl]amino}-3-nitrophenyl)sulfonyl]benzamide;

4-{(1S,4S)-5-[adamantan-1-ylmethyl]-2,5-diazabicyclo[2.2.1]hept-2-yl}-N-({4-[(cyclohexylmethyl)amino]-3-nitrophenyl}sulfonyl)benzamide;

4-(4-{[(1R,5R)-3-bromo-5-methyladamantan-1-yl]methyl}piperazin-1-yl)-N-({4-[(cyclohexylmethyl)amino]-3-nitrophenyl}sulfonyl)benzamide;

N-({4-[(cyclohexylmethyl)amino]-3-nitrophenyl}sulfonyl)-4-(4-{[3,5-dimethyladamantan-1-yl]methyl}piperazin-1-yl)benzamide;

4-{4-[(4'-chlorobiphenyl-2-yl)methyl]piperazin-1-yl}-N-{[4-(1-methyl-2-oxo-3-azabicyclo[3.1.1]hept-3-yl)phenyl]sulfonyl}benzamide;

N-({3-nitro-4-[(tetrahydro-2H-pyran-4-ylmethyl)amino]phenyl}sulfonyl)-4-(4-{2-[(1R,4R)-1,7,7-trimethylbicyclo[2.2.1]hept-2-en-2-yl]benzyl}piperazin-1-yl)benzamide;

N-({3-nitro-4-[(tetrahydro-2H-pyran-4-ylmethyl)amino]phenyl}sulfonyl)-4-(4-{2-octahydro-1H-4,7-methanoinden-5-ylamino]benzyl}piperazin-1-yl)benzamide;

N-({3-nitro-4-[(tetrahydro-2H-pyran-4-ylmethyl)amino]phenyl}sulfonyl)-4-[4-(2-{[(1R,4R,6S)-5,5,6-trimethylbicyclo[2.2.1]hept-2-yl]amino}benzyl)piperazin-1-yl]benzamide;

4-[4-(2-{[(1R,5S)-6,6-dimethylbicyclo[3.1.1]hept-2-yl]amino}benzyl)piperazin-1-yl]-({3-nitro-4-[(tetrahydro-2H-pyran-4-ylmethyl)amino]phenyl}sulfonyl)benzamide;

4-(4-{[(1R,5R)-2-(4-chlorophenyl)-6,6-dimethylbicyclo[3.1.1]hept-2-en-3-yl]methyl}piperazin-1-yl)-N-({4-[(cyclohexylmethyl)amino]-3-nitrophenyl}sulfonyl)benzamide;

4-{4-[(2-{[adamantan-2-ylmethyl]amino}-5,5-dimethylcyclohexyl)methyl]piperazin-1-yl}-N-({3-nitro-4-[(tetrahydro-2H-pyran-4-ylmethyl)amino]phenyl}sulfonyl)benzamide;

4-{4-[(5,5-dimethyl-2-{[(1R,2S,3S,5S)-2,6,6-trimethylbicyclo[3.1.1]hept-3-yl]amino}cyclohexyl)methyl]piperazin-1-yl}-N-({3-nitro-4-[(tetrahydro-2H-pyran-4-ylmethyl)amino]phenyl}sulfonyl)benzamide;

4-{4-[2-(3-azabicyclo[3.2.2]non-3-yl)-5-nitrobenzyl]piperazin-1-yl}-N-({3-nitro-4-[(tetrahydro-2H-pyran-4-ylmethyl)amino]phenyl}sulfonyl)benzamide;

4-(4-{2-[2,3,3a,4,7,7a-hexahydro-1H-4,7-methanoinden-5-yl]benzyl}piperazin-1-yl)-N-({3-nitro-4-[(tetrahydro-2H-pyran-4-ylmethyl)amino]phenyl}sulfonyl)benzamide;

1-[adamantan-1-yl]-4-{2-[(4-{4-[({3-nitro-4-[(tetrahydro-2H-pyran-4-yimethyl)amino]phenyl}sulfonyl)carbamoyl]phenyl}piperazin-1-yl)methyl]phenyl}-N,N-diphenyl-1H-pyrazole-3-carboxamide;

4-(4-{2-[2-(adamantan-1-yl)-6-methylimidazo[1,2-a]pyridin-8-yl]benzyl}piperazin-1-yl)-N-({3-nitro-4-[(tetrahydro-2H-pyran-4-ylmethyl)amino]phenyl}sulfonyl)benzamide;

N-(adamantan-2-yl)-6-methyl-8-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}imidazo[1,2-a]pyridine-2-carboxamide;

4-(4-{2-[(1R,5S)-6,6-dimethylbicyclo[3.1.1]hept-2-en-2-yl]benzyl}piperazin-1-yl)-N-({3-nitro-4-[(tetrahydro-2H-pyran-4-ylmethyl)amino]phenyl}sulfonyl)benzamide;

N-({3-nitro-4-[(tetrahydro-2H-pyran-4-ylmethyl)amino]phenyl}sulfonyl)-4-(4-{2-[5,5,6-trimethylbicyclo[2.2.1]hept-2-en-2-yl]benzyl}piperazin-1-yl)benzamide;

N-cyclootyl-5-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}-2-furamide;

N-benzyl-7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}bicyclo[2.2.1]hept-2-ene-1-carboxamide;

4-[4-(2-{[(1R,5S)-8-methyl-8-azabicyclo[3.2.1]oct-3-yl]amino}benzyl)piperazin-1-yl]-N-({3-nitro-4-[(tetrahydro-2H-pyran-4-ylmethyl)amino]phenyl}sulfonyl)benzamide;

N-({3-nitro-4-[(tetrahydro-2H-pyran-4-ylmethyl)amino]phenyl}sulfonyl)-4-[4-(2-{[(1R,2S,3S,5S)-2,6,6-trimethylbicyclo[3.1.1]hept-3-yl]amino}benzyl)piperazin-1-yl]benzamide;

4-(4-{2-[3-azabicyclo[3.2.2]non-3-yl]benzyl}piperazin-1-yl)-N-({3-nitro-4-[(tetrahydro-2H-pyran-4-ylmethyl)amino]phenyl}sulfonyl)benzamide;

N-({3-nitro-4-[(tetrahydro-2H-pyran-4-ylmethyl)amino]phenyl}sulfonyl)-4-(4-{2-[tricyclo[4.3.1.13,8]undec-4-en-4-yl]benzyl}piperazin-1-yl)benzamide;

7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}-N-phenylbicyclo[2.2.1]hept-2-ene-1-carboxamide;

7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}-N-[(1S,2S,3S,5R)-2,6,6-trimethylbicyclo[3.1.1]hept-3-yl]bicyclo[2.2.1]hept-2-ene-1-carboxamide;

N-(adamantan-1-ylmethyl)-7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}bicyclo[2.2.1]hept-2-ene-1-carboxamide;

N-cyclopropyl-7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}bicyclo[2.2.1]hept-2-ene-1-carboxamide;

7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}bicyclo[2.2.1]hept-2-ene-1-carboxylic;

4-[4-(2-{5-[8-azabicyclo[3.2.1]oct-8-ylmethyl]-2-thienyl}benzyl)piperazin-1-yl]-N-({3-nitro-4-[(tetrahydro-2H-pyran-4-ylmethyl)amino]phenyl}sulfonyl)benzamide;

4-{4-[adamantan-1-ylcarbonyl]piperazin-1-yl}-N-{[3-nitro-4-(tetrahydro-2H-pyran-4-ylamino)phenyl]sulfonyl}benzamide;

4-{4-[adamantan-2-ylcarbonyl]piperazin-1-yl}-N-{[3-nitro-4-(tetrahydro-2H-pyran-4-ylamino)phenyl]sulfonyl}benzamide;

4-{5-[adamantan-1-ylcarbonyl]-2,5-diazabicyclo[2.2.1]hept-2-yl}-N-{[3-nitro-4-tetrahydro-2H-pyran-4-ylamino)phenyl]sulfonyl}benzamide;

4-{1S,5S)-3-[adamantan-1-ylcarbonyl]-3,6-diazabicyclo[3.2.0]hept-6-yl}-N-{[3-nitro-4-(tetrahydro-2H-pyran-4-ylamino)phenyl]sulfonyl}benzamide;

N-{[3-nitro-4-(tetrahydro-2H-pyran-4-ylamino)phenyl]sulfonyl}-4-(4-{(3-phenylpropyl)[(1S,2S,3S,5R)-2,6,6-trimethylbicyclo[3.1.1]hept-3-yl]amino}piperidin-1-yl)benzamide;

N-{4-[(cyclohexylmethyl)amino]-3-nitrophenyl}sulfonyl)-4-(4-{(3-phenylpropanoyl)[(1S,2S,3S,5R)-2,6,6-trimethylbicyclo[3.1.1]hept-3-yl]amino}piperidin-1-yl)benzamide;

4-{4-[adamantan-1-ylmethyl]piperazin-1-yl}-N-({4-[(cyclohexylmethyl)amino]-3-nitrophenyl}sulfonyl)benzamide;

6-{3-[adamantan-1-yl]-4-hydroxyphenyl}-N-({4-[(cyclohexylmethyl)amino]-3-nitrophenyl}sulfonyl)-2-naphthamide;

4-(4-{2-[adamantan-1-yl]-2-oxoethyl}piperazin-1-yl)-N-({4-[(cyclohexylmethyl)amino]-3-nitrophenyl}sulfonyl)benzamide;

4-{[adamantan-2-ylmethyl]amino}-N-{[3-nitro-4-(tetrahydro-2H-pyran-4-ylamino)phenyl]sulfonyl}benzamide;

4-{2-[adamantan-1-yl]ethoxy}-N-{[3-nitro-4-tetrahydro-2H-pyran-4-ylamino)phenyl]sulfonyl}benzamide;

N3-[adamantan-1-ylacetyl]-N3-benzyl-N-({4-[(cyclohexylmethyl)amino]-3-nitrophenyl}sulfonyl)-beta-alaninamide;

N-({4-[(cyclohexylmethyl)amino]-3-nitrophenyl}sulfonyl)-4-{4-[(1S,2S,3S,5R)-2,6,6-trimethylbicyclo[3.1.1]hept-3-yl]piperazin-1-yl}benzamide;

4-{4-[adamantan-1-yl]piperazin-1-yl}-N-({4-[(cyclohexylmethyl)amino]-3-nitrophenyl}sulfonyl)benzamide;

N-({4-[(cyclohexylmethyl)amino]-3-nitrophenyl}sulfonyl)-4-{4-[3,5-dimethyladamantan-1-yl]piperazin-1-yl}benzamide:

[(3aS,5aR,8aR,8bS)-2,2,7,7-tetramethyltetrahydro-3aH-bis[1,3]dioxolo[4,5-b4',5'-d]pyran-3a-yl]methyl;

4-{4-[(4'-chlorobiphenyl-2-yl)methyl]piperazin-1-yl}-N-({[(1R,4S)-7,7-dimethyl-2-oxobicyclo[2.2.1]hept-1-yl]methyl}sulfonyl)benzamide;

4-(4-{2-[adamantan-1-yl]ethyl}piperazin-1-yl)-N-({4-[(cyclohexylmethyl)amino]-3-nitrophenyl}sulfonyl)benzamide;

4-{4-[(4'-chlorobiphenyl-2-yl)methyl]piperazin-1-yl}-N-({[(1S,4R)-7,7-dimethyl-2-oxobicyclo[2.2.1]hept-1-yl]methyl}sulfonyl)benzamide;

N-({4-[(cyclohexylmethyl)amino]-3-nitrophenyl}sulfonyl)-4'-({(3-phenylpropanoyl)[(1S,2S,3S,5R)-2,6,6-trimethylbicyclo[3.1.1]hept-3-yl]amino}methyl)biphenyl-4-carboxamide;

N-({3-nitro-4-[(tetrahydro-2H-pyran-4-ylmethyl)amino]phenyl}sulfonyl)-4-(4-{2-[(1R,4R)-1,7,7-trimethylbicyclo[2.2.1]hept-2-en-2-yl]benzylidene}piperidin-1-yl)benzamide;

N-({3-nitro-4-[(tetrahydro-2H-pyran-4-ylmethyl)amino]phenyl}sulfonyl-4-(4-{2-[5-(4-phenyl-1,3-thiazol-2-yl)-2-thienyl]benzyl}piperazin-1-yl)benzamide;

4-[4-(2-{5-[4-(adamantan-1-yl)-1,3-thiazol-2-yl]-2-thienyl}benzyl)piperazin-1-yl]-N-({3-nitro-4-[(tetrahydro-2H-pyran-4-ylmethyl)amino]phenyl}sulfonyl)benzamide;

5-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}-N-(2 phenyl-1,3-benzoxazol-5-yl)-2-furamide;

N-({3-nitro-4-[(tetrahydro-2H-pyran-4-ylmethyl)amino]phenyl}sulfonyl)-4-{4-[2-(triphenylvinyl)benzyl]piperazin-1-yl}benzamide:

4-{4-[2-(5-methyl-5,6-dihydrophenanthridin-6-yl benzyl]piperazin-1-yl}-N-({3-nitro-4-[(tetrahydro-2H-pyran-4-ylmethyl)amino]phenyl}sulfonyl)benzamide;

N-({3-nitro-4-[(tetrahydro-2H-pyran-4-ylmethyl)amino]phenyl}sulfonyl)-4-{4-[2-(4,4,5,5-tetramethyl-1,3,2-dioxaborolan-2-yl)benzyl]piperazin-1-yl}benzamide;

4-(4-{2-[2-(2,6-dimethoxybenzoyl)-3-thienyl]benzylidene}piperidin-1-yl)-N-({3-nitro-4-[(tetrahydro-2H-pyran-4-ylmethyl)amino]phenyl}sulfonyl)benzamide;

1-[adamantan-1-yl]-4-{2-[(1-{4-[({3-nitro-4-[(tetrahydro-2H-pyran-4-ylmethyl)amino]phenyl}sulfonyl)carbamoyl]phenyl}piperidin-4-ylidene)methyl]phenyl}-N,N-diphenyl-1H-pyrazole-3-carboxamide;

N-({3-nitro-4-[(tetrahydro-2H-pyran-4-ylmethyl)amino]phenyl}sulfonyl)-4-(4-{2-[octahydro-1H-4,7-methanoinden-5-yl(3-phenylpropanoyl)amino]benzyl}piperazin-1-yl)benzamide;

4-[4-(2-{5-[8-azabicyclo[3.2.1]oct-8-ylmethyl]-2-thienyl}benzylidene)piperidin-1-yl]-N-({3-nitro-4-[(tetrahydro-2H-pyran-4-ylmethyl)amino]phenyl}sulfonyl)benzamide;

N-({3-nitro-4-[(tetrahydro-2H-pyran-4 ylmethyl)amino]phenyl}sulfonyl)-4-[4-(4-{[(1S,2S,3S 5R)-2,6,6-trimethylbicyclo[3.1.1]hept-3-yl]amino}benzylidene)piperidin-1-yl]benzamide;

N-({3-nitro-4-[(tetrahydro-2H-pyran-4-ylmethyl)amino]phenyl}sulfonyl)-4-[4-(3-{[(1S,2S 3S,5R)-2,6,6-trimethylbicyclo[3.1.1]hept-3-yl]amino}benzylidene)piperidin-1-yl]benzamide;

4-[4-(2-{5-[4-(adamantan-1-yl)-1,3-thiazol-2-yl]-2-thienyl}benzylidene)piperidin-1-yl]-N-({3-nitro-4-[(tetrahydro-2H-pyran-4-ylmethyl)amino]phenyl}sulfonyl)benzamide:

N-({3-nitro-4-[(tetrahydro-2H-pyran-4-ylmethyl)amino]phenyl}sulfonyl)-4-(4-{2-[5-(4-phenyl-1,3-thiazol-2-yl)-2-thienyl]benzylidene}piperidin-1-yl)benzamide;

N-[(4-{[adamantan-1-ylmethyl]amino}-3-nitrophenyl)sulfonyl]-4-(4-oxo-4H-chromen-6-yl)benzamide;

N-[(4-{[adamantan-1-ylmethyl]amino}-3-nitrophenyl)sulfonyl]-4-(1-octyl-1H-pyrazol-4-yl)benzamide;

4-[5-(4-{[(4-{[adamantan-1-ylmethyl]amino}-3-nitrophenyl)sulfonyl]carbamoyl}phenyl)-1,3-benzothiazol-2-yl]butanoic;

N-{[3-nitro-4-(tetrahydro-2H-pyran-4-ylamino)phenyl]sulfonyl}-4-[(1R,5S)-1,8,8-trimethyl-3-azabicyclo[3.2.1]oct-3-yl]benzamide;

6-{3-[adamantan-1-yl]-4-methoxyphenyl}-N-({4-[(cyclohexylmethyl)amino]-3-nitrophenyl}sulfonyl)-2-naphthamide:

4-{4-[adamantan-1-ylacetyl]piperazin-1-yl}-N-{[3-nitro-4-(tetrahydro-2H-pyran-4-ylamino)phenyl]sulfonyl}benzamide;

4-{[adamantan-1-ylmethyl]amino}-N-{[3-nitro-4-(tetrahydro-2H-pyran-4-ylamino)phenyl]sulfonyl}benzamide;

N-{1-[4-({[3-nitro-4-(tetrahydro-2H-pyran-4-ylamino)phenyl]sulfonyl}carbamoyl)phenyl]piperidin-4-yl}adamantane-1-carboxamide:

4-[adamantan-2-ylamino]-N-{[3-nitro-4-(tetrahydro-2H-pyran-4-ylamino)phenyl]sulfonyl}benzamide; and N-{[3-nitro-4-(tetrahydro-2H-pyran-4-ylamino)phenyl]sulfonyl}-4-{[(1R,2R,3R,5S)-2,6,6-trimethylbicyclo[3.1.1]hept-3-yl]oxy}benzamide.

2. A method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T cell or B cell origin, melanoma, myelogenous leukemia, myeloma, oral cancer, ovarian cancer, non small cell lung cancer, chronic lymphocytic leukemia, myeloma, prostate cancer, small cell lung cancer or spleen cancer in a patient, said method comprising administering to the patient therapeutically effective amount of a compound, or a therapeutically acceptable salt thereof, wherein the compound is selected from the group consisting of:

4-{4-[(4'-chlorobiphenyl-2-yl)methyl]piperazin-1-yl}-N-[(3-nitro-4-{[(1R,2R,3R,5S)-2,6,6-trimethylbicyclo[3.1.1]hept-3-yl]amino}phenyl)sulfonyl]benzamide;

4-(4-{acetyl[(1S,2S,3S,5R)-2,6,6-trimethylbicyclo[3.1.1]hept-3-yl]amino}piperidin-1-yl)-N-({4-[(cyclohexylmethyl)amino]-3-nitrophenyl}sulfonyl)benzamide;

4-(4-{benzoyl[(1S,2S,3S,5R)-2,6,6-trimethylbicyclo[3.1.1]hept-3-yl]amino}piperidin-1-yl)-N-({4-[(cyclohexylmethyl)amino]-3-nitrophenyl}sulfonyl)benzamide;

N-({4-[(cyclohexylmethyl)amino]-3-nitrophenyl}sulfonyl)-3'-{[(1S,2S,3S,5R)-2,6,6-trimethylbicyclo[3.1.1]hept-3-yl]amino}biphenyl-4-carboxamide;

N-({4-[(cyclohexylmethyl)amino]-3-nitrophenyl}sulfonyl)-4-(4-{(phenylacetyl)[(1S,2S,3S,5R)-2,6,6-trimethylbicyclo[3.1.1]hept-3-yl]amino}piperidin-1-yl)benzamide;

N-({4-[(cyclohexylmethyl)amino]-3-nitrophenyl}sulfonyl)-4'-{[(1S,2S,3S,5R)-2,6,6-trimethylbicyclo[3.1.1]hept-3-yl]amino}biphenyl-4-carboxamide;

N-({4-[(cyclohexylmethyl)amino]-3-nitrophenyl}sulfonyl)-4'-{(3-phenylpropyl)[(1S,2S,3S,5R)-2,6,6-trimethylbicyclo[3.1.1]hept-3-yl]amino}biphenyl-4-carboxamide;

4-{6-[adamantan-1-ylmethyl]-2,6-diazabicyclo[3.2.1]oct-2-yl}-N-({4-[(cyclohexylmethyl)amino]-3-nitrophenyl}sulfonyl)benzamide;

N-[4-{[(2R)-4-(morpholin-4-yl)-1-(phenylthio)butan-2-yl]amino}-3-[(trifluoromethyl)sulfonyl]phenyl)sulfonyl]-4-(4-{(3-phenylpropanoyl)[(1S,2S,3S,5R)-2,6,6-trimethylbicyclo[3.1.1]hept-3-yl]amino}piperidin-1-yl)benzamide;

4-{4-[adamantan-1-ylmethyl]piperazin-1-yl}-N-[(4-{[(2R)-4-(morpholin-4-yl)-1-(phenylthio)butan-2-yl]amino}-3-nitrophenyl)sulfonyl]benzamide;

4-{(1S,4S)-5-[adamantan-1-ylmethyl]-2,5-diazabicyclo[2.2.1]hept-2-yl}-N-({4-[(cyclohexylmethyl)amino]-3-nitrophenyl}sulfonyl)benzamide;

4-(4-{[(1R,5R)-3-bromo-5-methyladamantan-1-yl]methyl}piperazin-1-yl)-N-({4-[(cyclohexylmethyl)amino]-3-nitrophenyl}sulfonyl)benzamide;

N-({4-[(cyclohexylmethyl)amino]-3-nitrophenyl}sulfonyl)-4-(4-{[3,5-dimethyladamantan-1-yl]methyl}piperazin-1-yl)benzamide;

4-{4-[(4'-chlorobiphenyl-2-yl)methyl]piperazin-1-yl}-N-{[4-(1-methyl-2-oxo-3-azabicyclo[3.1.1]hept-3-yl)phenyl]sulfonyl}benzamide;

N-({3-nitro-4-[(tetrahydro-2H-pyran-4-ylmethyl)amino]phenyl}sulfonyl)-4-(4-{2-[(1R,4R)-1,7,7-trimethylbicyclo[2.2.1]hept-2-en-2-yl]benzyl}piperazin-1-yl)benzamide;

N-({3-nitro-4-[(tetrahydro-2H-pyran-4-ylmethyl)amino]phenyl}sulfonyl)-4-(4-{2-octahydro-1H-4,7-methanoinden-5-ylamino]benzyl}piperazin-1-yl)benzamide;

N-({3-nitro-4-[(tetrahydro-2H-pryan-4-ylmety)amino]phenyl}sulfonyl)-4-[4-(2-{[(1R,4R,6S)-5,5,6-trimethylbicyclo[2.2.1]hept-2-yl]amino}benzyl)piperazin-1-yl]benzamide;

4-[4-(2-{[(1R,5S)-6,6-dimethylbicyclo[3.1.1]hept-2-yl]amino}benzyl)piperazin-1-yl]-N-{3-nitro-4-[(tetrahydro-2H-pyran-4-ylmeyl)amino]phenyl}sulfonyl)benzamide;

4-(4-{[(1R,5R)-2-(4-chlorophenyl)-6,6-dimethylbicyclo[3.1.1]hept-2-en-3-yl]methyl}piperazin-1-yl)-N-({4-[(cyclohexylmethyl)amino]-3-nitrophenyl}sulfonyl)benzamide:

4-{4-[(2-{[adamantan-2-ylmethyl]amino}-5,5-dimethylcyclohexyl)methyl]piperazin-1-yl}-N-({3-nitro-4-[(tetrahydro-2H-pyran-4-methyl)amino]phenyl}sulfonyl)benzamide;

4-{4-[(5,5-dimethyl-2-{[(1R,2S,3S,5S)-2,6,6-trimethylbicyclo[3.1.1]hept-3-yl]amino}cyclohexyl)methyl]piperazin-1-yl}-N-({3-nitro-4-[(tetrahydro-2H-pyran-4-ylmethyl)amino]phenyl}sulfonyl)benzamide;

4-{4-[2-(3-azabicyclo[3.2.2]non-3-yl)-5-nitrobenzyl]piperazin-1-yl}-N-({3-nitro-4-[(tetrahydro-2H-pyran-4-ylmethyl)amino]phenyl}sulfonyl)benzamide;

4-(4-{2-[2,3,3a,4,7,7a-hexahydro-1H-4,7-methanoinden-5-yl]benzyl}piperazin-1-yl)-N-({3-nitro-4-[(tetrahydro-2H-pyran-4-ylmethyl)amino]phenyl}sulfonyl)benzamide;

1-[adamantan-1-yl]-4-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}-N,N-diphenyl-1H-pyrazole-3-carboxamide;

4-(4-{2-[2-(adamantan-1-yl)-6-methylimidazo[1,2-a]pyridin-8-yl]benzyl}piperazin-1-yl)-N-({3-nitro-4-[(tetrahydro-2H-pyran-4-ylmethyl)amino]phenyl}sulfonyl)benzamide;

N-(adamantan-2-yl)-6-methyl-8-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}imidazo[1,2-a]pyridine-2-carboxamide;

4-(4-{2-[(1R,5S)-6,6-dimethylbicyclo[3.1.1]hept-2-en-2-yl]benzyl}piperazin-1-yl)-N-({3-nitro-4-[(tetrahydro-2H-pyran-4-ylmethyl)amino]phenyl}sulfonyl)benzamide;

N-({3-nitro-4-[(tetrahydro-2H-pyran-4-ylmethyl)amino]phenyl}sulfonyl)-4-(4-{2-[5,5,6-trimethylbicyclo[2.2.1]hept-2-en-2-yl]benzyl}piperazin-1-yl)benzamide;

N-cyclooctyl-5-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}-2-furamide;

N-benzyl-7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}bicyclo[2.2.1]hept-2-ene-1-carboxamide;

4-[4-(2-{[(1R,5S)-8-methyl-8-azabicyclo[3.2.1]oct-3-yl]amino}benzyl)piperazin-1-yl]-N-({3-nitro-4-[(tetrahydro-2H-pyran-4-ylmethyl)amino]phenyl}sulfonyl)benzamide;

N-({3-nitro-4-[(tetrahydro-2H-pyran-4-ylmethyl)amino]phenyl}sulfonyl)-4-[4-(2-{[(1R,2S,3S,5S)-2,6,6-trimethylbicyclo[3.1.1]hept-3-yl]amino}benzyl)piperazin-1-yl]benzamide;

4-(4-{2-[3-azabicyclo[3.2.2]non-3-yl]benzyl}piperazin-1-yl)-N-({3-nitro-4-[(tetrahydro-2H-pyran-4-ylmethyl)amino]phenyl}sulfonyl)benzamide;

N-({3-nitro-4-[(tetrahydro-2H-pyran-4-ylmethyl)amino]phenyl}sulfonyl)-4-(4-{2-[tricyclo[4.3.1.13,8]undec-4-en-4-yl]benzyl}piperazin-1-yl)benzamide;

7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}-N-phenylbicyclo[2.2.1]hept-2-ene-1-carboxamide;

7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}-N-[(1S,2S3S,5R)-2,6,6-trimethylbicyclo[3.1.1]hept-3-yl]bicyclo[2.2.1]hept-2-ene-1-carboxamide;

N-(adamantan-1-ylmethyl)-7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}bicyclo[2.2.1]hept-2-ene-1-carboxamide;

N-cyclopropyl-7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}bicyclo[2.2.1]hept-2-ene-1-carboxamide:

7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}bicyclo[2.2.1]hept-2-ene-1-carboxylic;

4-[4-(2-{5-[8-azabicyclo[3.2.1]oct-8-ylmethyl]-2-thienyl}benzyl)piperazin-1-yl]-N-({3-nitro-4-[(tetrahydro-2H-pyran-4-ylmethyl)amino]phenyl}sulfonyl)benzamide:

4-{4-[adamantan-1-ylcarbonyl]piperazin-1-yl}-N-{[3-nitro-4-(tetrahydro-2H-pyran-4-ylamino)phenyl]sulfonyl}benzamide;

4-{4-[adamantan-2-ylcarbonyl]piperazin-1-yl}-N-{[3-nitro-4-(tetrahydro-2H-pyran-4-ylamino)phenyl]sulfonyl}benzamide;

4-{5-[adamantan-1-ylcarbonyl]-2,5-diazabicyclo[2.2.1]hept-2-yl}-N-{[3-nitro-4-tetrahydro-2H-pyran-4-ylamino)phenyl]sulfonyl}benzamide;

4-{1S,5S)-3-[adamantan-1-ylcarbonyl]-3,6-diazabicyclo[3.2.0]hept-6-yl}-N-{[3-nitro-4-(tetrahydro-2H-pyran-4-ylamino)phenyl]sulfonyl}benzamide;

N-{[3-nitro-4-(tetrahydro-2H-pyran-4-ylamino)phenyl]sulfonyl}-4-{(3-phenylpropyl)[(1S,2S,3S,5R)-2,6,6-trimethylbicyclo[3.1.1]hept-3-yl]amino}piperidin-1-yl)benzamide;

N-({[4-[(cyclohexylmethyl)amino]-3-nitrophenyl}sulfonyl)-4-(4-{(3-phenylpropanoyl)[(1S,2S,3S,5R)-2,6,6-trimethylbicyclo[3.1.1]hept-3-yl]amino}piperidin-1-yl)benzamide;

4-{4-[adamantan-1-ylmethyl]piperazin-1-yl}-N-({4-[(cyclohexylmethyl)amino]-3-nitrophenyl}sulfonyl)benzamide;

6-{3-[adamantan-1-yl]-4-hydroxyphenyl}-N-({4-[(cyclohexylmethyl)amino]-3-nitrophenyl}sulfonyl)-2-naphthamide;

4-(4-{2-[adamantan-1-yl]-2-oxoethyl}piperazin-1-yl)-N-({4-[(cyclohexylmethyl)amino]-3-nitrophenyl}sulfonyl)benzamide;

4-{[adamantan-2-ylmethyl]amino}-N-{[3-nitro-4-(tetrahydro-2H-pyran-4-ylamino)phenyl]sulfonyl}benzamide;

4-{2-[adamantan-1-yl]ethoxy}-N-{[3-nitro-4-(tetrahydro-2H-pyran-4-ylamino)phenyl]sulfonyl}benzamide;

N3-[adamantan-1-ylacetyl]-N3-benzyl-N-({4-[(cyclohexylmethyl)amino]-3-nitrophenyl}sulfonyl)-beta-alaninamide;

N-({4-[(cyclohexylmethyl)amino]-3-nitrophenyl}sulfonyl)-4-{4-[(1S,2S,3S,5R)-2,6,6-trimethylbicyclo[3.1.1]hept-3-yl]piperazin-1-yl}benzamide;

4-{4-[adamantan-1-yl]piperazin-1-yl}-N-({4-[(cyclohexylmethyl)amino]-3-nitrophenyl}sulfonyl)benzamide.

N-({4-[(cyclohexylmethyl)amino]-3-nitrophenyl}sulfonyl)-4-{4-[3,5-dimethyladamantan-1-yl]piperazin-1-yl}benzamide:

[(3aS,5aR,8aR,8bS)-2,2,7,7-tetramethyltetrahydro-3aH-bis[1,3]dioxolo[4,5-b4',5'-d]pyran-3a-yl]methyl;

4-{4-[(4'-chlorobiphenyl-2-yl)methyl]piperazin-1-yl}-N-({[(1R,4S)-7,7-dimethyl-2-oxobicyclo[2.2.1]hept-1-yl]methyl}sulfonyl)benzamide;

4-(4-{2-[adamantan-1-yl]ethyl}piperazin-1-yl)-N-({4-[(cyclohexylmethyl)amino]-3-nitrophenyl}sulfonyl)benzamide, 4-{4-[(4'-chlorobiphenyl-2-yl)methyl]piperazin-1-yl}-N-({[(1S,4R)-7,7-dimethyl-2-oxobicyclo[2.2.1]hept-1-yl]methyl}sulfonyl)benzamide;

N-({4-[(cyclohexylmethyl)amino]-3-nitrophenyl}sulfonyl)-4'-({(3-phenylpropanoyl)[(1S,2S,3S,5R)-2,6,6-trimethylbicyclo[3.1.1]hept-3-yl]amino}methyl)biphenyl-4-carboxamide;

N-({3-nitro-4-[(tetrahydro-2H-pyran-4-ylmethyl)amino]phenyl}sulfonyl)-4-(4-{2-[(1R,4R)-1,7,7-trimethylbicyclo[2.2.1]hept-2-en-2-yl]benzylidene}piperidin-1-yl)benzamide;

N-({3-nitro-4-[(tetrahydro-2H-pyran-4-ylmethyl)amino]phenyl}sulfonyl)-4-(4-{2-[5-(4-phenyl-1,3-thiazol-2-yl)-2-thienyl]benzyl}piperazin-1-yl)benzamide;

4-[4-(2-{5-[4-(adamantan-1-yl)-1,3-thiazol-2-yl]-2-thienyl}benzyl)piperazin-1-yl]-N-({3-nitro-4-[(tetrahydro-2H-pyran-4-ylmethyl)amino]phenyl}sulfonyl)benzamide;

5-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}-N-(2-phenyl-1,3-benzoxazol-5-yl)-2-furamide;

N-({3-nitro-4-[(tetrahydro-2H-pyran-4-ylmethyl)amino]phenyl}sulfonyl)-4-{4-[2-(triphenylvinyl)benzyl]piperazin-1-yl}benzamide;

4-{4-[2-(5-methyl-5,6-dihydrophenanthridin-6-yl)benzyl]piperazin-1-yl}-N-({3-nitro-4-[(tetrahydro-2H-pyran-4-ylmethyl)amino]phenyl}sulfonyl)benzamide;

N-({3-nitro-4-[(tetrahydro-2H-pyran-4-ylmethyl)amino] phenyl}sulfonyl)-4-{4-[2-(4,4,5,5-tetramethyl-1,3,2-dioxaborolan-2-yl)benzyl]piperazin-1-yl}benzamide;

4-(4-{2-[2-(2,6-dimethoxybenzoyl)-3-thienyl] benzylidene}piperidin-1-yl)-N-({3-nitro-4-[(tetrahydro-2H-pyran-4-ylmethy)amino]phenyl}sulfonyl)benzamide;

1-[adamantan-1-yl]-4-{2-[(1-{4-[({3-nitro-4-[(tetrahydro-2H-pyran-4-ylmethyl)amino]phenyl}sulfonyl)carbamoyl]phenyl}piperidin-4-ylidene)methyl]phenyl}-N,N-diphenyl-1H-pyrazole-3-carboxamide;

N-({3-nitro-4-[(tetrahydro-2H-pyran-4-ylmethyl)amino] phenyl}sulfonyl)-4-(4-{2-[octahydro-1H-4,7-methanoinden-5-yl(3-phenylpropanoyl)amino] benzyl}piperazin-1-yl)benzamide;

4-[4-(2-{5-[8-azabicyclo[3.2.1]oct-8-ylmethyl]-2-thienyl}benzylidene)piperidin-1-yl]-N-({3-nitro-4-[(tetrahydro-2-pyran-4-ylmethyl)amino] phenyl}sulfonyl)benzamide;

N-({3-nitro-4-[(tetrahydro-2H-pyran-4-ylmethyl)amino] phenyl}sulfonyl)-4-[4-(4-{[(1S,2S,3S,5R)-2,6,6-trimethylbicyclo[3.1.1]hept-3-yl]amino}benzylidene)piperidin-1-yl]benzamide;

N-({3-nitro-4-[(tetrahydro-2H-pyran-4-ylmethyl)amino] phenyl}sulfonyl)-4-[4-(3-{[(1S,2S,3S,5R)-2,6,6-trimethylbicyclo[3.1.1]hept-3-yl]amino}benzylidene)piperidin-1-yl]benzamide;

4-[4-(2-{5-[4-(adamantan-1-yl)-1,3-thiazol-2-yl]-2-thienyl}benzylidene)piperidin-1-yl]-N-({3-nitro-4-[(tetrahydro-2H-pyran-4-ylmethyl)amino] phenyl}sulfonyl)benzamide;

N-({3-nitro-4-[(tetrahydro-2H-pyran-4-ylmethyl)amino] phenyl}sulfonyl)-4-(4-{2-[5-(4-phenyl-1,3-thiazol-2-yl)-2-thienyl]benzylidene}piperidin-1-yl)benzamide;

N-[(4-{[adamantan-1-tlmethyl]amino}-3-nitrophenyl) sulfonyl]-4-(4-oxo-4H-chromen-6-yl)benzamide;

N-[(4-{[adamantan-1-ylmethyl]amino}-3-nitrophenyl) sulfonyl]-4-(1-octyl-1H-pyrazol-4-yl)benzamide, 4-[5-(4-{[(4-{[adamantan-1-ylmethyl]amino}-3-nitrophenyl)sulfonyl]carbamoyl}phenyl)-1,3-benzothiazol-2-yl]butanoic;

N-{[3-nitro-4-(tetrahydro-2H-pyran-4-ylamino)phenyl] sulfonyl}-4-[(1R,5S)-1,8,8-trimethyl-3-azabicyclo [3.2.1]oct-3-yl]benzamide;

6-{3-[adamantan-1-yl]-4-methoxyphenyl}-N-({4-[(cyclohexylmethyl)amino]-3-nitrophenyl}sulfonyl)-2-naphthamide;

4-{4-[adamantan-1-ylacetyl]piperazin-1-yl}-N-{[3-nitro-4-(tetrahydro-2H-pyran-4-ylamino)phenyl] sulfonyl}benzamide;

4-{[adamantan-1-ylmethyl]amino}-N-{[3-nitro-4-(tetrahydro-2H-pyran-4-ylamino)phenyl] sulfonyl}benzamide;

N-{1-[4-({[3-nitro-4-(tetrahydro-2H-pyran-4-ylamino) phenyl]sulfonyl}carbamoyl)phenyl]piperidin-4-yl}adamantane-1-carboxamide;

4-[adamantan-2-ylamino]-N-{[3-nitro-4-(tetrahydro-2H-pyran-4-ylamino)phenyl]sulfonyl}benzamide; and N-{[3-nitro-4-(tetrahydro-2H-pyran-4-ylamino)phenyl] sulfonyl}-4-{[(1R,2R,3R,5S)-2,6,6-trimethylbicyclo [3.1.1]hept-3-yl]oxy}benzamide;

and a therapeutically effective amount of one additional therapeutic agent or more than one additional therapeutic agent.

* * * * *

UNITED STATES PATENT AND TRADEMARK OFFICE
CERTIFICATE OF CORRECTION

PATENT NO. : 8,343,967 B2  Page 1 of 2
APPLICATION NO. : 13/458968
DATED : January 1, 2013
INVENTOR(S) : Ding et al.

It is certified that error appears in the above-identified patent and that said Letters Patent is hereby corrected as shown below:

In the Claims

Column 89, line 14, claim 1: "[1S,2S,3S,5R)" to read as --[(1S,2S,3S,5R)--

Column 89, line 17, claim 1: "yl" to read as --ylmethyl--

Column 89, line 39, claim 1: "octahydro" to read as --[octahydro--

Column 90, line 2, claim 1: "yimethyl" to read as --ylmethyl--

Column 90, line 23, claim 1: "N-cyclootyl" to read as --N-cyclooctyl--

Column 90, line 45, claim 1: "dimethyl-{2" to read as --dimethyl-2-{2--

Column 91, line 14, claim 1: "4-{1S,5S)" to read as --4-{(1S,5S)--

Column 91, line 22, claim 1: "N-{4" to read as --N-({4--

Column 91, line 38, claim 1: "4-tetrahydro" to read as --4-(tetrahydro--

Column 91, line 52, claim 1: "benzamide:" to read as --benzamide;--

Column 92, line 6, claim 1: "phenyl}sulfonyl" to read as --phenyl}sulfonyl)--

Column 92, line 18, claim 1: "phenyl}sulfonyl" to read as --phenyl}sulfonyl)--

Column 92, line 20, claim 1: "6-yl benzyl]" to read as --6-yl)benzyl]--

Column 92, line 43, claim 1: "4 ylmethyl" to read as --4-ylmethyl--

Column 92, line 44, claim 1: "3S 5R" to read as --3S,5R--

Column 92, line 48, claim 1: "2S 3S" to read as --2S,3S--

Signed and Sealed this
Thirteenth Day of May, 2014

Michelle K. Lee
*Deputy Director of the United States Patent and Trademark Office*

CERTIFICATE OF CORRECTION (continued)
U.S. Pat. No. 8,343,967 B2

Column 93, line 60, claim 2: "N-[4" to read as --N-[(4--

Column 94, line 18, claim 2: "octahydro" to read as --[octahydro--

Column 94, line 20, claim 2: "ylmety" to read as --ylmethyl--

Column 94, line 25, claim 2: "N-{3-nitro" to read as --N-({3-nitro--

Column 95, line 59, claim 2: "4-tetrahydro" to read as --4-(tetrahydro--

Column 95, line 61, claim 2: "4-{1S,5S)" to read as --4-{(1S,5S)--

Column 95, line 65, claim 2: "4-{(3-phenylpropyl)" to read as --4-(4-{(3-phenylpropyl)--

Column 96, line 1, claim 2: "N-({[4" to read as --N-({4--

Column 97, line 6, claim 2: "ylmethy" to read as --ylmethyl--

Column 97, line 17, claim 2: "2-pyran" to read as --2H-pyran--

Column 98, line 1, claim 2: "tlmethyl" to read as --ylmethyl--

Column 98, line 4, claim 2: "benzamide," to read as --benzamide;--